US012774491B2

(12) United States Patent
Heron et al.

(10) Patent No.: US 12,774,491 B2
(45) Date of Patent: Oct. 27, 2026

(54) METHOD

(71) Applicant: Oxford Nanopore Technologies plc, Oxford (GB)

(72) Inventors: Andrew John Heron, Oxford (GB); Mark John Bruce, Oxford (GB); Rebecca Victoria Bowen, Oxford (GB); Luke Alexander McNeill, Oxford (GB); Simon Rafael Villarreal, Oxford (GB); Samuel John Martin, Oxford (GB); Rebecca Anne Stafford-Allen, Oxford (GB)

(73) Assignee: Oxford Nanopore Technologies PLC, Oxford (GB)

( * ) Notice: Subject to any disclaimer, the term of this patent is extended or adjusted under 35 U.S.C. 154(b) by 1182 days.

(21) Appl. No.: 17/612,606

(22) PCT Filed: May 22, 2020

(86) PCT No.: PCT/GB2020/051260
§ 371 (c)(1),
(2) Date: Nov. 19, 2021

(87) PCT Pub. No.: WO2020/234612
PCT Pub. Date: Nov. 26, 2020

(65) Prior Publication Data

US 2024/0240245 A1 Jul. 18, 2024

(30) Foreign Application Priority Data

May 22, 2019 (GB) ..................................... 1907244

(51) Int. Cl.
*C12Q 1/68* (2018.01)
*C12Q 1/6806* (2018.01)
*C12Q 1/6869* (2018.01)

(52) U.S. Cl.
CPC ......... *C12Q 1/6869* (2013.01); *C12Q 1/6806* (2013.01)

(58) Field of Classification Search
None
See application file for complete search history.

(56) References Cited

U.S. PATENT DOCUMENTS 5,576,204 A 11/1996 Blanco et al.
6,114,121 A 9/2000 Fujiwara et al.
(Continued)

FOREIGN PATENT DOCUMENTS

CN 102245760 A 11/2011
EP 2194123 B1 8/2012
(Continued)

OTHER PUBLICATIONS

GB1907244.6, Feb. 18, 2020, Search Report.
(Continued)

*Primary Examiner* — Aaron A Priest
(74) *Attorney, Agent, or Firm* — Wolf, Greenfield & Sacks, P.C.

(57) ABSTRACT

Provided herein is a method of loading a motor protein onto a polynucleotide adapter. Also provided are polynucleotide adapters and kits comprising such adapters. The adapters find use in characterising analytes such as polynucleotides in methods in which the polynucleotide moves in respect of a nanopore.

23 Claims, 3 Drawing Sheets

Specification includes a Sequence Listing.

(56) References Cited

U.S. PATENT DOCUMENTS

| | | | |
|---|---|---|---|
| 6,150,112 A | 11/2000 | Weissman et al. | |
| 10,059,988 B2 * | 8/2018 | Akeson | G01N 33/48721 |
| 10,221,450 B2 | 3/2019 | Heron et al. | |
| 10,385,389 B2 | 8/2019 | Heron et al. | |
| 11,560,589 B2 * | 1/2023 | Heron | G01N 27/44791 |
| 11,725,235 B2 | 8/2023 | Heron et al. | |
| 2001/0044137 A1 | 11/2001 | Heyman et al. | |
| 2002/0197614 A1 | 12/2002 | Weir et al. | |
| 2004/0209299 A1 | 10/2004 | Pinter et al. | |
| 2009/0111115 A1 | 4/2009 | Drmanac et al. | |
| 2010/0035260 A1 * | 2/2010 | Olasagasti | G01N 27/4166 435/6.16 |
| 2010/0075327 A1 | 3/2010 | Maxham et al. | |
| 2010/0092960 A1 | 4/2010 | Fehr | |
| 2010/0120098 A1 | 5/2010 | Grunenwald et al. | |
| 2011/0136676 A1 | 6/2011 | Greene | |
| 2012/0196279 A1 | 8/2012 | Underwood et al. | |
| 2013/0327644 A1 * | 12/2013 | Turner | C12Q 1/6874 204/543 |
| 2014/0194324 A1 | 7/2014 | Gormley et al. | |
| 2015/0011398 A1 | 1/2015 | Lewis et al. | |
| 2015/0152495 A1 * | 6/2015 | Stava | G01N 27/447 435/6.19 |
| 2015/0191709 A1 | 7/2015 | Heron et al. | |
| 2015/0218629 A1 | 8/2015 | Heron et al. | |
| 2016/0010147 A1 * | 1/2016 | Heron | G01N 27/44791 435/6.1 |
| 2017/0240955 A1 * | 8/2017 | White | C12Q 1/6869 |
| 2017/0253910 A1 * | 9/2017 | Brown | C12N 15/1013 |
| 2017/0253923 A1 * | 9/2017 | Garalde | G01N 33/48721 |
| 2017/0306398 A1 * | 10/2017 | Jayasinghe | B01L 3/502761 |
| 2018/0030525 A1 * | 2/2018 | Rand | C12Q 1/6869 |
| 2019/0004029 A1 * | 1/2019 | Branton | G01N 27/40 |
| 2019/0071721 A1 * | 3/2019 | Jayasinghe | C07K 14/245 |
| 2019/0194722 A1 * | 6/2019 | Stoddart | C12Q 1/6806 |
| 2019/0211390 A1 | 7/2019 | Heron et al. | |
| 2020/0024654 A1 * | 1/2020 | Heron | C12Q 1/6876 |
| 2020/0087724 A1 | 3/2020 | Heron et al. | |
| 2022/0042967 A1 * | 2/2022 | Brown | C12Q 1/6869 |
| 2022/0127672 A1 | 4/2022 | Stoeckius | |
| 2023/0212665 A1 | 7/2023 | Heron et al. | |
| 2024/0026441 A1 | 1/2024 | Heron et al. | |

FOREIGN PATENT DOCUMENTS

| | | |
|---|---|---|
| EP | 2682460 | 1/2014 |
| GB | 1314695.6 | 8/2013 |
| JP | H10-146190 | 6/1998 |
| JP | 2005-253427 | 9/2005 |
| JP | 2015-528700 A | 10/2015 |
| JP | 2015-529451 A | 10/2015 |
| JP | 2016-510593 A | 4/2016 |
| JP | 2016-538835 A | 12/2016 |
| JP | 2017-503517 A | 2/2017 |
| WO | WO 2000/28312 | 5/2000 |
| WO | WO 2006/028508 A2 | 3/2006 |
| WO | WO 2006/100484 A2 | 9/2006 |
| WO | WO 2008/102120 A1 | 8/2008 |
| WO | WO 2008/102121 A1 | 8/2008 |
| WO | WO 2009/020682 A2 | 2/2009 |
| WO | WO 2009/035647 A1 | 3/2009 |
| WO | WO 2009/077734 A2 | 6/2009 |
| WO | WO 2010/004265 A1 | 1/2010 |
| WO | WO 2010/086602 A1 | 8/2010 |
| WO | WO 2010/122293 A1 | 10/2010 |
| WO | WO 2012/005857 A1 | 1/2012 |
| WO | WO 2012/107778 A2 | 8/2012 |
| WO | WO 2012/164270 A1 | 12/2012 |
| WO | WO 2013/014451 A1 | 1/2013 |
| WO | WO 2013/057495 A2 | 4/2013 |
| WO | WO 2013/083983 A1 | 6/2013 |
| WO | WO 2013/098561 A1 | 7/2013 |
| WO | WO 2013/098562 A2 | 7/2013 |
| WO | WO 2013/109970 A1 | 7/2013 |
| WO | WO 2013/153359 A1 | 10/2013 |
| WO | WO 2014/013259 A1 | 1/2014 |
| WO | WO 2014/013260 A1 | 1/2014 |
| WO | WO 2014/013262 A1 | 1/2014 |
| WO | WO 2014/064443 A2 | 5/2014 |
| WO | WO 2014/064444 A1 | 5/2014 |
| WO | WO 2014/135838 A1 | 9/2014 |
| WO | WO 2014/142850 A1 | 9/2014 |
| WO | WO 2014/187924 A1 | 11/2014 |
| WO | WO 2015/055981 A2 | 4/2015 |
| WO | WO 2015/110813 A1 | 7/2015 |
| WO | WO 2015/150786 A1 | 10/2015 |
| WO | WO 2016/034591 A2 | 3/2016 |

OTHER PUBLICATIONS

PCT/GB2014/050175, May 9, 2014, International Search Report and Written Opinion.

PCT/GB2014/050175, Sep. 17, 2015, International Preliminary Report on Patentability.

PCT/GB2015/050140, May 8, 2015, International Search Report and Written Opinion.

PCT/GB2015/050140, Aug. 4, 2016, International Preliminary Report on Patentability.

PCT/GB2020/051260, Jul. 10, 2020, International Search Report and Written Opinion.

PCT/GB2020/051260, Dec. 2, 2021, International Preliminary Report on Patentability.

United Kingdom Search Report for Application No. GB1907244.6 mailed Feb. 18, 2020.

International Search Report and Written Opinion for Application No. PCT/GB2014/050175 mailed May 9, 2014.

International Preliminary Report on Patentability for Application No. PCT/GB2014/050175 mailed Sep. 17, 2015.

International Search Report and Written Opinion for Application No. PCT/GB2015/050140, mailed May 8, 2015.

International Preliminary Report on Patentability for Application No. PCT/GB2015/050140, mailed Aug. 4, 2016.

International Search Report and Written Opinion for Application No. PCT/GB2020/051260 mailed Jul. 10, 2020.

International Preliminary Report on Patentability for Application No. PCT/GB2020/051260 mailed Dec. 2, 2021.

[No Author Listed] Nextera™ DNA Sample Preparation Kits (Illumina) Oct. 2011. (2 pages).

[No Author Listed] Oxford Nanopore ""Product"" brochure (2020) https://nanoporetech.com/sites/default/files/s3/literature/product-brochure.Pdf (36 pages).

Ahern, Biochemical, reagents kits offer scientists good return on investment. The Scientist. Jul. 24, 1995;9(15):20.

Burton et al., ClpX-mediated remodeling of mu transpososomes: selective unfolding of subunits destabilizes the entire complex. Mol Cell. Aug. 2001;8(2):449-54. doi: 10.1016/s1097-2765(01)00307-0.

Caruccio, Preparation of next-generation sequencing libraries using Nextera™ technology: simultaneous DNA fragmentation and adaptor tagging by in vitro transposition. Methods Mol Biol. 2011;733:241-55. doi: 10.1007/978-1-61779-089-8_17.

Colas et al., Microscopical investigations of nisin-loaded nanoliposomes prepared by Mozafari method and their bacterial targeting. Micron. 2007;38(8):841-7. doi: 10.1016/j.micron.2007.06.013. Epub Jul. 3, 2007.

De Vlaminck et al., Mechanism of homology recognition in DNA recombination from dual-molecule experiments. Mol Cell. Jun. 8, 2012;46(5):616-24. doi: 10.1016/j.molcel.2012.03.029. Epub May 3, 2012.

Eoff et al., Chemically modified DNA substrates implicate the importance of electrostatic interactions for DNA unwinding by Dda helicase. Biochemistry. Jan. 18, 2005;44(2):666-74.

González-Pérez et al., Biomimetic triblock copolymer membrane arrays: a stable template for functional membrane proteins. Langmuir. Sep. 15, 2009;25(18):10447-50. doi: 10.1021/la902417m.

Goryshin et al., Tn5 in vitro transposition. J Biol Chem. Mar. 27, 1998;273(13):7367-74. doi: 10.1074/jbc.273.13.7367.

(56) References Cited

OTHER PUBLICATIONS

Haque et al., DNA-associated click chemistry. Science China Chemistry. Feb. 2014;57(2):215-231. doi:10.1007/s11426-013-5035-1.
Heron et al., Simultaneous measurement of ionic current and fluorescence from single protein pores. J Am Chem Soc. Feb. 11, 2009;131(5):1652-3. doi: 10.1021/ja808128s.
Higgins et al., DNA-joining enzymes: a review. Methods Enzymol. 1979;68:50-71. doi: 10.1016/0076-6879(79)68006-0.
Jain et al., The Oxford Nanopore MinION: delivery of nanopore sequencing to the genomics community. Genome Biol. Nov. 25, 2016;17(1):239. doi: 10.1186/s13059-016-1103-0. Erratum in: Genome Biol. Dec. 13, 2016;17 (1):256.
Kanaan et al., UPF1-like helicase grip on nucleic acids dictates processivity. Nat Commun. Sep. 14, 2018;9(1):3752. doi: 10.1038/s41467-018-06313-y.
Keyser, Controlling molecular transport through nanopores. J R Soc Interface. Oct. 7, 2011;8(63):1369-78. doi: 10.1098/rsif.2011.0222. Epub Jun. 29, 2011.
Klenchin et al., Phosphate coordination and movement of DNA in the Tn5 synaptic complex: role of the (R)YREK motif. Nucleic Acids Res. Oct. 2008;36(18):5855-62. doi: 10.1093/nar/gkn577. Epub Sep. 12, 2008.
Langecker et al., Synthetic lipid membrane channels formed by designed DNA nanostructures. Science. Nov. 16, 2012;338(6109):932-6. doi: 10.1126/science.1225624.
Le et al., Thermostable DNA ligase-mediated PCR production of circular plasmid (PPCP) and its application in directed evolution via in situ error-prone PCR. DNA Res. Aug. 2013;20(4):375-82. doi: 10.1093/dnares/dst016. Epub Apr. 30, 2013.
Li et al., ChIA-PET tool for comprehensive chromatin interaction analysis with paired-end tag sequencing. Genome Biol. 2010;11(2):R22. doi: 10.1186/GB-2010-11-2-r22. Epub Feb. 25, 2010.
Lovett, The DNA Exonucleases of *Escherichia coli*. EcoSal Plus. Dec. 2011;4(2):10.1128/ecosalplus.4.4.7. doi: 10.1128/ecosalplus.4.4.7. Author Manuscript, 45 pages.
Maine et al., Inhibition of the DNA unwinding and ATP hydrolysis activities of the bacteriophage T4 DDA helicase by a sequence specific DNA-protein complex. Biochem Biophys Res Commun. Feb. 15, 1994;198(3):1070-7. doi: 10.1006/bbrc.1994.1152.
Manosas et al., Magnetic tweezers for the study of DNA tracking motors. Methods Enzymol. 2010;475:297-320. doi: 10.1016/S0076-6879(10)75013-8.
Matson et al., The gene 4 protein of bacteriophage T7. Characterization of helicase activity. J Biol Chem. Nov. 25, 1983;258(22):14017-24.
Montal et al., Formation of bimolecular membranes from lipid monolayers and a study of their electrical properties. Proc Natl Acad Sci U S A. Dec. 1972;69(12):3561-6. doi: 10.1073/pnas.69.12.3561.
Reznikoff, Tn5 as a model for understanding DNA transposition. Mol Microbiol. Mar. 2003;47(5):1199-206. doi: 10.1046/j.1365-2958.2003.03382.x.
Rhee et al., Comprehensive genome-wide protein-DNA interactions detected at single-nucleotide resolution. Cell. Dec. 9, 2011;147(6):1408-19. doi: 10.1016/j.cell.2011.11.013.
Saariaho et al., Characteristics of MuA transposase-catalyzed processing of model transposon end DNA hairpin substrates. Nucleic Acids Res. Jun. 6, 2006;34(10):3139-49.
Shelbourne et al., Fast copper-free click DNA ligation by the ring-strain promoted alkyne-azide cycloaddition reaction. Chem Commun (Camb). Jun. 14, 2011;47(22):6257-9. doi: 10.1039/c1cc10743g. Epub May 6, 2011.
Sternberg et al., DNA interrogation by the CRISPR RNA-guided endonuclease Cas9. Nature. Mar. 6, 2014;507(7490):62-7. doi: 10.1038/nature13011. Epub Jan. 29, 2014. Author Manuscript, 16 pages.
Stoddart et al., Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.
Tackett et al., Unwinding of unnatural substrates by a DNA helicase. Biochemistry. Jan. 16, 2001;40(2):543-8.
Tuteja et al., Helicases as molecular motors: An insight. Physica A. Dec. 1, 2006;372(1):70-83. doi: 10.1016/j.physa.2006.05.014. Epub Jun. 5, 2006.
Wang et al., Measuring and modeling the kinetics of individual DNA-DNA polymerase complexes on a nanopore. ACS Nano. May 28, 2013;7(5):3876-86. doi: 10.1021/nn401180j. Epub Apr. 16, 2013.
Wiedmann et al., Ligase chain reaction (LCR)—overview and applications. PCR Methods Appl. Feb. 1994;3(4):S51-64. doi: 10.1101/gr.3.4.s51.
Wilkinson et al., Bacterial DNA ligases. Mol Microbiol. Jun. 2001;40(6):1241-8. doi: 10.1046/j.1365-2958.2001.02479.x.
Wu et al., Sequence-specific capture of protein-DNA complexes for mass spectrometric protein identification. PLoS One. 2011;6(10):e26217. doi: 10.1371/journal.pone.0026217. Epub Oct. 20, 2011.
Yen et al., SWR-C and INO80 chromatin remodelers recognize nucleosome-free regions near +1 nucleosomes. Cell. Sep. 12, 2013;154(6):1246-56. doi: 10.1016/j.cell.2013.08.043.
[No Author Listed] Ligase from Wikipedia. Printed on Mar. 31, 2026.

* cited by examiner

1A

1B

1C

METHOD

RELATED APPLICATIONS

This application is a national stage filing under 35 U.S.C. § 371 of international application number PCT/GB2020/051260, filed May 22, 2020, which claims the benefit of the filing date of Great Britain application number GB 1907244.6, filed May 22, 2019, the entire contents of each of which are incorporated herein by reference.

REFERENCE TO A SEQUENCE LISTING SUBMITTED AS A TEXT FILE VIA EFS-WEB

This application contains a Sequence Listing which has been submitted in ASCII format via EFS-Web and is hereby incorporated by reference in its entirety. Said ASCII copy, created on Aug. 9, 2022 is named 0036670120US00-SUB-SEQ-LJG and is 39,682 bytes in size.

FIELD

The present invention relates to methods of loading motor proteins onto polynucleotide adapters, to methods of characterising polynucleotides using the novel methods, and to novel polynucleotide adapters.

BACKGROUND

Nanopore sensing is an approach to analyte detection and characterization that relies on the observation of individual binding or interaction events between the analyte molecules and an ion conducting channel. Nanopore sensors can be created by placing a single pore of nanometre dimensions in an electrically insulating membrane and measuring voltage-driven ion currents through the pore in the presence of analyte molecules. The presence of an analyte inside or near the nanopore will alter the ionic flow through the pore, resulting in altered ionic or electric currents being measured over the channel. The identity of an analyte is revealed through its distinctive current signature, notably the duration and extent of current blocks and the variance of current levels during its interaction time with the pore.

Polynucleotides are important analytes for sensing in this manner. Nanopore sensing of polynucleotide analytes can reveal the identity and perform single molecule counting of the sensed analytes, but can also provide information on their composition such as their nucleotide sequence, as well as the presence of characteristics such as base modifications, oxidation, reduction, decarboxylation, deamination and more. Nanopore sensing has the potential to allow rapid and cheap polynucleotide sequencing, providing single molecule sequence reads of polynucleotides of tens to tens of thousands bases length.

Two of the essential components of polymer characterization using nanopore sensing are (1) the control of polymer movement through the pore and (2) the discrimination of the composing building blocks as the polymer is moved through the pore. During nanopore sensing of analytes such as polynucleotides, it is important to control the movement of the polynucleotide with respect to the pore. Uncontrolled movement can prevent or impede accurate characterisation of the polynucleotides. For example, accurately distinguishing each nucleotide in a homopolymeric polynucleotide is problematic when the movement of the polynucleotide with respect to the pore is not controlled.

To address this problem, it is known to use a motor protein to control the movement of a polymer such as a polynucleotide whilst it is characterised. Suitable motor proteins include polynucleotide-handling enzymes such as helicases, exonucleases, topoisomerases and the like. The motor protein processes the polynucleotide in a controlled manner. The motor protein can thus be used to control the movement of a polymer such as a polynucleotide with respect to the pore.

Whilst the use of motor proteins has allowed significant improvements to be achieved in the processing of polynucleotides for characterisation by nanopore sensing, technical challenges remain. One issue concerns ensuring that the motor protein is in the correct position with respect to the polynucleotide sequence to be determined prior to the start of the characterisation. For example, if the motor protein has already begun to process the polynucleotide prior to the start of the characterisation then the portion of the polynucleotide that has been processed prior to the start of the characterisation may not be accurately determined.

To address this, it is known to "stall" the motor protein on a polynucleotide adapter prior to the characterisation. The motor protein does not process the target polynucleotide until the characterisation is begun. In this way, improved characterisation of the target polynucleotide is possible.

One method known in the art is to stall a motor protein such as a helicase on a molecular adapter using a spacer. The spacer is a portion of the adapter which impedes the movement of the motor protein (e.g. helicase) onto the target polynucleotide to be characterised. In the absence of an external force, the movement of the motor protein (helicase) onto the target polynucleotide is prevented. However, under the influence of an external force, which can for example be provided by passing the target polynucleotide through a nanopore, the motor protein can move onto the target polynucleotide and thereby control the movement of the target polynucleotide with respect to the pore. Such methods are described in WO 2014/135838, the entire contents of which are incorporated by reference.

Whilst methods of stalling motor proteins have led to significant benefits, it has been recognised that the efficiency of such systems could be improved if the turnover of "fuel" molecules (e.g. cofactors required for polynucleotide processing) by the stalled motor protein could be reduced. Accordingly, there is a need for improved methods for loading polynucleotides onto molecular adapters which address this.

SUMMARY

The disclosure relates to a method of loading a motor protein onto a polynucleotide adapter. The methods comprise providing a polynucleotide adapter comprising a spacer. The polynucleotide adapter is contacted with a motor protein causing the motor protein to progress onto the spacer. A blocking moiety is bound to the polynucleotide adapter. Binding the blocking moiety to the polynucleotide adapter prevents the motor protein from moving off the spacer. Preventing the motor protein from moving off the spacer may have beneficial effects, such as reducing the rate at which the motor protein turns over fuel molecules compared to when the motor protein is bound to a polynucleotide.

Accordingly, provided herein is a method of loading a motor protein onto a polynucleotide adapter, the method comprising:

i) providing a polynucleotide adapter comprising a spacer;
ii) contacting the polynucleotide adapter with a motor protein; and
iii) positioning the motor protein on the spacer;

wherein a blocking moiety bound to the polynucleotide adapter prevents the motor protein from moving off the spacer.

In some embodiments, the method comprises:

i) providing a polynucleotide adapter comprising a spacer and a blocking moiety bound to the polynucleotide adapter;
ii) contacting the polynucleotide adapter with a motor protein; and
iii) positioning the motor protein on the spacer;

wherein the blocking moiety prevents the motor protein from moving off the spacer.

Also provided is a method of loading a motor protein onto a polynucleotide adapter, the method comprising:

i) providing a polynucleotide adapter comprising a spacer;
ii) contacting the polynucleotide adapter with a motor protein;
iii) causing the motor protein to progress onto the spacer; and
iv) binding a blocking moiety to the polynucleotide adapter, wherein the blocking moiety prevents the motor protein from moving off the spacer.

In one embodiment, the method comprises i) providing a polynucleotide adapter comprising a loading site connected to a spacer;
ii) contacting the loading site with a motor protein;
iii) causing the motor protein to progress from the loading site onto the spacer; and
iv) binding a blocking moiety to the polynucleotide adapter, wherein the blocking moiety prevents the motor protein from moving off the spacer and onto the loading site.

In one embodiment, step (ii) of the method comprises contacting the loading site with a motor protein, wherein the motor protein engages with the loading site; and step (iv) of the method comprises binding a blocking moiety to the polynucleotide adapter, wherein the blocking moiety prevents the motor protein from moving off the spacer and re-engaging with the loading site.

In one embodiment, the polynucleotide adapter comprises a loading site connected to a spacer and wherein the motor protein binds to the loading site of the polynucleotide adapter.

In some embodiments, causing the motor protein to progress onto the spacer comprises applying a physical or chemical force to the motor protein. In one embodiment, causing the motor protein to progress onto the spacer may comprise contacting the motor protein with one or more fuel molecules. In one embodiment, the polynucleotide adapter comprises a loading site connected to a spacer; the motor protein is a first motor protein and causing the first motor protein to progress from the loading site onto the spacer comprises loading a second motor protein onto the loading site and causing the second motor protein to progress from the loading site towards the spacer, wherein the second motor protein forces the first motor protein onto the spacer. In one embodiment, binding the blocking moiety to the polynucleotide adapter forces the motor protein onto the spacer.

In some embodiments, the polynucleotide adapter comprises a loading site connected to a spacer and the blocking moiety binds to the loading site. In one embodiment, the loading site is contiguous with the spacer and the blocking moiety binds to the loading site immediately adjacent to the spacer.

In one embodiment, step (iii) comprises causing the motor protein to progress onto the spacer such that the spacer occupies the active site of the motor protein.

In some embodiments, the polynucleotide adapter comprises a loading site connected to a spacer and the loading site comprises a single-stranded or non-hybridised polynucleotide. In one embodiment, the loading site comprises a single-stranded or non-hybridised polynucleotide having a length of between about 2 and about 1000 nucleotide units.

In some embodiments, the blocking moiety is a physical or chemical blocking moiety. In one embodiment, binding the blocking moiety to the polynucleotide adapter sterically prevents the movement of the motor protein off the spacer. In one embodiment, binding the blocking moiety to the polynucleotide adapter introduces a chemical group which prevents movement of the motor protein off the spacer.

In some embodiments, (i) the loading moiety comprises a single-stranded or non-hybridised polynucleotide and the blocking moiety comprises a single-stranded or non-hybridised polynucleotide; and (ii) binding the blocking moiety to the loading site comprises hybridising the blocking moiety to the loading site. In one embodiment, the blocking moiety comprises a single-stranded or non-hybridised polynucleotide having a length of between about 2 and about 1000 nucleotide units.

In some embodiments, the spacer comprises:

i) one or more nitroindoles, one or more inosines, one or more acridines, one or more 2-aminopurines, one or more 2-6-diaminopurines, one or more 5-bromo-deoxyuridines, one or more inverted thymidines (inverted dTs), one or more inverted dideoxy-thymidines (ddTs), one or more dideoxy-cytidines (ddCs), one or more 5-methylcytidines, one or more 5-hydroxymethylcytidines, one or more 2'-O-Methyl RNA bases, one or more Iso-deoxycytidines (Iso-dCs), one or more Iso-deoxyguanosines (Iso-dGs), one or more C3 ($OC_3H_6OPO_3$) groups, one or more photo-cleavable (PC) [$OC_3H_6$—C(O)NHCH$_2$—$C_6H_3NO_2$—CH(CH$_3$)OPO$_3$] groups, one or more hexandiol groups, one or more spacer 9 (iSp9) [$(OCH_2CH_2)_3OPO_3$] groups, or one or more spacer 18 (iSp18) [$(OCH_2CH_2)_6OPO_3$] groups;
ii) one or more thiol connections;
iii) one or more abasic nucleotides;
iv) one or more nucleotides of different backbone structure to the loading site;
v) one or more chemical groups which cause the one or more motor proteins to stall; and/or
vi) a polymer, optionally wherein said polymer is a polypeptide or a polyethylene glycol (PEG).

In some embodiments the spacer comprises one or more nucleotides, preferably wherein the spacer comprises one or more nucleotide islands.

In some embodiments:

i) the polynucleotide adapter comprises a spacer comprising one or more nucleotides, preferably one or more nucleotide islands; and a blocking moiety bound to the polynucleotide adapter; and
ii) positioning the motor protein on the spacer comprises contacting the motor protein with the spacer and modifying the motor protein to prevent the motor protein disengaging from the spacer.

In some embodiments the spacer comprises one or more moieties selected from: —S—N—S—N—S—N—S—;

—S—N—N—S—N—N—S—N—N—S—; —S—S—S—S—S—S—N—N—S—S—; —S—S—S—S—S—N—N—S—N—N—S—S—S—; —S—S—S—N—N—S—N—N—S—S—N—N—S—; —S—S—S—S—S—N—N—S—N—N—S—S—N—N—S—; —S—S—S—N—N—S—N—N—S—N—N—S—; —N—N—S—S—N—N—S—S—S—S—S—; —S—N—N—S—S—N—N—S—S—S—S—; —S—S—N—N—S—S—N—N—S—S—S—; —S—S—S—S—N—N—S—S—N—N—S—; —N—N—S—N—N—S—S—S—S—S—S—; —S—N—N—S—N—N—S—S—S—S—S—; —S—S—N—N—S—N—N—S—S—S—S—; —S—S—S—N—N—S—N—N—S—S—S—: —S—S—S—S—N—N—S—N—N—S—S—; and —S—S—S—N—N—S—S—N—N—S—;

wherein each S is a spacer unit and each N is a nucleotide.

In some embodiments, the motor protein is a helicase, a polymerase, an exonuclease, a topoisomerase, or a variant thereof. In one embodiment, the motor protein on the spacer of the polynucleotide adapter is modified to prevent the motor protein disengaging from the spacer. In one embodiment, the or each motor protein is a helicase independently selected from a Hel308 helicase, a RecD helicase, a TraI helicase, a TrwC helicase, an XPD helicase, and a Dda helicase, or a variant thereof.

In one embodiment, the method further comprises the step of (v) removing excess motor protein molecules which are not located on the spacer.

Also provided is a method of controlling the movement of a target polynucleotide with respect to a transmembrane nanopore, comprising:

i) providing (A) a target polynucleotide; (B) a polynucleotide adapter comprising a spacer; and (C) a motor protein;
ii) carrying out a method according to any one of the embodiments described above, thereby stalling the motor protein on the spacer of the polynucleotide adapter;
iii) contacting the target polynucleotide and the stalled motor protein on the spacer of the polynucleotide adapter with the nanopore; and
iv) applying a potential across the transmembrane nanopore thereby causing the motor protein to move past the spacer onto the target polynucleotide thereby controlling the movement of the target polynucleotide with respect to the nanopore.

In one embodiment, the motor protein is stalled on the polynucleotide adapter before the polynucleotide adapter is attached to the target polynucleotide. In another embodiment, the polynucleotide adapter is attached to the target polynucleotide before the motor protein is stalled on the polynucleotide adapter.

Also provided is a method of controlling the movement of a target polynucleotide with respect to a transmembrane nanopore, comprising:

i) providing a target polynucleotide;
ii) providing a polynucleotide adapter comprising a spacer and having a motor protein stalled thereon, wherein said polynucleotide adapter is obtained according to the methods disclosed herein;
iii) contacting the target polynucleotide and the polynucleotide adapter with the nanopore; and
iv) applying a potential across the transmembrane nanopore thereby causing the motor protein to move past the spacer onto the target polynucleotide thereby controlling the movement of the target polynucleotide with respect to the nanopore.

In some embodiments, the methods further comprises taking one or more measurements as the target polynucleotide moves with respect to the nanopore, wherein the one or more measurements are indicative of one or more characteristics of the target polynucleotide, and thereby characterising the target polynucleotide as it moves with respect to the nanopore.

Also provided is a polynucleotide adapter comprising (i) a spacer; (ii) a motor protein stalled on the spacer, wherein the active site of the motor protein is occupied by the spacer; and (iii) a blocking moiety bound to the adapter, wherein the blocking moiety prevents the motor protein from moving off the spacer.

In one embodiment, (i) the adapter comprises a loading site connected to the spacer and the blocking moiety is bound to the loading site; and (ii) the blocking moiety prevents the motor protein from engaging with the loading site.

In one embodiment, the polynucleotide adapter comprises:

i) $\{L_B\text{-S-D}\}_n$ or $\{\text{D-S-}L_B\}_n$ in the 5' to 3' direction; wherein $L_B$ is a blocked loading site; S is a spacer; D is a double-stranded polynucleotide; and n is an integer, optionally an integer from 1 to about 20; and
ii) one or more motor proteins stalled on the spacer (S); wherein the or each $L_B$ moiety prevents the or each motor protein from moving off the spacer (S) in the direction away from the double-stranded polynucleotide (D).

In one embodiment, the polynucleotide adapter comprises:

i) $\{L_B\text{-S-D}\}_n$ or $\{\text{D-S-}L_B\}_n$ in the 5' to 3' direction; wherein $L_B$ is a first double-stranded polynucleotide; S is a spacer; D is a second double-stranded polynucleotide; and n is an integer, optionally an integer from 1 to about 20; and wherein the first double-stranded polynucleotide ($L_B$) is contiguous with the spacer (S) and the spacer (S) is contiguous with the second double-stranded polynucleotide (D); and
ii) one or more motor proteins is stalled on the spacer (S).

Also provided is a kit for modifying a target polynucleotide, comprising:

i) a polynucleotide adapter comprising a spacer;
ii) a motor protein capable of controlling the movement of the target polynucleotide; and
iii) a blocking moiety capable of binding to the polynucleotide adapter so that when the motor protein is located on the spacer of the polynucleotide adapter and the polynucleotide-unwinding site of the motor protein is occupied by the spacer, the motor protein is prevented from moving off the spacer In one embodiment, the polynucleotide adapter comprises a loading site and the blocking moiety is capable of binding to the polynucleotide adapter so that the motor protein is prevented from engaging with the loading site.

Also provided is a kit for modifying a target polynucleotide, comprising:

i) a polynucleotide adapter comprising a spacer and a blocking moiety bound to the polynucleotide adapter; and
ii) a motor protein capable of controlling the movement of the target polynucleotide;

wherein when the motor protein is bound to the adapter, the blocking moiety prevents the motor protein from moving off the spacer.

In some embodiments, the polynucleotide adapter or kit according to the preceding embodiments comprises a loading site, blocking moiety, spacer and/or motor protein each independently as defined in any one the preceding embodiments.

BRIEF DESCRIPTION OF THE FIGURES

FIG. 1(A) shows a schematic representation of constructs comprising double-stranded DNA, followed by spacer (4×Sp18 spacer groups), followed by further double-stranded DNA. The spacer is flanked by the double-stranded DNA so that there is no single-stranded DNA accessible at either end of the spacer. A Dda helicase is stalled on the spacer. FIG. 1(B) shows similar constructs in which the spacer is not flanked by double-stranded DNA and the lower strand is missing ten residues. The construct thus comprises single-stranded DNA flanking the 5' end of the spacer. FIG. 1(C) shows a bar graph comparing the catalytic rate of ATP turnover by Dda helicase enzymes stalled on the constructs of FIG. 1(A) and FIG. 1(B), respectively. This data is discussed in Example 1.

DETAILED DESCRIPTION

Figure 1:
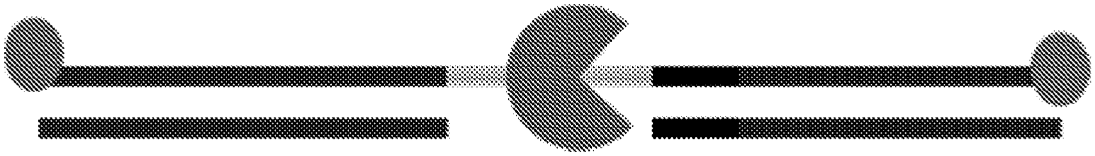
FIG. 1. Futile turnover is reduced using the methods disclosed herein.
Figure 1:
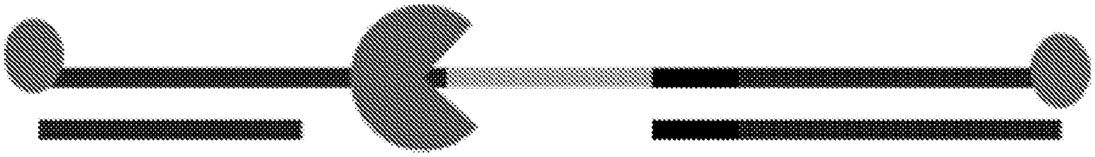
Figure 1:
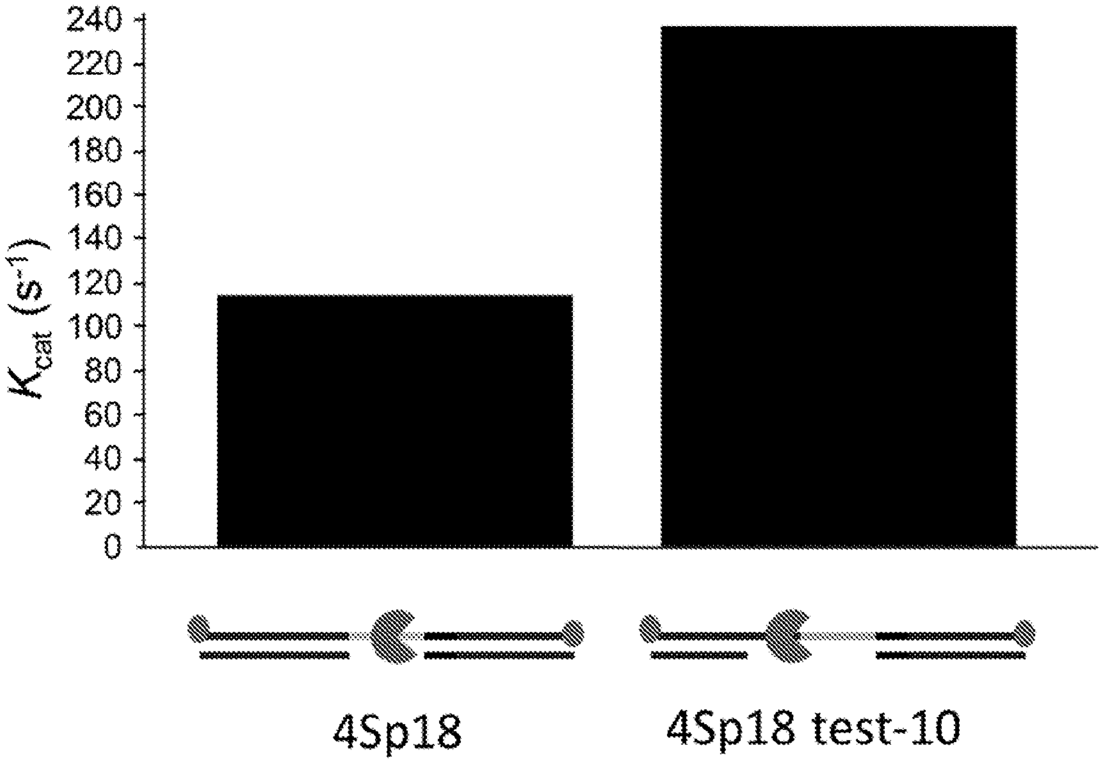

The present invention will be described with respect to particular embodiments and with reference to certain drawings but the invention is not limited thereto but only by the claims. Any reference signs in the claims shall not be construed as limiting the scope. Of course, it is to be understood that not necessarily all aspects or advantages may be achieved in accordance with any particular embodiment of the invention. Thus, for example those skilled in the art will recognize that the invention may be embodied or carried out in a manner that achieves or optimizes one advantage or group of advantages as taught herein without necessarily achieving other aspects or advantages as may be taught or suggested herein.

The invention, both as to organization and method of operation, together with features and advantages thereof, may best be understood by reference to the following detailed description when read in conjunction with the accompanying drawings. The aspects and advantages of the invention will be apparent from and elucidated with reference to the embodiment(s) described hereinafter. Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Similarly, it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment.

It should be appreciated that "embodiments" of the disclosure can be specifically combined together unless the context indicates otherwise. The specific combinations of all disclosed embodiments (unless implied otherwise by the context) are further disclosed embodiments of the claimed invention.

In addition as used in this specification and the appended claims, the singular forms "a", "an", and "the" include plural referents unless the content clearly dictates otherwise. Thus, for example, reference to "a polynucleotide" includes two or more polynucleotides, reference to "a motor protein" includes two or more such proteins, reference to "a helicase" includes two or more helicases, reference to "a monomer" refers to two or more monomers, reference to "a pore" includes two or more pores and the like.

All publications, patents and patent applications cited herein, whether supra or infra, are hereby incorporated by reference in their entirety.

Definitions

Where an indefinite or definite article is used when referring to a singular noun e.g. "a" or "an", "the", this includes a plural of that noun unless something else is specifically stated. Where the term "comprising" is used in the present description and claims, it does not exclude other elements or steps. Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein. The following terms or definitions are provided solely to aid in the understanding of the invention. Unless specifically defined herein, all terms used herein have the same meaning as they would to one skilled in the art of the present invention. Practitioners are particularly directed to Sambrook et al., Molecular Cloning: A Laboratory Manual, $4^{th}$ ed., Cold Spring Harbor Press, Plainsview, New York (2012); and Ausubel et al., Current Protocols in Molecular Biology (Supplement 114), John Wiley & Sons, New York (2016), for definitions and terms of the art. The definitions provided herein should not be construed to have a scope less than understood by a person of ordinary skill in the art.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Nucleotide sequence", "DNA sequence" or "nucleic acid molecule(s)" as used herein refers to a polymeric form of nucleotides of any length, either ribonucleotides or deoxyribonucleotides. This term refers only to the primary structure of the molecule. Thus, this term includes double- and single-stranded DNA, and RNA. The term "nucleic acid" as used herein, is a single or double stranded covalently-linked sequence of nucleotides in which the 3' and 5' ends on each nucleotide are joined by phosphodiester bonds. The polynucleotide may be made up of deoxyribonucleotide bases or ribonucleotide bases. Nucleic acids may be manufactured synthetically in vitro or isolated from natural sources. Nucleic acids may further include modified DNA or RNA, for example DNA or RNA that has been methylated, or RNA that has been subject to post-translational modification, for example 5'-capping with 7-methylguanosine, 3'-processing such as cleavage and polyadenylation, and splicing. Nucleic acids may also include synthetic nucleic acids (XNA), such as hexitol nucleic acid (HNA), cyclohexene nucleic acid (CeNA), threose nucleic acid (TNA), glycerol nucleic acid (GNA), locked nucleic acid (LNA) and peptide nucleic acid (PNA). Sizes of nucleic acids, also referred to herein as "polynucleotides" are typically expressed as the number of base pairs (bp) for double stranded polynucleotides, or in the case of single stranded polynucleotides as the number of nucleotides (nt). One thousand bp or nt equal a kilobase (kb). Polynucleotides of less than around 40 nucleotides in length are typically called "oligonucleotides" and may comprise primers for use in manipulation of DNA such as via polymerase chain reaction (PCR).

The term "amino acid" in the context of the present disclosure is used in its broadest sense and is meant to include organic compounds containing amine ($NH_2$) and carboxyl (COOH) functional groups, along with a side chain (e.g., a R group) specific to each amino acid. In some embodiments, the amino acids refer to naturally occurring L α-amino acids or residues. The commonly used one and three letter abbreviations for naturally occurring amino acids are used herein: A=Ala; C=Cys; D=Asp; E=Glu; F=Phe; G=Gly; H=His; I=Ile; K=Lys; L=Leu; M=Met; N=Asn; P=Pro; Q=Gln; R=Arg; S=Ser; T=Thr; V=Val; W=Trp; and Y=Tyr (Lehninger, A. L., (1975) Biochemistry, 2d ed., pp. 71-92, Worth Publishers, New York). The general term "amino acid" further includes D-amino acids, retro-inverso amino acids as well as chemically modified amino acids such as amino acid analogues, naturally occurring amino acids that are not usually incorporated into proteins such as norleucine, and chemically synthesised compounds having properties known in the art to be characteristic of an amino acid, such as j-amino acids. For example, analogues or mimetics of phenylalanine or proline, which allow the same conformational restriction of the peptide compounds as do natural Phe or Pro, are included within the definition of amino acid. Such analogues and mimetics are referred to herein as "functional equivalents" of the respective amino acid. Other examples of amino acids are listed by Roberts and Vellaccio, The Peptides: Analysis, Synthesis, Biology, Gross and Meiehofer, eds., Vol. 5 p. 341, Academic Press, Inc., N.Y. 1983, which is incorporated herein by reference.

The terms "polypeptide", and "peptide" are interchangeably used herein to refer to a polymer of amino acid residues and to variants and synthetic analogues of the same. Thus, these terms apply to amino acid polymers in which one or more amino acid residues is a synthetic non-naturally occurring amino acid, such as a chemical analogue of a corresponding naturally occurring amino acid, as well as to naturally-occurring amino acid polymers. Polypeptides can also undergo maturation or post-translational modification processes that may include, but are not limited to: glycosylation, proteolytic cleavage, lipidization, signal peptide cleavage, propeptide cleavage, phosphorylation, and such like. A peptide can be made using recombinant techniques, e.g., through the expression of a recombinant or synthetic polynucleotide. A recombinantly produced peptide it typically substantially free of culture medium, e.g., culture medium represents less than about 20%, more preferably less than about 10%, and most preferably less than about 5% of the volume of the protein preparation.

The term "protein" is used to describe a folded polypeptide having a secondary or tertiary structure. The protein may be composed of a single polypeptide, or may comprise multiple polypepties that are assembled to form a multimer. The multimer may be a homooligomer, or a heterooligmer. The protein may be a naturally occurring, or wild type protein, or a modified, or non-naturally, occurring protein. The protein may, for example, differ from a wild type protein by the addition, substitution or deletion of one or more amino acids.

A "variant" of a protein encompass peptides, oligopeptides, polypeptides, proteins and enzymes having amino acid substitutions, deletions and/or insertions relative to the unmodified or wild-type protein in question and having similar biological and functional activity as the unmodified protein from which they are derived. The term "amino acid identity" as used herein refers to the extent that sequences are identical on an amino acid-by-amino acid basis over a window of comparison. Thus, a "percentage of sequence identity" is calculated by comparing two optimally aligned sequences over the window of comparison, determining the number of positions at which the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

For all aspects and embodiments of the present invention, a "variant" has at least 50%, 60%, 70%, 80%, 90%, 95% or 99% complete sequence identity to the amino acid sequence of the corresponding wild-type protein. Sequence identity can also be to a fragment or portion of the full length polynucleotide or polypeptide. Hence, a sequence may have only 50% overall sequence identity with a full length reference sequence, but a sequence of a particular region, domain or subunit could share 80%, 90%, or as much as 99% sequence identity with the reference sequence.

The term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified", "mutant" or "variant" refers to a gene or gene product that displays modifications in sequence (e.g., substitutions, truncations, or insertions), post-translational modifications and/or functional properties (e.g., altered characteristics) when compared to the wild-type gene or gene product. It is noted that naturally occurring mutants can be isolated; these are identified by the fact that they have altered characteristics when compared to the wild-type gene or gene product. Methods for introducing or substituting naturally-occurring amino acids are well known in the art. For instance, methionine (M) may be substituted with arginine (R) by replacing the codon for methionine (ATG) with a codon for arginine (CGT) at the relevant position in a polynucleotide encoding the mutant monomer. Methods for introducing or substituting non-naturally-occurring amino acids are also well known in the art. For instance, non-naturally-occurring amino acids may be introduced by including synthetic aminoacyl-tRNAs in the IVTT system used to express the mutant monomer. Alternatively, they may be introduced by expressing the mutant monomer in *E. coli* that are auxotrophic for specific amino acids in the presence of synthetic (i.e. non-naturally-occurring) analogues of those specific amino acids. They may also be produced by naked ligation if the mutant monomer is produced using partial peptide synthesis. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid. Conservative amino acid changes are well-known in the art and may be selected in accordance with the properties of the 20 main amino acids as defined in Table 1 below. Where amino acids have similar polarity, this can also be determined by reference to the hydropathy scale for amino acid side chains in Table 2.

TABLE 1

| Chemical properties of amino acids | | | |
|---|---|---|---|
| Ala | aliphatic, hydrophobic, neutral | Met | hydrophobic, neutral |
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged(+) | Trp | aromatic, hydrophobic, neutral |
| Leu | aliphatic, hydrophobic, neutral | Tyr | aromatic, polar, hydrophobic |

TABLE 2

Hydropathy scale

| Side Chain | Hydropathy |
|---|---|
| Ile | 4.5 |
| Val | 4.2 |
| Leu | 3.8 |
| Phe | 2.8 |
| Cys | 2.5 |
| Met | 1.9 |
| Ala | 1.8 |
| Gly | −0.4 |
| Thr | −0.7 |
| Ser | −0.8 |
| Trp | −0.9 |
| Tyr | −1.3 |
| Pro | −1.6 |
| His | −3.2 |
| Glu | −3.5 |
| Gln | −3.5 |
| Asp | −3.5 |
| Asn | −3.5 |
| Lys | −3.9 |
| Arg | −4.5 |

A mutant or modified protein, monomer or peptide can also be chemically modified in any way and at any site. A mutant or modified monomer or peptide is preferably chemically modified by attachment of a molecule to one or more cysteines (cysteine linkage), attachment of a molecule to one or more lysines, attachment of a molecule to one or more non-natural amino acids, enzyme modification of an epitope or modification of a terminus. Suitable methods for carrying out such modifications are well-known in the art. The mutant of modified protein, monomer or peptide may be chemically modified by the attachment of any molecule. For instance, the mutant of modified protein, monomer or peptide may be chemically modified by attachment of a dye or a fluorophore.

Stalling Motor Proteins

The disclosure relates to method of loading a motor protein onto a polynucleotide adapter comprising a spacer, wherein a blocking moiety prevents the motor protein from moving off the spacer. As explained in more detail below, the method may reduce the rate at which the motor protein turns over fuel molecules compared to when the motor protein is bound to a polynucleotide.

As discussed above, methods for controlling the movement of a motor protein onto a target polynucleotide are known in the art. One method that is known in the art involves preventing the movement of a motor protein onto a target polynucleotide using a spacer. The method involves holding the motor protein at the spacer (e.g. abutting the spacer). The motor protein can be held in this way on, for example, a polynucleotide strand. The motor protein may be directional (i.e. process the polynucleotide in a 5'→3' or 3'→5' direction). By providing a spacer between the motor protein and the target polynucleotide in the direction that the motor protein processes, the movement of the motor protein can be constrained by the spacer. On the one hand, the movement of the motor protein onto the target polynucleotide is impeded by the spacer. On the other hand, the movement of the motor protein is also constrained by its directionality meaning that it may not move away from the spacer in the direction away from the target polynucleotide. In this way, a motor protein can be held at (e.g. abutting the spacer), because its movement either “forward” towards the spacer or “backwards” away from the spacer is constrained.

However, constraining a motor protein in this known way typically may not prevent the motor protein from consuming fuel (e.g. cofactors required for polynucleotide processing by the motor protein) which may be present in the reaction conditions. Without being bound by theory, stalling a motor protein at a spacer is believed to result in “slippage” of the motor protein. The motor protein is loaded onto the polynucleotide adapter and progresses until it reaches the spacer in the manner described above. The movement of the motor protein is stalled when it reaches the spacer. However, the motor protein does not remain stationary at the spacer. Rather, the motor protein is believed to periodically disengage from being bound to the polynucleotide adapter adjacent to the spacer, causing the motor protein to diffuse back along the polynucleotide adapter away from the spacer. The motor protein then re-engages with the polynucleotide adapter and progresses until it reaches the spacer again, following which the cycle is repeated. The successive disengagement of the motor protein from the polynucleotide adapter, re-engagement with the polynucleotide adapter and progression of the motor protein along the polynucleotide adapter to the spacer consumes fuel present in the system, despite being associated with no overall progress of the motor protein. This non-productive consumption of fuel by a motor protein which is stalled at a spacer is termed futile turnover.

Futile turnover is undesirable and decreases the overall efficiency of the system. For example, if a motor protein is stalled at a spacer in the manner described for a prolonged period of time, the quantity of fuel consumed by the motor protein in futile turnover can be significant. Such unproductive fuel use can significantly limit the lifetime of the system e.g. in storage. The decrease of fuel may for example also undesirably reduce the speed of the motor protein. Futile turnover may require the quantity of fuel in the reaction system being initially and undesirably increased to take account of this undesired consumption. The requirements for high purity fuel in order to avoid artefacts caused by impurities during the characterisation of the target polynucleotide means that futile turnover can significantly increase costs. Furthermore, if the motor protein is negatively affected by high concentrations of spent fuel molecules (i.e. fuel molecules which have been turned over by the motor protein such as ADP) then the control which the motor protein exerts on the target polynucleotide being characterised can be decreased and/or the speed of the motor protein can be undesirably decreased.

In seeking to address this it has been surprisingly found that futile turnover can be decreased or prevented by stalling the motor protein on a spacer. In particular, by preventing the movement of the motor protein off the spacer, futile turnover is reduced. In other words, the rate at which the motor protein turns over fuel molecules compared to when it is bound to a polynucleotide is reduced. Suitable spacers are described in more detail herein.

In developing the presently claimed methods it has surprisingly been found that a motor protein can be beneficially prevented from moving off a spacer comprised in a polynucleotide adapter by binding a blocking moiety to the polynucleotide adapter. The blocking moiety can for example sterically prevent the motor protein from moving off the spacer. The blocking moiety can chemically prevent the motor protein from moving off the spacer. Blocking moieties are described in more detail herein.

Accordingly provided herein is a method of loading a motor protein onto a polynucleotide adapter, the method comprising:

i) providing a polynucleotide adapter comprising a spacer;
ii) contacting the polynucleotide adapter with a motor protein; and
iii) positioning the motor protein on the spacer;
wherein a blocking moiety bound to the polynucleotide adapter prevents the motor protein from moving off the spacer.

In one embodiment, provided herein is a method of loading a motor protein onto a polynucleotide adapter, the method comprising:

i) providing a polynucleotide adapter comprising a spacer;
ii) contacting the polynucleotide adapter with a motor protein;
iii) causing the motor protein to progress onto the spacer; and
iv) binding a blocking moiety to the polynucleotide adapter, wherein the blocking moiety prevents the motor protein from moving off the spacer.

In some embodiments, the polynucleotide comprises a loading site connected to a spacer. In some embodiments, the loading site may be contacted with a motor protein. Contacting the loading site with a motor protein causes the motor protein to progress from the loading site onto the spacer. In embodiments in which the polynucleotide adapter comprises a loading site, binding a blocking moiety to the polynucleotide adapter typically prevents the motor protein from moving off the spacer and onto the loading site. Loading sites are described in more detail herein.

Accordingly, in some embodiments, the provided methods comprise (i) contacting the loading site with a motor protein, wherein the motor protein engages with the loading site; and (ii) binding a blocking moiety to the polynucleotide adapter, wherein the blocking moiety prevents the motor protein from moving off the spacer and re-engaging with the loading site.

In other embodiments, the polynucleotide adapter does not comprise a loading site. In such embodiments the motor protein is typically contacted with the polynucleotide adapter e.g. at the spacer; i.e the motor protein may be contacted with the spacer. The motor protein is positioned on the spacer. The motor protein may be positioned on the spacer by any suitable means. For example, as described in more detail herein, the motor protein may be contacted with the spacer and subsequently the motor protein may be modified in order to prevent the motor protein from disengaging from the spacer. The spacer may be flanked by a blocking moiety to prevent the motor protein from moving off the spacer. The spacer may in some embodiments comprise natural nucleotides in addition to spacer units. This is described in more detail herein.

Polynucleotide Adapter

The provided methods comprise loading a motor protein onto a polynucleotide adapter. WO 2015/110813 describes the loading of motor proteins onto a target polynucleotide such as an adapter, and is hereby incorporated by reference in its entirety.

An adapter typically comprises a polynucleotide strand capable of being attached to the end of a target polynucleotide. The target polynucleotide is typically intended for characterisation in accordance with methods disclosed herein.

The polynucleotide adapter may be added to both ends of the target polynucleotide. Alternatively, different adapters may be added to the two ends of the target polynucleotide. An adapter may be added to just one end of the target polynucleotide. Methods of adding adapters to polynucleotides are known in the art. Adapters may be attached to polynucleotides, for example, by ligation, by click chemistry, by tagmentation, by topoisomerisation or by any other suitable method.

In one embodiment, the adapter is synthetic or artificial. Typically, the adapter comprises a polymer as described herein. The adapter comprises a spacer as described herein. As explained in more detail below, the adapter may also comprise a loading site, e.g. a loading site connected to a spacer. Loading sites are described in more detail herein.

In some embodiments, the adapter comprises a polynucleotide. For example, as explained below, the loading site may comprise a single-stranded polynucleotide strand. The polynucleotide adapter may comprise DNA, RNA, modified DNA (such as a basic DNA), RNA, PNA, LNA, BNA and/or PEG. Usually, the adapter comprises single stranded and/or double stranded DNA or RNA.

In one embodiment, the adapter is a Y adapter. A Y adapter is typically a polynucleotide adapter. A Y adapter is typically double stranded and comprises (a) at one end, a region where the two strands are hybridised together and (b), at the other end, a region where the two strands are not complementary. The non-complementary parts of the strands form overhangs. The presence of a non-complementary region in the Y adapter gives the adapter its Y shape since the two strands typically do not hybridise to each other unlike the double stranded portion. As explained in more detail below, in one embodiment a motor protein may bind to an overhang of an adapter such as a Y adapter. In another embodiment, a motor protein may bind to the double stranded region. In other embodiments, a motor protein may bind to a single-stranded and/or a double-stranded region of the adapter. In other embodiments, a first motor protein may bind to the single-stranded region of such an adapter and a second motor protein may bind to the double-stranded region of the adapter.

In one embodiment the adapter comprises a membrane anchor or a pore anchor as described in more detail herein. In some embodiments, the anchor may be attached to a polynucleotide that is complementary to and hence that is hybridised to the overhang to which an nucleic acid handling enzyme is bound.

In some embodiments, one of the non-complementary strands of a polynucleotide adapter such as a Y adapter may comprise a leader sequence, which when contacted with a transmembrane pore is capable of threading into a nanopore. In one embodiment, the leader sequence may comprise a loading site as described in more detail herein. In one embodiment the leader sequence may precede the loading site (i.e. the adapter may comprise a leader sequence connected to a loading site, the loading site being connected to the spacer, such that the loading site is located between the leader sequence and the spacer). In one embodiment, the loading site may precede the leader sequence (i.e. the adapter may comprise a loading site connected to a leader sequence, the leader sequence being connected to the spacer, such that the leader sequence is located between the loading site and the spacer).

The leader sequence typically comprises a polymer such as a polynucleotide, for instance DNA or RNA, a modified polynucleotide (such as abasic DNA), PNA, LNA, polyethylene glycol (PEG) or a polypeptide. In some embodiments, the leader sequence comprises a single strand of DNA, such as a poly dT section. The leader sequence can be any length, but is typically 10 to 150 nucleotides in length, such as from 20 to 120, 30 to 100, 40 to 80 or 50 to 70 nucleotides in length.

In one embodiment, the polynucleotide adapter is a hairpin loop adapter. A hairpin loop adapter is an adapter comprising a single polynucleotide strand, wherein the ends of the polynucleotide strand are capable of hybridising to each other, or are hybridized to each other, and wherein the middle section of the polynucleotide forms a loop. Suitable hairpin loop adapters can be designed using methods known in the art.

As explained in more detail below, a polynucleotide adapter can be attached to a target polynucleotide in order to characterise the target polynucleotide.

Those skilled in the art will appreciate that the adapters described for use in the methods provided herein thus reduce futile turnover by a motor protein stalled thereon compared to adapters lacking a blocking moiety as described herein. Typically, the adapters described for use in the methods provided herein improve the efficiency of fuel usage compared to adapters lacking a blocking moiety as provided herein.

Those skilled in the art will also appreciate that when the adapter comprises a polynucleotide strand, the sequence of the adapter is typically not determinative and can be controlled or chosen according to the motor protein and other experimental conditions such as any polynucleotide to be characterised. Exemplary sequences are provided solely by way of illustration in the examples. For example, the adapter may comprise a sequence such as SEQ ID NO: 13 or a polynucleotide sequence having at least 20%, such as at least 30%, e.g. at least 40% such as at least 50%, e.g. at least 60% such as at least 70%, e.g. at least 80%, for example at least 90% e.g. at least 95% sequence similarity or identity to SEQ ID NO: 13. The adapter may comprise a spacer as described herein flanked by sequences such as those provided in SEQ ID NOs: 14 and 15, or polynucleotide sequences independently having at least 20%, such as at least 30%, e.g. at least 40% such as at least 50%, e.g. at least 60% such as at least 70%, e.g. at least 80%, for example at least 90% e.g. at least 95% sequence similarity or identity to SEQ ID NOs: 14 and 15. Those skilled in the art will appreciate that SEQ ID NO: 14 comprises a sequence such as SEQ ID NO: 15 and the adapter may thus comprise a polynucleotide sequence such as SEQ ID NO: 15 or a polynucleotide sequence having at least 20%, such as at least 30%, e.g. at least 40% such as at least 50%, e.g. at least 60% such as at least 70%, e.g. at least 80%, for example at least 90% e.g. at least 95% sequence similarity or identity to SEQ ID NO: 15. The sequence of the adapter can typically be altered without negatively affecting the reduction in futile turnover provided by a given spacer.

Spacer(s)

The disclosed method comprise loading a motor protein onto a polynucleotide adapter comprising a spacer. One or more spacers may be present in the polynucleotide adapter. For example, the polynucleotide adapter may comprise from one to about 10 spacers, e.g. from 1 to about 5 spacers, e.g. 1, 2, 3, 4 or 5 spacers. The term "spacer" and "stalling site" may be used interchangeably and refer to a portion of the polynucleotide adapter which stalls the motor protein, typically preventing futile turnover as described above. The spacer (stalling site) may comprise any suitable number of spacer units. Suitable spacer units are described herein and include abasic nucleotides and spacer groups such as iSp9, iSp18, and C3 groups (described below). The spacer (stalling site) may comprise nucleotide units in addition to spacer units. For example, as described in more detail herein, the spacer (stalling site) may comprise spacer units interspaced by one or more nucleotides. The spacer (stalling site) may comprise one or more spacer units flanked or separated by one or more nucleotide units, such as one or more polynucleotides. This concept is sometimes referred to as "nucleotide islands" and is discussed further below.

The one or more spacers are included in the polynucleotide adapter. Typically the polynucleotide adapter may comprise strands of single stranded and/or double stranded polynucleotides and the one or more spacers may be comprised in the polynucleotide strands, e.g. interrupting a strand or separating one strand from another. Exemplary polynucleotide adapters are described in more detail herein.

Each spacer in the polynucleotide adapter provides an energy barrier which impedes movement of the motor protein. For example, a spacer may stall the motor protein by reducing the traction of the motor protein. This may be achieved for instance by using an abasic spacer i.e. a spacer in which the bases are removed from one or more nucleotides in the polynucleotide adapter. A spacer may physically block movement of the motor protein, for instance by introducing a bulky chemical group to physically impede the movement of the motor protein.

A spacer may comprise any molecule or combination of molecules that stalls the one or more motor protein(s). A spacer may comprise any molecule or combination of molecules that prevents the motor protein from moving along the target polynucleotide. It is straightforward to determine whether or not the motor protein is stalled at a spacer. For example, this can be assayed as discussed in WO 2014/135838, the contents of which are incorporated by reference—for instance, the ability of a motor protein to move past a spacer and displace a complementary strand of DNA can be measured by PAGE.

In some embodiments, a spacer may comprise a linear molecule, such as a polymer. Typically, such a spacer has a different structure from the target polynucleotide. For instance, if the target polynucleotide is DNA, the or each spacer typically does not comprise DNA. In particular, if the target polynucleotide is deoxyribonucleic acid (DNA) or ribonucleic acid (RNA), the or each spacer preferably comprises peptide nucleic acid (PNA), glycerol nucleic acid (GNA), threose nucleic acid (TNA), locked nucleic acid (LNA), bridged nucleic acid (BNA) or a synthetic polymer with nucleotide side chains.

In some embodiments, a spacer may comprise one or more nitroindoles, one or more inosines, one or more acridines, one or more 2-aminopurines, one or more 2-6-diaminopurines, one or more 5-bromo-deoxyuridines, one or more inverted thymidines (inverted dTs), one or more inverted dideoxy-thymidines (ddTs), one or more dideoxy-cytidines (ddCs), one or more 5-methylcytidines, one or more 5-hydroxymethylcytidines, one or more 2'-O-Methyl RNA bases, one or more Iso-deoxycytidines (Iso-dCs), one or more Iso-deoxyguanosines (Iso-dGs), one or more C3 ($OC_3H_6OPO_3$) groups, one or more photo-cleavable (PC) [$OC_3H_6$—C(O)NHCH$_2$—$C_6H_3NO_2$—CH(CH$_3$)OPO$_3$] groups, one or more hexandiol groups, one or more spacer 9 (iSp9) [$(OCH_2CH_2)_3OPO_3$] groups, or one or more spacer 18 (iSp18) [$(OCH_2CH_2)_6OPO_3$] groups; or one or more thiol connections. A spacer may comprise any combination of these groups. Many of these groups are commercially available from IDT® (Integrated DNA Technologies®). For example, C3, iSp9 and iSp18 spacers are all available from IDT®.

A spacer may comprise any number of the above groups as spacer units. For instance, a spacer may comprise from 1 to about 12 or more (e.g. from about 1 to about 8, for instance from 1 to about 6 such as from 1 to about 4) spacers selected from 2-aminopurines, 2-6-diaminopurines, 5-bromo-deoxyuridines, inverted dTs, ddTs, ddCs, 5-methylcytidines, 5-hydroxymethylcytidines, 2'-O-Methyl RNA bases, Iso-dCs, Iso-dGs, iSpC3 groups, PC groups, hexandiol groups and thiol connections. A spacer may for instance comprise 2, 3, 4, 5, 6, 7, 8, 9, 10, 11, or 12 of such groups.

A spacer may comprise from 1 to about 12 or more (e.g. from about 1 to about 8, for instance from 1 to about 6 such as from 1 to about 4) C3 groups; for instance a spacer may comprise 2, 3, 4, 5, 6, 7, 8, 9, 10, 11, or 12 C3 groups. A C3 group is typically a —$OC_3H_6OPO_3$— group.

A spacer may comprise from about 1 to about 8 or more (e.g. from about 1 to about 6 such as from 1 to about 4) iSp9 groups; for instance a spacer may comprise 2, 3, 4, 5, 6, 7 or 8 iSp9 groups. An iSp9 group is typically a —$(OCH_2CH_2)_3OPO_3$— group.

A spacer may comprise from about 1 to about 8 or more (e.g. from about 1 to about 6 such as from 1 to about 4) iSp18 groups; for instance a spacer may comprise 2, 3, 4, 5, 6, 7 or 8 iSp9 groups. An iSp18 group is typically a —$(OCH_2CH_2)_6OPO_3$— group. In one embodiment the spacer comprises 4 iSp18 groups.

In some embodiments, the spacer comprises one or more iSp18 group(s) and/or one ore more iSp9 group(s) and/or one or more C3 group(s).

In some embodiments, a spacer may comprise one or more chemical groups which cause the motor protein to stall. In some embodiments, suitable chemical groups are one or more pendant chemical groups. The one or more chemical groups may be attached to one or more nucleobases in the polynucleotide adapter. The one or more chemical groups may be attached to the backbone of the polynucleotide adapter. Any number of appropriate chemical groups may be present, such as 2, 3, 4, 5, 6, 7, 8, 9, 10, 11, 12 or more. Suitable groups include, but are not limited to, fluorophores, streptavidin and/or biotin, cholesterol, methylene blue, dinitrophenols (DNPs), digoxigenin and/or anti-digoxigenin and dibenzylcyclooctyne groups.

In some embodiments, a spacer may comprise a polymer. In some embodiments the spacer may comprise a polymer which is a polypeptide or a polyethylene glycol (PEG).

When the spacer comprises a polypeptide, the polypeptide may comprise any number of amino acids. For example, the polypeptide may comprise from about 1 to about 12 or more (e.g. from about 1 to about 8, for instance from 1 to about 6 such as from 1 to about 4) amino acids; for instance a spacer may comprise 2, 3, 4, 5, 6, 7, 8, 9, 10, 11, or 12 amino acids.

When the spacer comprises a polymer such as PEG (polyethylene glycol), the polymer may comprise any number of monomer units. For example, the polymer may comprise from about 1 to about 12 or more (e.g. from about 1 to about 8, for instance from 1 to about 6 such as from 1 to about 4) monomer units; for instance a spacer may comprise 2, 3, 4, 5, 6, 7, 8, 9, 10, 11, or 12 monomer (e.g. PEG) units.

In some embodiments, a spacer may comprise one or more abasic nucleotides (i.e. nucleotides lacking a nucleobase), such as 2, 3, 4, 5, 6, 7, 8, 9, 10, 11, 12 or more abasic nucleotides. The nucleobase can be replaced by —H (idSp) or —OH in the abasic nucleotide. Abasic spacers can be inserted into target polynucleotides by removing the nucleobases from one or more adjacent nucleotides. For instance, polunucleotides may be modified to include 3-methyladenine, 7-methylguanine, 1,N6-ethenoadenine inosine or hypoxanthine and the nucleobases may be removed from these nucleotides using Human Alkyladenine DNA Glycosylase (hAAG). Alternatively, polunucleotides may be modified to include uracil and the nucleobases removed with Uracil-DNA Glycosylase (UDG). In one embodiment, the one or more spacers do not comprise any abasic nucleotides.

In some embodiments, the spacer may comprise one or more nucleotide units, also referred to as nucleotide islands. The spacer typically does not comprise a polynucleotide strand sufficiently long to fully occupy the active site of the motor protein. For example, in embodiments in which the spacer comprises one or more nucleotide units, the spacer typically comprises from 1 to 3 nucleotides, more often from 1 to 2 nucleotides. In some embodiments the spacer comprises from 1 to 3 contiguous nucleotides in the or each nucleotide island present in the spacer. In some embodiments a spacer may comprise from 1 to 5 nucleotide islands, e.g. 1, 2 or 3 nucleotide islands each comprising from 1 to 3 contiguous nucleotides. Those skilled in the art will recognise that the active site (polynucleotide-binding cleft) of motor proteins is typically of size corresponding to around 8 nucleotide units. As such, in embodiments in which the spacer comprises from 1 to 3, e.g. from 1 to 2 nucleotide spacer units, the nucleotide spacer units do not fully occupy the active site of the motor protein. In some embodiments, exemplary spacers (stalling sites) which comprise from 1 to 3, e.g. from 1 to 2 nucleotides typically comprise one or more moieties selected from $—[(S)_x—(N)_y—(S)_z]_w—$ wherein each S is a spacer unit (e.g. a spacer unit described herein); each N is a nucleotide; x is an integer from 1 to 7; y is an integer from 1 to 3, typically 1 or 2; z is an integer from 1 to 7 and w is an integer from 1 to 3; and wherein each S is the same or different and each N is the same or different. More often in such embodiments, each S is a spacer unit independently selected from C3, iSp9 and iSp18 spacer units; each N is independently selected from adenine, cytosine, guanine, and thymine; x is an integer from 1 to 7; y is 1 or 2; z is an integer from 1 to 4 and w is an integer from 1 to 3.

In some embodiments the spacer may comprise one or more nucleotide islands and the adapter may have a blocking moiety as defined herein bound thereto prior to the contacting of the motor protein with the adapter. In such embodiments the motor protein may thus directly load onto the spacer. The motor protein may be loaded onto a nucleotide island comprised within the spacer. The motor protein may be loaded onto a nucleotide island comprised with in the spacer and then be modified to prevent the motor protein from leaving the spacer, e.g. by dissociating from the spacer. Modification of motor proteins is described in more detail herein. In some embodiments the motor protein may be loaded onto a nucleotide island and then progress onto spacer units comprised in the spacer. In some embodiments the motor protein may remain located at the nucleotide island(s) in the spacer until a force is applied to move the motor protein off the islands. In some embodiments the force is provided by a nanopore as described herein.

In some embodiments the spacer may comprise one or more moieties selected from: —S—N—N—S—S—; —S—N—S—N—S—; —S—S—N—N—S—; —S—S—N—S—S—; —N—N—S—N—N—S—; —S—S—N—N—S—S—; —S—N—N—S—N—N—S—; —S—N—S—N—S—N—S—; —S—S—S—S—S—S—S—; —S—S—N—N—S—N—N—S—; —S—S—S—S—N—N—S—S—; —S—N—N—S—S—N—N—S—S—; —S—S—N—N—N—S—N—N—S—; —S—S—N—N—S—N—N—N—S—; —S—S—N—N—S—N—N—S—S—; —S—S—S—N—N—N—S—N—S—; —S—S—S—N—S—N—N—N—S—; —S—S—S—S—N—N—S—N—S—; —S—S—S—S—N—S—N—N—S—; —S—N—N—S—N—N—S—N—N—S—; —S—S—S—N—N—S—N—N—S—S—; —S—S—S—N—N—S—S—N—N—S—; —S—S—S—S—S—S—N—N—S—S—; —N—N—S—N—N—S—S—S—S—S—S—; —N—N—S—S—N—N—S—S—S—S—S—; —N—N—S—S—S—N—N—S—S—S—S—; —N—N—S—S—S—S—N—N—S—S—S—; —N—N—S—S—S—S—S—N—N—S—S—; —N—N—S—S—S—S—S—S—N—N—S—; —S—N—N—S—N—N—S—S—S—S—S—; —S—N—N—S—S—N—N—S—S—S—S—; —S—N—N—S—S—S—N—N—S—S—S—; —S—N—N—S—S—S—S—N—N—S—S—; —S—N—N—S—S—S—S—S—N—N—S—; —S—S—N—N—S—N—N—S—S—S—S—; —S—S—N—N—S—S—N—N—S—S—S—; —S—S—N—N—S—S—S—N—N—S—S—; —S—S—N—N—S—S—S—S—N—N—S—; —S—S—S—N—N—S—N—N—S—S—S—; —S—S—S—N—N—S—S—N—N—S—S—; —S—S—S—S—N—N—S—N—N—S—S—; —S—S—S—S—N—N—S—S—N—N—S—; —S—S—S—S—S—N—N—S—N—N—S—; —S—S—S—N—N—S—N—N—S—N—N—S—; —S—S—S—N—N—S—N—N—S—S—S—S—; —S—S—S—N—N—S—S—N—N—S—S—S—; —S—S—S—N—N—S—S—S—S—N—N—S—; —S—S—S—N—N—S—N—N—S—S—N—N—S—; —S—S—S—N—N—S—S—N—N—S—S—S—S—; —S—S—S—S—S—N—N—S—N—N—S—S—S—; —S—S—S—N—N—S—S—N—N—S—S—S—S—S—; —S—S—S—N—N—S—S—S—S—S—S—N—N—S—; —S—S—S—S—S—N—N—S—N—N—S—N—N—S—; —S—S—S—N—N—S—S—N—N—S—S—S—S—S—S—; —S—S—S—S—S—N—N—S—N—N—S—S—N—N—S—; —S—S—S—N—N—S—S—N—N—S—S—S—S—S—S—S—; —S—S—S—N—N—S—S—N—N—S—S—S—S—S—S—S—S—; etc; wherein each S is a spacer unit as described herein and each N is a nucleotide.

In some embodiments the spacer may comprise one or more moieties selected from: —S—N—S—N—S—N—S—; —S—N—N—S—N—N—S—N—N—S—; —S—S—S—S—S—S—N—N—S—S—; —S—S—S—S—S—N—N—S—N—N—S—S—S—; —S—S—S—N—N—S—N—N—S—S—N—N—S—; —S—S—S—S—S—N—N—S—N—N—S—S—N—N—S—; —S—S—S—N—N—S—N—N—S—N—N—S—; —N—N—S—S—N—N—S—S—S—S—S—; —S—N—N—S—S—N—N—S—S—S—S—; —S—S—N—N—S—S—N—N—S—S—S—; —S—S—S—S—N—N—S—S—N—N—S—; —N—N—S—N—N—S—S—S—S—S—S—; —S—N—N—S—N—N—S—S—S—S—S—; —S—S—N—N—S—N—N—S—S—S—S—; —S—S—S—N—N—S—N—N—S—S—S—: —S—S—S—S—N—N—S—N—N—S—S—; —S—S—S—N—N—S—S—N—N—S—; etc; wherein each S is a spacer unit as described herein and each N is a nucleotide.

In some embodiments the spacer may comprise one or more moieties selected from: —S—N—N—S—N—N—S—N—N—S—; —S—S—S—S—S—N—N—S—N—N—S—S—S—; —N—N—S—S—N—N—S—S—S—S—S—; —S—N—N—S—S—N—N—S—S—S—S—; —S—S—N—N—S—S—N—N—S—S—S—; —S—S—S—S—N—N—S—S—N—N—S—; —S—S—N—N—S—N—N—S—S—S—S—; —S—S—S—N—N—S—N—N—S—S—S—: —S—S—S—S—N—N—S—N—N—S—S—; —S—S—S—N—N—S—S—N—N—S—; etc; wherein each S is a spacer unit as described herein and each N is a nucleotide.

In some embodiments the spacer may comprise one or more moieties selected from: —S—S—S—S—S—N—N—S—N—N—S—S—S—; —N—N—S—S—N—N—S—S—S—S—S—; —S—N—N—S—S—N—N—S—S—S—S—; —S—S—N—N—S—S—N—N—S—S—S—; —S—S—S—S—N—N—S—S—N—N—S—; —S—S—S—N—N—S—S—N—N—S—; etc; wherein each S is a spacer unit as described herein and each N is a nucleotide.

In some embodiments the spacer may comprise one or more moieties selected from: —S—S—N—N—S—S—; —S—N—S—N—S—N—S; —S—N—N—S—N—N—S—N—N—S—; —S—S—S—S—N—N—S—S—; —S—S—S—S—S—S—N—N—S—S—; —S—S—S—N—N—S—N—N—S—N—N—S—; —S—S—S—S—S—N—N—S—N—N—S—N—N—S—; S—S—S—N—N—S—N—N—S—S—S—; —S—S—S—S—S—N—N—S—N—N—S—S—S—; —S—S—S—N—N—S—N—N—S—S—N—N—S—; and —S—S—S—S—S—N—N—S—N—N—S—S—N—N—S—; etc; wherein each S is a spacer unit as described herein and each N is a nucleotide. In some embodiments, each S is the same spacer unit. In some embodiments, the S groups are different spacer units.

In some embodiments a spacer may comprise both nucleotide based spacer units (e.g. modified nucleotides such as, 2'-O-Methyl RNA bases) and non-nucleotide based spacer units (such as iSp18, iSp9 and C3 spacer units). In some embodiments each S is independently selected from iSp18 groups, iSp9 groups, 2'-O-Methyl uridine and C3 groups. In some embodiments each S is independently selected from iSp18 groups, iSp9 groups and C3 groups. In some embodiments each S independently is selected from iSp18 groups, 2'-O-Methyl uridine and C3 groups. In some embodiments each S independently is selected from iSp18 groups and C3 groups. In some embodiments each N is the same nucleotide. In some embodiments, the N groups in the above moieties are different. In some embodiments each N group is independently selected from adenine, cytosine, guanine, and thymine. In some embodiments each N group is independently selected from cytosine and thymine. In some embodiments each N group is a thymine group.

In some embodiments, the spacer may comprise one or more moieties selected from: -8-T-T-9-T-T-8-; -8-T-8-T-8-T-8-; -8-T-T-8-T-T-8-T-T-8-; -3-3-8-8-T-T-8-8-; -3-3-3-3-8-8-T-T-8-8-; -3-3-3-3-8-T-T-8-T-T-8-3-8-; -3-3-8-T-T-8-T-T-8-3-T-T-8-; -3-3-3-3-8-T-T-8-T-T-8-3-T-T-8-; -3-3-3-T-T-8-T-T-8-T-T-8-; -3-3-3-T-T-8-T-T-8-; -3-T-T-8-T-T-8-T-T-8-; -T-T-3-3-T-T-3-3-3-3-8-; -3-T-T-3-3-T-T-3-3-3-8-; -3-3-T-T-3-3-T-T-3-3-8-; -3-3-3-3-T-T-3-3-T-T-8-; -T-T-3-3-3-T-T-3-3-3-8-; -T-T-8-T-T-3-3-3-3-3-8-; -3-T-T-8-T-T-3-3-3-3-8-; -3-3-T-T-8-T-T-3-3-3-8-; -3-3-3-T-T-8-T-T-3-3-8-; -3-3-3-3-T-T-8-T-T-3-8-; -3-3-3-T-T-3-3-T-T-9-; -3-3-3-T-T-mU-mU-mU-T-T-8-; -3-3-3-T-T-mU-mU-T-T-8-; wherein 3 is first spacer and 8 is a second spacer and 9 is a third spacer and mU is a fourth spacer; typically wherein 3 is a C3 spacer as defined herein and 8 is an iSp18 spacer as defined herein and 9 is an iSp9 spacer as defined herein and mU is 2'-O-Methyl uridine; and each N is independently selected from adenine, cytosine, guanine, and thymine; preferably thymine.

In some embodiments, the spacer may comprise one or more moieties selected from: -8-8-N—N-8-8-; -8-N-8-N-8-N-8; -8-N—N-8-N—N-8-N—N-8-; -3-3-8-8-N—N-8-8-; -3-3-3-3-8-8-N—N-8-8-; -3-3-8-N—N-8-N—N-8-N—N-8-; -3-3-3-3-8-N—N-8-N—N-8-N—N-8-; 3-3-8-N—N-8-N—N-8-3-8-; -3-3-3-3-8-N—N-8-N—N-8-3-8-; -3-3-8-N—N-8-N—N-8-3-N—N-8-; and -3-3-3-3-8-N—N-8-N—N-8-3-N—N-8-; wherein 3 is first spacer and 8 is a second spacer; typically wherein 3 is a C3 spacer as defined herein and 8 is an iSp18 or iSp9 spacer as defined herein, typically 8 is an iSp18 spacer as defined herein; and each N is independently selected from adenine, cytosine, guanine, and thymine; preferably thymine.

In some embodiments the spacer may comprise one or more moieties selected from: 88TTT88; 88mUmUmU88; 88/iBNA-T//iBNA-T//iBNA-T/88; 88T88; 8TT88; 88TT8; 8T8T8; 99TT9TT99; 8TT9TT8; 8TT3TT8; 8T8T8T8; 8TT8TT8TT8; 3388TT88; 333388TT88; 338TT8TT8TT8; 33338TT8TT8TT8; 338TT8TT838; 33338TT8TT838; 338TT8TT83TT8; 33338TT8TT83TT8; 8TT8TT8; TT8TT8; 3TT8TT8; 333TT8TT8TT8; 333TT8TT8; 3TT8TT8TT8; 33TT8TT8; 333TT8TT838; 33338TT8TT8; 333TT333333TT8; 333TT99TT8; 333TT9TT8; 333TT3TT8; 9TT8TT8; 99TT8TT8; 3333T8TT8; 3333TT8T8; 333T8TTT8; 333TTT8T8; 33TTT8TT8; 33TT8TTT8; 9TT99TT99; 333TT8TT9999; 333TT8TT999; 333TT8TT99; 333TT8TT9; TT3TT333338; 3TT3TT33338; 33TT3TT3338; 333TT3TT338; 3333TT3TT38; 33333TT3TT8; TT33TT33338; 3TT33TT3338; 33TT33TT338; 333TT33TT38; 3333TT33TT8; TT333TT3338; 3TT333TT338; 33TT333TT38; 333TT333TT8; TT3333TT338; 3TT3333TT38; 33TT3333TT8; TT33333TT38; 3TT33333TT8; TT333333TT8; TT8TT333338; 3TT8TT33338; 33TT8TT3338; 333TT8TT338; 3333TT8TT38; 33333TT8TT8; 333TT33TT8; 333TT33TT9; 333TTmUmUmUTT8; 333TTSpSpTT8; 333TTSpTT8; 9TT33TT99; 333TTmUmUTT8; 333TTrUTT8; 333TTrUrUTT8; 333TTrUrUrUTT8; 333TTrUrUrUrUTT8; 333TT33TTC12; 333TT33TTC6; mUmUmUTTmUmUTT8; mUmUmUTT33TT8; 333TT33TT88; 333TT33TT888; 333TT33TT8888; 333TT33TT99; 333TT33TT999; 333TT33TT9999; 333TT33TT333; 333TT33TT3333; 333TT33TT33333; 333TT33TT333333; 333TT33TT3333333; and 333TT33TT33333333.

In some embodiments the spacer may comprise one or more moieties selected from: 88mUmUmU88; 88/iBNA-T//iBNA-T//iBNA-T/88; 88T88; 88TT88; 8TT88; 88TT8; 8T8T8; 8TT9TT8; 8TT3TT8; 8T8T8T8; 8TT8TT8TT8; 3388TT88; 333388TT88; 33338TT8TT838; 338TT8TT83TT8; 33338TT8TT83TT8; 8TT8TT8; TT8TT8; 3TT8TT8; 333TT8TT8TT8; 333TT8TT8; 3TT8TT8TT8; TT3TT333338; 3TT3TT33338; 33TT3TT3338; 333TT3TT338; 3333TT3TT38; 33333TT3TT8; TT33TT33338; 3TT33TT3338; 33TT33TT338; 3333TT33TT8; TT333TT3338; 3TT333TT338; 33TT333TT38; TT3333TT338; 3TT3333TT38; 33TT3333TT8; TT33333TT38; 3TT33333TT8; TT333333TT8; TT8TT333338; 3TT8TT33338; 33TT8TT3338; 333TT8TT338; 3333TT8TT38; 33333TT8TT8; 333TT33TT9; 333TTmUmUmUTT8; 333TTSpSpTT8; 333TTSpTT8; 333TTmUmUTT8; and 333TT33TT8.

In some embodiments, the spacer may comprise one or more moieties selected from: -8-8-T-T-8-8-; -8-T-8-T-8-T-8; -8-T-T-8-T-T-8-T-T-8-; -3-3-8-8-T-T-8-8-; -3-3-3-3-8-8-T-T-8-8-; -3-3-8-T-T-8-T-T-8-T-T-8-; -3-3-3-3-8-T-T-8-T-T-8-T-T-8-; 3-3-8-T-T-8-T-T-8-3-8-; -3-3-3-3-8-T-T-8-T-T-8-3-8-; -3-3-8-T-T-8-T-T-8-3-T-T-8-; and -3-3-3-3-8-T-T-8-T-T-8-3-T-T-8-; wherein 3 is first spacer and 8 is a second spacer; typically wherein 3 is a C3 spacer as defined herein and 8 is an iSp18 or iSp9 spacer as defined herein, typically 8 is an iSp18 spacer as defined herein; and each T is thymine.

In some embodiments, the polynucleotide adapter comprises more than one spacer. Ins such embodiments, the two or more spacers may be the same or different. For example, one spacer may comprise one of the linear molecules discussed herein and another spacer may comprise one or more chemical groups which physically cause the one or more motor proteins to stall. A spacer may comprise any of the linear molecules discussed herein and one or more chemical groups which physically cause the one or more motor proteins to stall, such as one or more abasics and a fluorophore.

Suitable spacers can be designed or selected depending on the nature of the polynucleotide adapter, the motor protein and the conditions under which the method is to be carried out. For example, many motor proteins process DNA in vivo and such motor proteins may typically be stalled using anything that is not DNA.

Characterisation of a target polynucleotide is often carried out in the presence of free nucleotides and/or fuel molecules (cofactors for the motor protein). In the disclosed methods the motor protein is typically prevented from moving off the spacer in the presence of free nucleotides and/or fuel molecules (cofactors for the motor protein). If the polynucleotide adapter is to be used in methods which do not involve the presence of free nucleotides and/or fuel molecules, the motor protein is typically prevented from moving off the spacer in the absence of free nucleotides and/or fuel molecules. Different spacers may be used in these embodiments. For example, in embodiments wherein free nucleotides and/or fuel molecules are present, a longer spacer may beneficially be used compared to embodiments wherein free nucleotides and/or fuel molecules are not present.

In some embodiments, it is beneficial to design or select a suitable spacer for use in accordance with the disclosed methods according to the salt concentration that is present in the reaction conditions. For example, methods comprising characterisation of a target polynucleotide strand by moving the polynucleotide strand with respect to a nanopore often involve the use of relatively high salt concentrations. The salt concentration may affect the ability of the one or more spacers to stall the one or more motor proteins. In general, the higher the salt concentration used in the method of the invention, the shorter the one or more spacers that are typically used and vice versa.

Some particular combinations of features are shown in Table 1 below.

| Target polynucleotide | Spacer composition* | Spacer length (i.e. number of *) | Salt concentration | Free nucleotides? | Motor protein cofactor? |
|---|---|---|---|---|---|
| DNA | iSpC3 | 4 | 1M | Yes | Yes |
| DNA | iSp18 | 4 | 100-1000 mM | Yes | Yes |
| DNA | iSp18 | 6 | <100-1000 mM | Yes | Yes |
| DNA | iSp18 | 2 | 1M | Yes | Yes |
| DNA | iSpC3 | 12 | <100-1000 mM | Yes | Yes |
| DNA | iSpC3 | 20 | <100-1000 mM | Yes | Yes |
| DNA | iSp9 | 6 | 100-1000 mM | Yes | Yes |
| DNA | idSp | 4 | 1M | Yes | Yes |

In embodiments which involve the use of multiple motor proteins, a longer spacer can be beneficial. For example, in embodiments that involve the use of two motor proteins as described herein, a suitable spacer may comprise from about 1 to about 25 of the above-mentioned spacers (e.g. from about 1 to about 25 groups selected from iSp18 groups, iSp9 groups and C3 groups).

Blocking Moieties

In some embodiments, the disclosed methods involve binding a blocking moiety to the polynucleotide adapter. The blocking moiety prevents the motor protein from moving off the spacer of the polynucleotide adapter.

A blocking moiety is typically a moiety which prevents the movement of the motor protein in the direction opposite to that in which the motor protein naturally processes a polynucleotide. For example, if the motor protein naturally processes a polynucleotide strand in the 5' to 3' direction, then a suitable blocking moiety is in some embodiments a moiety which prevents the motor protein from moving in the 3' to 5' direction. Similarly, if the motor protein naturally processes a polynucleotide strand in the 3' to 5' direction, then a suitable blocking moiety is in some embodiments a moiety which prevents the motor protein from moving in the 5' to 3' direction.

In the disclosed methods, the blocking moiety is bound to the polynucleotide adapter so as to prevent the movement of the motor protein off the spacer. Preventing the movement of the motor protein from off the spacer can be achieved by providing a steric block to physically prevent the movement of the motor protein. Preventing the movement of the motor protein from off the spacer can be achieved by using a chemical blocking moiety over or past which the motor protein cannot move. In some embodiments, the blocking moiety comprises one or more of the spacer groups discussed herein. In other embodiments, the blocking moiety may comprise a polynucleotide strand. This is discussed in more detail below.

In the disclosed methods, the blocking moiety prevents the motor protein from moving off the spacer. In one embodiment, this is achieved by binding the blocking moiety to the polynucleotide adapter adjacent to the spacer.

For example, in some embodiments the polynucleotide adapter comprises a polynucleotide strand contiguous with the spacer. In such embodiments, the blocking moiety may bind on the polynucleotide strand adjacent to the spacer. For example the blocking moiety may bind to one or more of the 20 nucleotides adjacent to the spacer. The blocking moiety may bind to one or more of the 10 nucleotides adjacent to the spacer. The blocking moiety may bind to one or more of the 5 nucleotides adjacent to the spacer. The blocking moiety may bind to either or both of the 2, 3 or 4 nucleotides adjacent to the spacer. In one embodiment, the blocking moiety binds to the terminal nucleotide adjacent to the spacer. In such embodiments the location of the blocking group in relation to the spacer is such that the motor protein cannot move off the spacer onto the portion of the polynucleotide adapter to which the blocking moiety is bonded. In some embodiments, the blocking moiety binds to a loading site described herein.

In some embodiments the blocking moiety is a protein such as a single strand binding protein (SSB), such as the *E. coli* single stranded binding protein. The protein binds to the polynucleotide adapter to prevent the movement of the motor protein off the spacer.

In some embodiments the blocking moiety is an intercalator. Any suitable intercalator can be used. The intercalator intercalates a polynucleotide strand of the polynucleotide adapter and thus prevents the movement of the motor protein past the intercalator. In some embodiments, positioning the intercalator close to the spacer can prevent movement of the motor protein off the spacer. In one embodiment, an intercalator can be introduced between to two of the 20 nucleotides adjacent to the spacer. In one embodiment, an intercalator can be introduced between to two of the 10 nucleotides adjacent to the spacer. In one embodiment, an intercalator can be introduced between to two of the 5 nucleotides adjacent to the spacer. In one embodiment, an intercalator can be introduced between the terminal two nucleotides adjacent to the spacer.

In some embodiments, the blocking moiety comprises a secondary structure of a polynucleotide strand. For example, the blocking moiety may comprise a secondary structure such as a pseudoknot for preventing the movement of the motor protein off the spacer.

In some embodiments, the blocking moiety may comprise a chemical tag. For example, the chemical tag may be attached to a group such as a polynucleotide which can bind to the polynucleotide adapter. Examples of suitable tags include, but are not limited to, biotin, a selectable polynucleotide sequence, antibodies, antibody fragments, such as Fab and ScSv, antigens, polynucleotide binding proteins, poly histidine tails and GST tags. Biotin specifically binds to avidins, such as streptavidin. A biotin group bound to an avidin such as streptavidin will prevent the movement of a motor protein. In some embodiments a biotin group bound to an avidin such as streptavidin will prevent the movement of a motor protein past the biotin group.

In some embodiments the blocking moiety comprises a single-stranded or non-hybridised polynucleotide having a length of between about 2 and about 1000 nucleotide units. The blocking moiety may be hybridised to the polynucleotide adapter so as to prevent the movement of the motor protein off the spacer.

In some embodiments the blocking moiety comprises a single-stranded or non-hybridised polynucleotide having a length of between about 2 and about 500 nucleotide units, for instance between about 2 and about 100 nucleotide units, such as between about 10 and about 100 nucleotide units, e.g. between about 20 and about 80 nucleotide units such as between about 30 and about 50 nucleotide units. In some embodiments the blocking moiety comprises a single-stranded or non-hybridised polynucleotide having a length of between about 1 and about 100 nucleotide units, e.g. between about 1 and about 90 nucleotide units, such as between about 1 and about 80 nucleotide units, e.g. between about 1 and about 70 nucleotide units, for example between about 1 and about 60 nucleotide units, for instance between about 1 and about 50 nucleotide units, e.g. between about 1 and about 40 nucleotide units; such as between about 1 and about 30 nucleotide units; for example between about 1 and about 20 nucleotide units such as between about 1 and about 10 nucleotide units. In some embodiments the blocking moiety comprises a single-stranded or non-hybridised polynucleotide having a length of between about 2 and about 100 nucleotide units, e.g. between about 2 and about 90 nucleotide units, such as between about 2 and about 80 nucleotide units, e.g. between about 2 and about 70 nucleotide units, for example between about 2 and about 60 nucleotide units, for instance between about 2 and about 50 nucleotide units, e.g. between about 2 and about 40 nucleotide units; such as between about 2 and about 30 nucleotide units; for example between about 2 and about 20 nucleotide units such as between about 2 and about 10 nucleotide units.

Those skilled in the art will appreciate that when the blocking moiety comprises a single-stranded or non-hybridised polynucleotide, the sequence of the blocking moiety polynucleotide is typically not determinative and can be controlled or chosen according to the adapter and motor protein and other experimental conditions. Exemplary sequences are provided solely by way of illustration in the examples. For example, the blocking moiety may comprise a polynucleotide sequence such as SEQ ID NO: 19 or a polynucleotide sequence having at least 20%, such as at least 30%, e.g. at least 40% such as at least 50%, e.g. at least 60% such as at least 70%, e.g. at least 80%, for example at least 90% e.g. at least 95% sequence similarity or identity to SEQ ID NO: 19. For example, the blocking moiety may comprise a polynucleotide sequence such as SEQ ID NO: 10 or a polynucleotide sequence having at least 20%, such as at least 30%, e.g. at least 40% such as at least 50%, e.g. at least 60% such as at least 70%, e.g. at least 80%, for example at least 90% e.g. at least 95% sequence similarity or identity to SEQ ID NO: 10. The blocking moiety may comprise a polynucleotide sequence corresponding to SEQ ID NO: 10 or to SEQ ID NO: 19 and comprising at least 1, at least 2, at least 3, at least 4, at least 5, at least 6, at least 7, at least 8, at least 9, or at least 10 nucleotide substitutions. Without being bound by theory, those skilled in the art will appreciate that the function of the blocking moiety in preventing movement of the motor protein off the spacer can be achieved by blocking moieties which are chosen to be compatible with the sequence of the adapter. The structure of the blocking moiety can be altered providing the blocking moiety can attach to the adapter (e.g. by hybridisation) and prevent movement of the motor protein from off the spacer.

Sometimes, the blocking moiety adapter has a sequence complementary to a sequence of the polynucleotide adapter in the region of the spacer (e.g. within about 20 nucleotides of the spacer, such as within about 10 nucleotides of the spacer, e.g. within about 5 nucleotides of the spacer, such as within 2, 3 or 4 nucleotides of the spacer), so that the blocking moiety polynucleotide can hybridise to the polynucleotide adapter in the region of the spacer and thus prevent the motor protein from moving off the spacer.

A blocking moiety comprising a single-stranded or non-hybridised polynucleotide which may attach, e.g. by hybridisation, to a polynucleotide adapter may also be referred to as a "trap strand". The trap strand traps the motor protein on the spacer. Attaching a trap strand to the polynucleotide adapter may comprise attaching the trap strand, e.g. by hybridisation, to a sequence of the polynucleotide adapter, e.g. a sequence close to or adjacent to the spacer of the polynucleotide adapter.

Typically the sequence to which the blocking moiety or trap strand attaches e.g. by hybridisation is a single stranded sequence such that the resulting adapter comprising the blocking moiety may be a double stranded polynucleotide. Those skilled in the art will thus appreciate that an adapter may comprise a region of double-stranded polynucleotide attached to a spacer; in such an embodiment the double-stranded polynucleotide blocks the movement of the motor protein off the spacer and one strand of the double-stranded polynucleotide or a portion of one strand of the double-stranded polynucleotide comprises the trap strand. This is discussed more in the examples.

As explained in more detail here, in some embodiments the blocking moiety if present is bound to the adapter once the motor protein has positioned on the spacer moiety. In some embodiments the blocking moiety if present is bound to the adapter before the motor protein has positioned on the spacer unit. In some embodiments a blocking moiety is bound to the adapter before the motor protein has positioned on a spacer unit comprising one or more nucleotide islands as described herein.

Loading Site

As discussed above, in some embodiments the polynucleotide adapter comprises a loading site connected to a spacer. A loading site is a site for loading the motor protein onto the polynucleotide adapter.

In one embodiment, the loading site is a linear molecule, such as a polymer. In some embodiments, the loading site may comprise deoxyribonucleic acid (DNA), ribonucleic acid (RNA), peptide nucleic acid (PNA), glycerol nucleic acid (GNA), threose nucleic acid (TNA), locked nucleic acid (LNA) or a synthetic polymer with nucleotide side chains. The loading site may comprise a polymer such as PEG.

In some embodiments, the motor protein engages with the loading site of the polynucleotide adapter. A motor protein may engage with the polynucleotide adapter (e.g. with the loading site of the polynucleotide adapter) if it contacts the polynucleotide adapter (e.g. the loading site of the polynucleotide adapter) and associates with the polynucleotide adapter. For example, the motor protein may associate to the polynucleotide adapter (e.g. the loading site) by binding to the polynucleotide adapter, or by forming a complex around the portion of the polynucleotide adapter to which it engages but not binding to the polynucleotide adapter. Thus, for instance, if the motor protein is a DNA processing enzyme and the loading site comprises a linear molecule which is not DNA (e.g. the loading site comprises RNA, PNA, GNA, TNA, LNA, or PEG, etc), the motor protein may associate with (engage with) the loading site without binding to it. On the other hand, if the loading site comprises DNA then the motor protein may engage with the loading site by binding to the loading site. Similarly, if the motor protein is an RNA processing enzyme and the loading site comprises a linear molecule which is not RNA (e.g. the loading site comprises DNA, PNA, GNA, TNA, LNA, or PEG, etc), the motor protein may associate with (engage with) the loading site without binding to it. On the other hand, if the loading site comprises RNA then the motor protein may engage with the loading site by binding to the loading site. Of course, in some embodiments the motor protein may bind to a loading site which does not comprise the natural substrate for the motor protein (e.g. a DNA-binding enzyme may in some embodiments bind to a loading site which comprises a linear molecule other than DNA, etc).

Accordingly, in some embodiments, the polynucleotide adapter comprises a loading site connected to a spacer and the motor protein binds to the loading site of the polynucleotide adapter.

In some embodiments of the disclosed methods, the polynucleotide adapter comprises a loading site connected to a spacer and the blocking moiety described herein binds to the loading site. As explained in more detail here, if the blocking moiety binds to the loading site the blocking moiety prevents the motor protein from moving off the spacer. In some embodiments the blocking moiety may prevent the motor protein from moving off the spacer onto the loading site.

In some embodiments, the loading site is contiguous with the spacer. In other words, the loading site may be directly attached to the spacer. In some embodiments, the loading site is contiguous with the spacer and the blocking moiety binds to the loading site immediately adjacent to the spacer. As will be apparent, in some embodiments binding the blocking moiety to the loading site immediately adjacent to the spacer prevents the motor protein is from moving off the spacer onto the polynucleotide adapter. In some embodiments binding the blocking moiety to the loading site immediately adjacent to the spacer prevents the motor protein from moving off the spacer onto the loading site.

For example, the polynucleotide adapter may comprise a loading site connected to a spacer, wherein the loading site comprises a single-stranded or non-hybridised polynucleotide. In some embodiments, the motor protein may bind to the polynucleotide adapter at the loading site and progress from the loading site onto the spacer. The blocking moiety may bind to the loading site (e.g. as described above), Binding the blocking moiety to the loading site may prevent the motor protein from moving back onto the single-stranded or non-hybridised polynucleotide.

In some embodiments, the loading site comprises a single-stranded or non-hybridised polynucleotide. A single-stranded polynucleotide strand may comprise an overhang region of a double stranded polynucleotide strand. A non-hybridised polynucleotide may comprise for example a Y shape polynucleotide as described in more detail above.

In some preferred embodiments, the loading site comprises a single-stranded or non-hybridised polynucleotide and the blocking moiety comprises a single-stranded or non-hybridised polynucleotide; and (ii) binding the blocking moiety to the loading site comprises hybridising the blocking moiety to the loading site.

In some embodiments the loading site comprises a single-stranded or non-hybridised polynucleotide having a length of between about 2 and about 1000 nucleotide units. In some embodiments the loading site comprises a single-stranded or non-hybridised polynucleotide having a length of between about 2 and about 500 nucleotide units, for instance between about 2 and about 100 nucleotide units, such as between about 10 and about 100 nucleotide units, e.g. between about 20 and about 80 nucleotide units such as between about 30 and about 50 nucleotide units. In some embodiments the loading site comprises a single-stranded or non-hybridised polynucleotide having a length of between about 1 and about 100 nucleotide units, e.g. between about 1 and about 90 nucleotide units, such as between about 1 and about 80 nucleotide units, e.g. between about 1 and about 70 nucleotide units, for example between about 1 and about 60 nucleotide units, for instance between about 1 and about 50 nucleotide units, e.g. between about 1 and about 40 nucleotide units; such as between about 1 and about 30 nucleotide units; for example between about 1 and about 20 nucleotide units such as between about 1 and about 10 nucleotide units. In some embodiments the loading site comprises a single-stranded or non-hybridised polynucleotide having a length of between about 2 and about 100 nucleotide units, e.g. between about 2 and about 90 nucleotide units, such as between about 2 and about 80 nucleotide units, e.g. between about 2 and about 70 nucleotide units, for example between about 2 and about 60 nucleotide units, for instance between about 2 and about 50 nucleotide units, e.g. between about 2 and about 40 nucleotide units; such as between about 2 and about 30 nucleotide units; for example between about 2 and about 20 nucleotide units such as between about 2 and about 10 nucleotide units. In some embodiments, the blocking moiety comprises a single-stranded or non-hybridised polynucleotide having a length of between about 2 and about 1000 nucleotide units. In some embodiments the blocking moiety comprises a single-stranded or non-hybridised polynucleotide having a length of between about 2 and about 500 nucleotide units, for instance between about 2 and about 100 nucleotide units, such as between about 10 and about 100 nucleotide units, e.g. between about 20 and about 80 nucleotide units such as between about 30 and about 50 nucleotide units. In some embodiments the blocking moiety comprises a single-stranded or non-hybridised polynucleotide having a length of between about 1 and about 100 nucleotide units, e.g. between about 1 and about 90 nucleotide units, such as between about 1 and about 80 nucleotide units, e.g. between about 1 and about 70 nucleotide units, for example between about 1 and about 60 nucleotide units, for instance between about 1 and about 50 nucleotide units, e.g. between about 1 and about 40 nucleotide units; such as between about 1 and about 30 nucleotide units; for example between about 1 and about 20 nucleotide units such as between about 1 and about 10 nucleotide units. In some embodiments the blocking moiety comprises a single-stranded or non-hybridised polynucleotide having a length of between about 2 and about 100 nucleotide units, e.g. between about 2 and about 90 nucleotide units, such as between about 2 and about 80 nucleotide units, e.g. between about 2 and about 70 nucleotide units, for example between about 2 and about 60 nucleotide units, for instance between about 2 and about 50 nucleotide units, e.g. between about 2 and about 40 nucleotide units; such as between about 2 and about 30 nucleotide units; for example between about 2 and about 20 nucleotide units such as between about 2 and about 10 nucleotide units.

In some embodiments, the loading site has a sequence which is complementary to the sequence of the blocking moiety.

Those skilled in the art will appreciate that the sequence of the loading site is typically not determinative and can be controlled or chosen according to the adapter and motor protein and other experimental conditions. Exemplary sequences are provided solely by way of illustration in the examples. Without being bound by theory, those skilled in the art will appreciate that the function of the loading site in promoting loading of the motor protein onto the spacer can be achieved by loading sites which are chosen to be compatible with the adapter and motor protein used in the method. The sequence of the loading site can thus be altered providing the motor protein can progress from the loading site onto the spacer, as described herein.

In some embodiments the backbone of the loading site and the blocking moiety is the same (e.g. the loading site and the blocking moiety both have a DNA backbone, an RNA backbone, etc). In other embodiments the backbone of the loading site and the blocking moiety is different (e.g. the loading site may have a DNA backbone and the blocking moiety have an RNA backbone or the loading site may have an RNA backbone and the blocking moiety have an DNA backbone, etc).

In some embodiments the hybridisation of the blocking moiety to the loading site creates a region of double-stranded polynucleotide adjacent to the spacer. Such regions typically prevent the movement of a motor protein from off the spacer onto the region of the loading site which is hybridised to the blocking moiety. For example, the loading site may comprise single-stranded polynucleotide and the blocking moiety may bind at the terminal nucleotide contiguous with the spacer so as to create a region of double-stranded polynucleotide contiguous with the spacer.

Loading Strand

In some embodiments the motor protein is loaded onto a polynucleotide adapter comprising a loading strand. In some embodiments a loading strand improves the efficiency of motor protein loading, particularly in embodiments of the methods provided herein in which it is desirable that only one motor protein is loaded onto a single adapter. In some embodiments the loading strand comprises a portion which is complementary to a sequence of the adapter adjacent to (or in the vicinity of, such as within 1, 2, 3, 4, or 5 nucleotides of) the spacer of the polynucleotide adapter. In some embodiments the loading strand further comprises a portion which is not complementary to the sequence of the polynucleotide adapter. In some embodiments the loading strand comprises a portion which is complementary to a sequence of the adapter and thus hybridises to the adapter in the vicinity of (e.g. adjacent to) the spacer; and a portion which is not complementary to the adapter sequence and thus does not hybridise to the adapter. In some embodiments the portion which does not hybridise to the adapter facilitates loading of the motor protein onto the adapter. In some embodiments the motor protein processes the hybridised loading strand/adapter complex and in doing so is caused to process onto the spacer. In some embodiments the processing of the motor protein onto the spacer displaces the loading strand from the polynucleotide adapter. In some embodiments the displacement of the loading strand from the adapter prevents the loading of subsequent motor proteins onto the adapter.

In some embodiments the loading strand has a length of between about 2 and about 500 nucleotide units, for instance between about 5 and about 100 nucleotide units, such as between about 10 and about 60 nucleotide units, e.g. between about 20 and about 40 nucleotide units.

Those skilled in the art will appreciate that the sequence of the loading strand is typically not determinative and can be controlled or chosen according to the adapter and motor protein and other experimental conditions. Exemplary sequences are provided solely by way of illustration in the examples. For example, the loading strand may comprise a polynucleotide sequence such as SEQ ID NO: 18 or a polynucleotide sequence having at least 20%, such as at least 30%, e.g. at least 40% such as at least 50%, e.g. at least 60% such as at least 70%, e.g. at least 80%, for example at least 90% e.g. at least 95% sequence similarity or identity to SEQ ID NO: 18. Without being bound by theory, those skilled in the art will appreciate that the function of the loading strand in promoting loading of the motor protein onto the spacer can be achieved by loading strands which are chosen to be compatible with the adapter and motor protein used in the method. The sequence of the loading strand can thus be altered providing the motor protein can progress from the loading strand onto the spacer, as described herein.

In some embodiments, a blocking moiety is attached to the adapter in the vicinity of the spacer (e.g. adjacent to the spacer) in place of the displaced loading strand. The blocking moiety may for example be a single-stranded or non-hybridised polynucleotide (i.e. a blocking strand) which may attach, e.g. by hybridisation, to the polynucleotide adapter in place of the displaced loading strand.

In some embodiments in which a loading strand is used to progress the motor protein onto the spacer and a blocking strand is used to prevent the motor protein moving off the spacer, the blocking strand may bind more strongly to the polynucleotide adapter than the loading strand. For example, the blocking strand may have a length greater than the loading strand and therefore hybridise more strongly than the loading strand. In some embodiments the blocking strand is provided at concentrations in excess of the loading strand. By providing excess blocking strand the re-annealing of displaced loading strand is reduced or prevented thus allowing the number of motor proteins on the polynucleotide adapter to be controlled. For example, the blocking strand may be present at concentrations at least 2×, such as at least 5×, e.g. at least 10×, such as at least 20×, e.g. at least 50× or at least 100× the concentration of the loading strand.

Progressing the Motor Protein onto the Spacer

As discussed in more detail herein, the methods provided herein comprise positioning a motor protein on a spacer comprised in an adapter.

As discussed in more detail herein, in some embodiments contacting the polynucleotide adapter with a motor protein causes the motor protein to progress onto the spacer of the polynucleotide adapter.

In some embodiments, causing the motor protein to progress from the loading site onto the spacer comprises providing the motor protein with an impetus to pass from the loading site onto the spacer. Any suitable impetus can be used.

Typically there is an energy barrier for a motor protein to progress from the polynucleotide adapter (e.g. from the loading site) onto the spacer. The energy barrier may arise from a change in the chemical composition of the linear molecule along which the motor protein progresses. For example, in some embodiments the change may be from a polynucleotide backbone of the loading site to a non-polynucleotide backbone of the spacer. In other embodiments, the energy barrier may arise from a change from a DNA or RNA backbone of the loading site to an abasic spacer. The typical existence of the energy barrier means that an impetus is often required to cause the motor protein to progress from the polynucleotide adapter (e.g. from the loading site) onto the spacer.

For example, in some embodiments causing the motor protein to progress onto the spacer comprises applying a physical or chemical force to the motor protein. In some embodiments, causing the motor protein to progress onto the spacer comprises contacting the motor protein with one or more fuel molecules. In some embodiments, a force is applied by a second motor protein which "pushes" the motor protein onto the spacer. In other words, in some embodiments the polynucleotide adapter comprises a loading site connected to a spacer; the motor protein is a first motor protein and causing the first motor protein to progress from the loading site onto the spacer comprises loading a second motor protein onto the loading site and causing the second motor protein to progress from the loading site towards the spacer, wherein the second motor protein forces the first motor protein onto the spacer.

In other embodiments, binding the blocking moiety to the polynucleotide adapter forces the motor protein onto the spacer. The binding of the blocking moiety to the polynucleotide adapter (e.g. to the loading site) can be sufficiently favourable as to overcome the energy barrier to force the motor protein onto the spacer.

In other embodiments, the motor protein is positioned on a spacer before or after a blocking moiety has been bound to the adapter. For example, a motor protein may be positioned on the spacer and a blocking moiety bound to the polynucleotide adapter may prevent the motor protein from moving off the spacer. In some embodiments a motor protein may be positioned on an adapter comprising a spacer and blocking moiety bound to the adapter. The motor protein may be positioned on an adapter by any suitable means. For example, the motor protein may preferentially localise at certain locations within the spacer. For example, in some embodiments the motor protein may bind to a nucleotide island within the spacer. Accordingly, in some embodiments contacting the polynucleotide adapter with the motor protein may comprise contacting the motor protein with a nucleotide island comprised in the spacer.

In such embodiments the motor protein is typically modified in order to prevent it from dissociating from the spacer e.g. by moving off the spacer. The motor protein may be modified before or after being positioned on the spacer. Typically the motor protein is modified after being positioned on the spacer. Modifications of motor proteins is described in more detail herein.

It will be apparent from the above discussion that some embodiments of the disclosed methods involve causing the motor protein to progress from the polynucleotide adapter onto the spacer.

In some embodiments, when the motor protein is on the spacer the spacer occupies the active site of the motor protein. In some embodiments, the active site is partially occupied by the spacer. In other embodiments, the active site is wholly occupied by the spacer. The active site may be occupied to a sufficient extent to impact on the turnover of fuel molecules by the motor protein. Typically, as used herein, the active site of a motor protein refers to the polynucleotide-binding cleft in the motor protein. Those skilled in the art will appreciate that the ATP-binding site of the motor protein may be distinct from the polynucleotide adapter. Thus, in some embodiments, the polynucleotide-binding cleft of the motor protein is occupied by the spacer and the ATP-binding site of the motor protein is not occupied by the spacer. In other embodiments both the polynucleotide-binding cleft and the ATP-binding site of the motor protein are occupied by the spacer. Thus, the polynucleotide-binding cleft of the motor protein may be occupied by the spacer and the ATP-binding site of the motor protein may be occluded or blocked by the spacer, or may be accessible to ATP. Without being bound by theory, a motor protein may still be stalled on a spacer and not engage in futile turnover even if the ATP binding site is accessible. For example, in some embodiments ATP hydrolysis requires conformational changes in the motor protein which are induced by polynucleotide-binding to the polynucleotide-binding cleft of the motor protein. When stalled on a spacer so that the polynucleotide-binding cleft is inaccessible to polynucleotides, such conformational changes do not occur and futile turnover is reduced or eliminated.

In some embodiments, the spacer spans the whole or part of the footprint of the motor protein. In some embodiments, the spacer spans the entire footprint of the motor protein and occupies the active site of the motor protein. In other words, in some embodiments the motor protein progresses onto the spacer so that it is wholly on the spacer.

Those skilled in the art will appreciate that there is a significant difference between a motor protein which is stalled on a spacer as defined herein, and a motor protein which is stalled merely close to a spacer e.g. adjacent to a spacer. If a motor protein is merely adjacent to a spacer or only spans the spacer by a trivial amount then futile turnover will not necessarily be prevented. Allowing a motor protein to move off the spacer to this extent does not correspond to preventing the motor protein from moving off the spacer as defined in the present claims. A motor protein which is "on" a spacer due to a slight overlap between the motor protein and the spacer but which is not prevented from turning over fuel molecules at substantially the same rate as when it is bound to a polynucleotide is not on the spacer as used herein.

Accordingly, in some embodiments, when the spacer occupies the active site of the motor protein the turnover of fuel molecules by the motor protein is reduced. In some embodiments, the turnover of fuel molecules by the motor protein is eliminated.

Motor Proteins

As those skilled in the art will appreciate, any suitable motor protein can be used in the methods and products provided herein. In one embodiment, a motor protein may be any protein that is capable of binding to a polynucleotide and controlling its movement with respect to a nanopore, e.g. through the pore.

In one embodiment, a motor protein is or is derived from a polynucleotide handling enzyme. A polynucleotide handling enzyme is a polypeptide that is capable of interacting with and modifying at least one property of a polynucleotide. The enzyme may modify the polynucleotide by cleaving it to form individual nucleotides or shorter chains of nucleotides, such as di- or trinucleotides. The enzyme may modify the polynucleotide by orienting it or moving it to a specific position.

In one embodiment, the motor protein is derived from a member of any of the Enzyme Classification (EC) groups 3.1.11, 3.1.13, 3.1.14, 3.1.15, 3.1.16, 3.1.21, 3.1.22, 3.1.25, 3.1.26, 3.1.27, 3.1.30 and 3.1.31.

Typically, the motor protein is a helicase, a polymerase, an exonuclease, a topoisomerase, or a variant thereof.

In some embodiments, the motor protein on the spacer of the polynucleotide adapter is modified to prevent the motor protein disengaging from the spacer (other than by passing off the end of the spacer). The motor protein can be adapted in any suitable way. For example, the motor protein can be loaded on the adapter and then modified in order to prevent it from disengaging from the spacer. Alternatively, the motor protein can be modified to prevent it from disengaging from the spacer before it is loaded onto the adapter. Modification of a motor protein in order to prevent it from disengaging from a spacer can be achieved using methods known in the art, such as those discussed in WO 2014/013260, which is hereby incorporated by reference in its entirety, and with particular reference to passages describing the modification of motor proteins such as helicases in order to prevent them from disengaging with polynucleotide strands. For example, a motor protein can be modified by treating with tetramethylazodicarboxamide (TMAD).

For example, the motor protein may have a polynucleotide-unbinding opening; e.g. a cavity, cleft or void through which a polynucleotide strand may pass when the motor protein disengages from the strand. In some embodiments, the polynucleotide-unbinding opening is the opening through which a spacer may pass when the motor protein disengages from the spacer. In some embodiments, the polynucleotide-unbinding opening for a given motor protein can be determined by reference to its structure, e.g. by reference to its X-ray crystal structure. The X-ray crystal structure may be obtained in the presence and/or the absence of a polynucleotide substrate. In some embodiments, the location of a polynucleotide-unbinding opening in a given motor protein may be deduced or confirmed by molecular modelling using standard packages known in the art. In some embodiments, the polynucleotide-unbinding opening may be transiently produced by movement of one or more parts e.g. one or more domains of the motor protein.

The motor protein may be modified by closing the polynucleotide-unbinding opening. Closing the polynucleotide-unbinding opening may therefore prevent the motor protein from disengaging from the spacer. For example, the motor protein may be modified by covalently closing the polynucleotide-unbinding opening. In some embodiments, a preferred motor protein for addressing in this way is a helicase.

In one embodiment, the motor protein is an exonuclease. Suitable enzymes include, but are not limited to, exonuclease I from *E. coli* (SEQ ID NO: 1), exonuclease III enzyme from *E. coli* (SEQ ID NO: 2), RecJ from *T. thermophilus* (SEQ ID NO: 3) and bacteriophage lambda exonuclease (SEQ ID NO: 4), TatD exonuclease and variants thereof. Three subunits comprising the sequence shown in SEQ ID NO: 3 or a variant thereof interact to form a trimer exonuclease.

In one embodiment, the motor protein is a polymerase. The polymerase may be PyroPhage® 3173 DNA Polymerase (which is commercially available from Lucigen® Corporation), SD Polymerase (commercially available from Bioron®), Klenow from NEB or variants thereof. In one embodiment, the enzyme is Phi29 DNA polymerase (SEQ ID NO: 5) or a variant thereof. Modified versions of Phi29 polymerase that may be used in the invention are disclosed in U.S. Pat. No. 5,576,204.

In one embodiment the motor protein is a topoisomerase. In one embodiment, the topoisomerase is a member of any of the Moiety Classification (EC) groups 5.99.1.2 and 5.99.1.3. The topoisomerase may be a reverse transcriptase, which are enzymes capable of catalysing the formation of cDNA from a RNA template. They are commercially available from, for instance, New England Biolabs® and Invitrogen®.

In one embodiment, the motor protein is a helicase. Any suitable helicase can be used in accordance with the methods provided herein. For example, the or each motor protein used in accordance with the present disclosure may be independently selected from a Hel308 helicase, a RecD helicase, a TraI helicase, a TrwC helicase, an XPD helicase, and a Dda helicase, or a variant thereof. Monomeric helicases may comprise several domains attached together. For instance, TraI helicases and TraI subgroup helicases may contain two RecD helicase domains, a relaxase domain and a C-terminal domain. The domains typically form a monomeric helicase that is capable of functioning without forming oligomers. Particular examples of suitable helicases include Hel308, NS3, Dda, UvrD, Rep, PcrA, Pif1 and TraI. These helicases typically work on single stranded DNA. Examples of helicases that can move along both strands of a double stranded DNA include FtfK and hexameric enzyme complexes, or multisubunit complexes such as RecBCD.

Hel308 helicases are described in publications such as WO 2013/057495, the entire contents of which are incorporated by reference. RecD helicases are described in publications such as WO 2013/098562, the entire contents of which are incorporated by reference. XPD helicases are described in publications such as WO 2013/098561, the entire contents of which are incorporated by reference. Dda helicases are described in publications such as WO 2015/055981 and WO 2016/055777, the entire contents of each of which are incorporated by reference.

In one embodiment the helicase comprises the sequence shown in SEQ ID NO: 6 (Trwc Cba) or a variant thereof, the sequence shown in SEQ ID NO: 7 (Hel308 Mbu) or a variant thereof or the sequence shown in SEQ ID NO: 8 (Dda) or a variant thereof. Variants may differ from the native sequences in any of the ways discussed herein. An example variant of SEQ ID NO: 8 comprises E94C/A360C. A further example variant of SEQ ID NO: 8 comprises E94C/A360C and then (ΔM1)G1G2 (i.e. deletion of M1 and then addition of G1 and G2).

In some embodiments a motor protein (e.g. a helicase) can control the movement of polynucleotides in at least two active modes of operation (when the motor protein is provided with all the necessary components to facilitate movement, e.g. fuel and cofactors such as ATP and $Mg^{2+}$ discussed herein) and one inactive mode of operation (when the motor protein is not provided with the necessary components to facilitate movement).

When provided with all the necessary components to facilitate movement (i.e. in the active modes), the motor protein (e.g. helicase) moves along the polynucleotide in a 5' to 3' or a 3' to 5' direction (depending on the motor protein). In embodiments in which the motor protein is used to control the movement of a polynucleotide strand with respect to a nanopore, the motor protein can be used to either move the polynucleotide away from (e.g. out of) the pore (e.g. against an applied field) or the polynucleotide towards (e.g. into) the pore (e.g. with an applied field). For example, when the end of the polynucleotide towards which the motor protein moves is captured by a pore, the motor protein works against the direction of the field resulting from the applied potential and pulls the threaded polynucleotide out of the pore (e.g. into the cis chamber). However, when the end away from which the motor protein moves is captured in the pore, the motor protein works with the direction of the field resulting from the applied potential and pushes the threaded polynucleotide into the pore (e.g. into the trans chamber).

When the motor protein (e.g. helicase) is not provided with the necessary components to facilitate movement (i.e. in the inactive mode) it can bind to the polynucleotide and act as a brake slowing the movement of the polynucleotide when it is moved with respect to a nanopore, e.g. by being pulled into the pore by a field resulting from an applied potential. In the inactive mode, it does not matter which end of the polynucleotide is captured, it is the applied field which determines the movement of the polynucleotide with respect to the pore, and the motor protein acts as a brake. When in the inactive mode, the movement control of the polynucleotide by the motor protein can be described in a number of ways including ratcheting, sliding and braking.

As discussed above, the methods disclosed herein may reduce the concept of futile turnover. Turnover is the chemical (enzymatic) conversion of a fuel molecule by a motor protein.

Fuel is typically free nucleotides or free nucleotide analogues. The free nucleotides may be one or more of, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The free nucleotides are usually selected from AMP, TMP, GMP, CMP, UMP, dAMP, dTMP, dGMP or dCMP. The free nucleotides are typically adenosine triphosphate (ATP).

A cofactor for the motor protein is a factor that allows the motor protein to function. The cofactor is preferably a divalent metal cation. The divalent metal cation is preferably $Mg^{2+}$, $Mn^{2+}$, $Ca^{2+}$ or $Co^{2+}$. The cofactor is most preferably $Mg^{2+}$.

Removal of Excess Motor Protein

In some embodiments, the provided methods further comprise the step of removing excess motor protein molecules which are not located on the spacer. The removal of excess motor proteins can be referred to as a stress step. A stress step can be used to remove incorrectly bound motor proteins from the polynucleotide adapter. In embodiments of the provided methods which comprise modifying the motor protein in order to prevent it from disengaging from the spacer, a stress step can be used to remove motor proteins which are not correctly modified.

Removal of excess motor proteins is beneficial in order to reduce or exclude the presence of unbound motor proteins which are not stalled on a polynucleotide adapter as described herein. Unstalled motor proteins may engage with polynucleotide strands and/or may consume fuel molecules that are present, i.e. may engage in futile turnover. Removing excess motor proteins reduces or prevents this futile turnover from unstalled motor proteins and thus reduces the unproductive consumption of fuel molecules.

Unbound motor proteins can be removed (e.g. in a stress step) in any suitable manner. For example, the unbound motor proteins can be removed by washing or filtering. Unbound motor proteins can be removed by using a high salt wash buffer. Unbound motor proteins can be removed using specific pH or temperature conditions that promote their removal. For example, stress conditions may include for example high salt concentrations in the presence of fuel such as ATP.

Progressing the Motor Protein Off the Spacer

As discussed in more detail herein, in some embodiments the adapter is useful for stalling a motor protein prior to its use to control the movement of a target polynucleotide. For example, in some embodiments the disclosed adapter provides a motor protein for controlling the movement of a target polynucleotide with respect to a nanopore. In some embodiments, the movement of a target polynucleotide with respect to a nanopore is useful to characterise the target polynucleotide.

As discussed in more detail herein, the disclosed methods involve stalling a motor protein on a spacer. The blocking moiety prevents the motor protein from moving off the spacer onto the polynucleotide adapter, e.g. from moving from the spacer onto a loading site of the polynucleotide adapter.

Typically there is an energy barrier for a motor protein to progress from the spacer onto a target polynucleotide in order to control the movement of the target polynucleotide. The energy barrier may arise from a change in the chemical composition of the linear molecule along which the motor protein progresses. For example, in some embodiments the change may be from a non-polynucleotide backbone of the spacer to a polynucleotide backbone of the target polynucleotide. In other embodiments, the energy barrier may arise from a change from an basic spacer to a DNA or RNA backbone of the target polynucleotide. The typical existence of the energy barrier means that an impetus is often required to cause the motor protein to progress from the polynucleotide adapter (e.g. from the spacer) onto the target polynucleotide.

In some embodiments, causing the motor protein to progress from the spacer onto the target polynucleotide thus comprises providing the motor protein with an impetus to pass from the spacer onto the target polynucleotide. Any suitable impetus can be used.

For example, in some embodiments, the impetus can be provided by contacting the polynucleotide adapter with a nanopore. For example, in some embodiments, the nanopore engages with the polynucleotide adapter and forces the motor protein onto the target polynucleotide.

In more detail, in some embodiments a polynucleotide adapter having a motor protein stalled on a spacer thereof is contacted with a target polynucleotide under conditions such that the polynucleotide adapter is attached to the target polynucleotide. For example, as described in more detail herein the polynucleotide adapter can be ligated to the target polynucleotide adapter, e.g. to an end of the target polynucleotide. The polynucleotide adapter-target polynucleotide conjugate can be contacted with a nanopore such that the polynucleotide adapter engages with the nanopore. For example, the polynucleotide adapter may thread through the nanopore. Movement of the polynucleotide adapter with respect to the nanopore (e.g. through the nanopore) can provide a force on the motor protein stalled on the spacer of the polynucleotide adapter. For example, in embodiments where the polynucleotide adapter is threaded through a nanopore under the influence of an applied potential, the force applied by the nanopore on the motor protein as it approaches or contacts the nanopore is sufficient to force the motor protein onto the target polynucleotide. In such embodiments the nanopore can be considered as "pushing" the motor protein from off the spacer onto the target polynucleotide adapter. Such embodiments are particularly suited to (but not limited to) embodiments of the disclosure in which the polynucleotide adapter comprises a spacer positioned between (i) a loading site and (ii) a polynucleotide strand which can be ligated or otherwise attached onto the target polynucleotide.

In other embodiments the force required to progress the motor protein from the spacer onto the target polynucleotide is provided by applying a physical or chemical force to the motor protein. In some embodiments, causing the motor protein to progress from the spacer onto the target polynucleotide comprises contacting the motor protein with one or more fuel molecules. In some embodiments, a force is applied by a second motor protein which "pushes" the motor protein off the spacer onto the target polynucleotide. In other words, in some embodiments the polynucleotide adapter comprises a spacer and is attached to the target polynucleotide; the motor protein is a first motor protein and causing the first motor protein to progress from the spacer onto the target polynucleotide comprises loading a second motor protein onto the polynucleotide adapter and causing the second motor protein to progress towards the target polynucleotide, wherein the second motor protein forces the first motor protein onto the spacer. In such embodiments the polynucleotide adapter typically comprises a loading site connected to the end of the spacer away from the target polynucleotide (away from the end of the polynucleotide adapter which is or will be attached to the target polynucleotide).

It will be appreciated that in such embodiments it is typically not necessary to remove the blocking moiety in order to progress the motor protein from off the spacer onto the target polynucleotide. However in some embodiments the method involves displacing the blocking moiety. For example, the blocking moiety may be removed or displaced by contacting the polynucleotide adapter with a nanopore. In some embodiments removal of the blocking moiety from the polynucleotide adapter allows the motor protein to move off the spacer onto the polynucleotide adapter and/or onto the target polynucleotide.

In some embodiments the blocking moiety binds to the polynucleotide adapter on the side of the spacer away from the target polynucleotide (i.e. away from the end of the polynucleotide adapter which is or will be attached to the target polynucleotide). In such embodiments the polynucleotide adapter typically comprises a loading site connected to the end of the spacer away from the target polynucleotide (away from the end of the polynucleotide adapter which is or will be attached to the target polynucleotide) and the blocking moiety binds to the polynucleotide adapter between the loading site and spacer.

In other embodiments the blocking moiety binds to the polynucleotide adapter between the spacer and the target polynucleotide (towards the end of the polynucleotide adapter which is or will be attached to the target polynucleotide). In such embodiments the polynucleotide adapter typically comprises a loading site connected to the end of the spacer away from the target polynucleotide (away from the end of the polynucleotide adapter which is or will be attached to the target polynucleotide) and the blocking moiety binds to the polynucleotide adapter towards the end of the polynucleotide adapter which is or will be attached to the target polynucleotide.

Controlling Movement and Characterisation

Also provided herein is a method of controlling the movement of a target polynucleotide with respect to a transmembrane nanopore, comprising:

i) providing (A) a target polynucleotide; (B) a polynucleotide adapter comprising a spacer; and (C) a motor protein;
ii) carrying out a method as disclosed herein thereby stalling the motor protein on the spacer of the polynucleotide adapter;
iii) contacting the target polynucleotide and the stalled motor protein on the spacer of the polynucleotide adapter with the nanopore; and
iv) applying a potential across the transmembrane nanopore thereby causing the motor protein to move past the spacer onto the target polynucleotide thereby controlling the movement of the target polynucleotide with respect to the nanopore.

Any of the methods in embodiments disclosed herein can be used to stall the motor protein on the spacer of the polynucleotide adapter.

In one embodiment, the target polynucleotide is bound to the polynucleotide adapter. In one embodiment, step (iii) comprises binding the polynucleotide adapter to the target polynucleotide.

In one embodiment, the motor protein is stalled on the polynucleotide adapter before the polynucleotide adapter is attached to the target polynucleotide. In another embodiment, the polynucleotide adapter is attached to the target polynucleotide before the motor protein is stalled on the polynucleotide adapter.

Also provided herein is a method of controlling the movement of a target polynucleotide with respect to a transmembrane nanopore, comprising:

i) providing a target polynucleotide;
ii) providing a polynucleotide adapter comprising a spacer and having a motor protein stalled thereon, wherein said polynucleotide adapter is obtained according to any one of the methods disclosed herein;
iii) contacting the target polynucleotide and the polynucleotide adapter with the nanopore; and
iv) applying a potential across the transmembrane nanopore thereby causing the motor protein to move past the spacer onto the target polynucleotide thereby controlling the movement of the target polynucleotide with respect to the nanopore.

Any of the methods in embodiments disclosed herein can be used to stall the motor protein on the spacer of the polynucleotide adapter.

In one embodiment, the target polynucleotide is bound to the polynucleotide adapter. In one embodiment, step (iii) comprises binding the polynucleotide adapter to the target polynucleotide.

In the disclosed methods, the polynucleotide adapter can be attached to the target polynucleotide in any manner. The adapters are preferably covalently attached to the target polynucleotide. The adapters may be ligated to the target polynucleotide. The adapters may be ligated to either end of the target polynucleotide, i.e. the 5' or the 3' end, or to both ends of the target polynucleotide i.e. to the 5' end and to the 3' end. The adapters may be ligated to the target polynucleotide using any method known in the art. The adapter may be ligated to the target polynucleotide in the absence of ATP or using gamma-S-ATP (ATPγS) instead of ATP. Usually, if the motor protein is stalled on the polynucleotide adapter when the polynucleotide adapter is attached to the target polynucleotide, the adapter is ligated to the target polynucleotide in the absence of ATP. The adapter may be ligated using a ligase, such as T4 DNA ligase, *E. coli* DNA ligase, Taq DNA ligase, Tma DNA ligase and 9° N DNA ligase. The ligase may be removed from the sample before step (iii) of the method. The adapter may be attached using a topoisomerisase. The topoisomerase may, for example be a member of any of the Moiety Classification (EC) groups 5.99.1.2 and 5.99.1.3.

Also provided is a method of characterising a target polynucleotide, comprising:

i) carrying out one of the methods disclosed above; and
ii) taking one or more measurements as the target polynucleotide moves with respect to the nanopore, wherein the one or more measurements are indicative of one or more characteristics of the target polynucleotide, and thereby characterising the target polynucleotide as it moves with respect to the nanopore.

Polynucleotide Adapters

Also provided are polynucleotide adapters comprising spacers and having a motor protein stalled on the spacer. It will be understood that any of the polynucleotide adapters disclosed herein can be applied in the embodiments of the methods discussed herein and above.

In one embodiment, provided herein is a polynucleotide adapter comprising (i) a spacer; (ii) a motor protein stalled on the spacer, wherein the active site of the motor protein is occupied by the spacer; and (iii) a blocking moiety bound to the adapter, wherein the blocking moiety prevents the motor protein from moving off the spacer.

In some embodiments, the spacer, the motor protein and the blocking moiety are as described in detail herein.

In one embodiment, (i) the adapter comprises a loading site connected to the spacer and the blocking moiety is bound to the loading site; and (ii) the blocking moiety prevents the motor protein from engaging with the loading site. In some embodiments, the loading site is as described herein.

In one embodiment, provided is a polynucleotide adapter comprising:

i) $\{L_B\text{-S-D}\}_n$ or $\{\text{D-S-}L_B\}_n$ in the 5' to 3' direction; wherein $L_B$ is a blocked loading site; S is a spacer; D is a double-stranded polynucleotide; and n is an integer, optionally an integer from 1 to about 20; and
ii) one or more motor proteins stalled on the spacer (S); wherein the or each $L_B$ moiety prevents the or each motor protein from moving off the spacer (S) in the direction away from the double-stranded polynucleotide (D).

In some embodiments, the loading site(s), spacer(s), and motor protein(s) are as described herein.

In some embodiments, n is an integer from 1 to about 10, e.g. from 1 to about 5, such as 1, 2, 3, or 4, often 1 or 2. In some embodiments n is more than 1 and multiple motor proteins can be stalled on the multiple spacers S.

In some embodiments, the double-stranded polynucleotide has a length of from about 1 to about 1000 nucleotides. In some embodiments the double-stranded polynucleotide has a length of between about 5 and about 500 nucleotides, for instance between about 10 and about 100 nucleotides, e.g. between about 20 and about 80 nucleotides such as between about 30 and about 50 nucleotides.

In some embodiments, $L_B$ may be a polynucleotide which is the same type of polynucleotide as D or may be a different type of polynucleotide from D. $L_B$ and/or D may be the same type of polynucleotide as a target polynucleotide to which the adapter may be attached or may be a different type of polynucleotide from the target polynucleotide. For example, $L_B$ may be a double stranded DNA and D may be a double stranded DNA and the adapter may be suitable for attaching to a target polynucleotide which is a double stranded DNA.

In one embodiment, provided is a polynucleotide adapter comprising:

i) $\{L_B\text{-S-D}\}_n$ or $\{\text{D-S-}L_B\}_n$ in the 5' to 3' direction; wherein $L_B$ is a first double-stranded polynucleotide; S is a spacer; D is a second double-stranded polynucleotide; and n is an integer, optionally an integer from 1 to about 20; and wherein the first double-stranded polynucleotide ($L_B$) is contiguous with the spacer (S) and the spacer (S) is contiguous with the second double-stranded polynucleotide (D); and
ii) one or more motor proteins is stalled on the spacer (S).

In some embodiments, the spacer(s) and motor protein(s) are as described herein.

In some embodiments, n is an integer from 1 to about 10, e.g. from 1 to about 5, such as 1, 2, 3, or 4, often 1 or 2.

In some embodiments, $L_B$ may be a polynucleotide which is the same type of polynucleotide as D or may be a different type of polynucleotide from D. $L_B$ and/or D may be the same type of polynucleotide as a target polynucleotide to which the adapter may be attached or may be a different type of polynucleotide from the target polynucleotide. For example, $L_B$ may be a double stranded DNA and D may be a double stranded DNA and the adapter may be suitable for attaching to a target polynucleotide which is a double stranded DNA.

Kit

Also provided are kits comprising polynucleotide adapters and motor proteins. It will be understood that any of the polynucleotide adapters disclosed herein can be applied in the embodiments of the kits discussed herein and above.

In one embodiment, provided is a kit for modifying a target polynucleotide, comprising:

i) a polynucleotide adapter comprising a spacer;
ii) a motor protein capable of controlling the movement of the target polynucleotide; and
iii) a blocking moiety capable of binding to the polynucleotide adapter so that when the motor protein is located on the spacer of the polynucleotide adapter and the active site of the motor protein is occupied by the spacer, the motor protein is prevented from moving off the spacer.

In one embodiment, the polynucleotide adapter is a polynucleotide adapter as described in more detailed herein. In one embodiment, the motor protein is a motor protein as described herein. In one embodiment the blocking moiety is a blocking moiety as described herein.

In one embodiment, the polynucleotide adapter comprises a loading site. The loading site may be any of the loading sites as described herein. In one embodiment, the blocking moiety is capable of binding to the polynucleotide adapter so that the motor protein is prevented from engaging with the loading site.

Also provided is a kit for modifying a target polynucleotide, comprising:

i) a polynucleotide adapter comprising a spacer and a blocking moiety bound to the polynucleotide adapter; and
ii) a motor protein capable of controlling the movement of the target polynucleotide;

wherein when the motor protein is bound to the adapter, the blocking moiety prevents the motor protein from moving off the spacer.

The polynucleotide adapter, spacer, blocking moiety and motor protein are typically as defined herein in more detail.

System

Also provided are systems comprising polynucleotide adapters, motor proteins and nanopores. It will be understood that any of the polynucleotide adapters disclosed herein can be applied in the embodiments of the systems discussed herein and above.

In one embodiment provided is a system for characterising a target polynucleotide comprising:

a polynucleotide adapter comprising a spacer;

a motor protein, wherein the active site of the motor protein is occupied by the spacer;

a blocking moiety bound to the adapter, wherein the blocking moiety prevents the motor protein from moving off the spacer;

a nanopore for characterising the target polynucleotide as the target polynucleotide moves with respect to the nanopore.

In one embodiment, the polynucleotide adapter is a polynucleotide adapter as described in more detailed herein. In one embodiment, the motor protein is a motor protein as described herein. In one embodiment the blocking moiety is a blocking moiety as described herein. In one embodiment the nanopore is a nanopore as described herein, The system may further comprise a membrane; control equipment; etc as defined herein.

In one embodiment, the polynucleotide adapter comprises a loading site. The loading site may be any of the loading sites as described herein. In one embodiment, the blocking moiety is capable of binding to the polynucleotide adapter so that the motor protein is prevented from engaging with the loading site.

In one embodiment the system further comprises the target polynucleotide. In one embodiment the target polynucleotide is a target polynucleotide as described herein.

Target Polynucleotide

In embodiments of the present disclosure which relate to characterising a target polynucleotide, the target analyte moves with respect to, such as into or through, a transmembrane nanopore as described in more detail herein.

In one embodiment, the presence, absence or one or more characteristics of a target polynucleotide are determined. The methods may be for determining the presence, absence or one or more characteristics of at least one target polynucleotide. The methods may concern determining the presence, absence or one or more characteristics of two or more target polynucleotide. The methods may comprise determining the presence, absence or one or more characteristics of any number of target polynucleotides, such as 2, 5, 10, 15, 20, 30, 40, 50, 100 or more target polynucleotides. Any number of characteristics of the one or more target polynucleotides may be determined, such as 1, 2, 3, 4, 5, 10 or more characteristics.

The binding of a molecule (e.g. a target polynucleotide) in the channel of the pore will have an effect on the open-channel ion flow through the pore, which is the essence of "molecular sensing" of pore channels. Variation in the open-channel ion flow can be measured using suitable measurement techniques by the change in electrical current (for example, WO 2000/28312 and D. Stoddart et al., Proc. Natl. Acad. Sci., 2010, 106, 7702-7 or WO 2009/077734). The degree of reduction in ion flow, as measured by the reduction in electrical current, is related to the size of the obstruction within, or in the vicinity of, the pore. Binding of a molecule of interest (e.g. the target polynucleotide) in or near the pore therefore provides a detectable and measurable event, thereby forming the basis of a "biological sensor". Detecting the presence of biological molecules finds application in personalised drug development, medicine, diagnostics, life science research, environmental monitoring and in the security and/or the defence industry.

The target polynucleotide may be secreted from cells. Alternatively, the target analyte can be an analyte that is present inside cells such that the analyte must be extracted from the cells before the method can be carried out.

In one embodiment, the target polynucleotide is a nucleic acid. A polynucleotide is defined as a macromolecule comprising two or more nucleotides. The naturally-occurring nucleic acid bases in DNA and RNA may be distinguished by their physical size. As a nucleic acid molecule, or individual base, passes through the channel of a nanopore, the size differential between the bases causes a directly correlated reduction in the ion flow through the channel. The variation in ion flow may be recorded. Suitable electrical measurement techniques for recording ion flow variations are described in, for example, WO 2000/28312 and D. Stoddart et al., Proc. Natl. Acad. Sci., 2010, 106, pp 7702-7 (single channel recording equipment); and, for example, in WO 2009/077734 (multi-channel recording techniques). Through suitable calibration, the characteristic reduction in ion flow can be used to identify the particular nucleotide and associated base traversing the channel in real-time. In typical nanopore nucleic acid sequencing, the open-channel ion flow is reduced as the individual nucleotides of the nucleic sequence of interest sequentially pass through the channel of the nanopore due to the partial blockage of the channel by the nucleotide. It is this reduction in ion flow that is measured using the suitable recording techniques described above. The reduction in ion flow may be calibrated to the reduction in measured ion flow for known nucleotides through the channel resulting in a means for determining which nucleotide is passing through the channel, and therefore, when done sequentially, a way of determining the nucleotide sequence of the nucleic acid passing through the nanopore. For the accurate determination of individual nucleotides, it has typically required for the reduction in ion flow through the channel to be directly correlated to the size of the individual nucleotide passing through the constriction (or "reading head"). It will be appreciated that sequencing may be performed upon an intact nucleic acid polymer that is 'threaded' through the pore via the action of an associated motor protein such as a polymerase or helicase, for example. Alternatively, sequences may be determined by passage of nucleotide triphosphate bases that have been sequentially removed from a target nucleic acid in proximity to the pore (see for example WO 2014/187924).

The polynucleotide or nucleic acid may comprise any combination of any nucleotides. The nucleotides can be naturally occurring or artificial. One or more nucleotides in the polynucleotide can be oxidized or methylated. One or more nucleotides in the polynucleotide may be damaged. For instance, the polynucleotide may comprise a pyrimidine dimer. Such dimers are typically associated with damage by ultraviolet light and are the primary cause of skin melanomas. One or more nucleotides in the polynucleotide may be modified, for instance with a label or a tag, for which suitable examples are known by a skilled person. The polynucleotide may comprise one or more spacers. A nucleotide typically contains a nucleobase, a sugar and at least one phosphate group. The nucleobase and sugar form a nucleoside. The nucleobase is typically heterocyclic. Nucleobases include, but are not limited to, purines and pyrimidines and more specifically adenine (A), guanine (G), thymine (T), uracil (U) and cytosine (C). The sugar is typically a pentose sugar. Nucleotide sugars include, but are not limited to, ribose and deoxyribose. The sugar is preferably a deoxyribose. The polynucleotide preferably comprises the following nucleosides: deoxyadenosine (dA), deoxyuridine (dU) and/or thymidine (dT), deoxyguanosine (dG) and deoxycytidine (dC). The nucleotide is typically a ribonucleotide or deoxyribonucleotide. The nucleotide typically contains a monophosphate, diphosphate or triphosphate. The nucleotide may comprise more than three phosphates, such as 4 or 5 phosphates. Phosphates may be attached on the 5' or 3' side of a nucleotide. The nucleotides in the polynucleotide may be attached to each other in any manner. The nucleotides are typically attached by their sugar and phosphate groups as in nucleic acids. The nucleotides may be connected via their nucleobases as in pyrimidine dimers. The polynucleotide may be single stranded or double stranded. At least a portion of the polynucleotide is preferably double stranded. The polynucleotide is most preferably ribonucleic nucleic acid (RNA) or deoxyribonucleic acid (DNA). In particular, said method using a polynucleotide as an analyte alternatively comprises determining one or more characteristics selected from (i) the length of the polynucleotide, (ii) the identity of the polynucleotide, (iii) the sequence of the polynucleotide, (iv) the secondary structure of the polynucleotide and (v) whether or not the polynucleotide is modified.

The polynucleotide can be any length (i). For example, the polynucleotide can be at least 10, at least 50, at least 100, at least 150, at least 200, at least 250, at least 300, at least 400 or at least 500 nucleotides or nucleotide pairs in length. The polynucleotide can be 1000 or more nucleotides or nucleotide pairs, 5000 or more nucleotides or nucleotide pairs in length or 100000 or more nucleotides or nucleotide pairs in length. Any number of polynucleotides can be investigated. For instance, the method may concern characterising 2, 3, 4, 5, 6, 7, 8, 9, 10, 20, 30, 50, 100 or more polynucleotides. If two or more polynucleotides are characterised, they may be different polynucleotides or two instances of the same polynucleotide. The polynucleotide can be naturally occurring or artificial. For instance, the method may be used to verify the sequence of a manufactured oligonucleotide. The method is typically carried out in vitro.

Nucleotides can have any identity (ii), and include, but are not limited to, adenosine monophosphate (AMP), guanosine monophosphate (GMP), thymidine monophosphate (TMP), uridine monophosphate (UMP), 5-methylcytidine monophosphate, 5-hydroxymethylcytidine monophosphate, cytidine monophosphate (CMP), cyclic adenosine monophosphate (cAMP), cyclic guanosine monophosphate (cGMP), deoxyadenosine monophosphate (dAMP), deoxyguanosine monophosphate (dGMP), deoxythymidine monophosphate (dTMP), deoxyuridine monophosphate (dUMP), deoxycytidine monophosphate (dCMP) and deoxymethylcytidine monophosphate. The nucleotides are preferably selected from AMP, TMP, GMP, CMP, UMP, dAMP, dTMP, dGMP, dCMP and dUMP. A nucleotide may be abasic (i.e. lack a nucleobase). A nucleotide may also lack a nucleobase and a sugar (i.e. is a C3 spacer). The sequence of the nucleotides (iii) is determined by the consecutive identity of following nucleotides attached to each other throughout the polynucleotide strain, in the 5' to 3' direction of the strand.

The target polynucleotide may comprise the products of a PCR reaction, genomic DNA, the products of an endonuclease digestion and/or a DNA library. The target polynucleotide may be obtained from or extracted from any organism or microorganism. The target polynucleotide is often obtained from a human or animal, e.g. from urine, lymph, saliva, mucus, seminal fluid or amniotic fluid, or from whole blood, plasma or serum. The target polynucleotide may be obtained from a plant e.g. a a cereal, legume, fruit or vegetable. The target polynucleotide may comprise genomic DNA. The genomic DNA may be fragmented. The DNA may be fragmented by any suitable method. For example, methods of fragmenting DNA are known in the art, Such methods may use a transposase, such as a MuA transposase. Often the genomic DNA is not fragmented. In some embodiments, the target polynucleotide may be DNA, RNA and/or a DNA/RNA hybrid.

Nanopore

In embodiments of the invention which relate to a nanopore, any suitable nanopore can be used. In one embodiment a nanopore is a transmembrane pore.

A transmembrane pore is a structure that crosses the membrane to some degree. It permits hydrated ions driven by an applied potential to flow across or within the membrane. The transmembrane pore typically crosses the entire membrane so that hydrated ions may flow from one side of the membrane to the other side of the membrane. However, the transmembrane pore does not have to cross the membrane. It may be closed at one end. For instance, the pore may be a well, gap, channel, trench or slit in the membrane along which or into which hydrated ions may flow.

Any transmembrane pore may be used in the methods provided herein. The pore may be biological or artificial. Suitable pores include, but are not limited to, protein pores, polynucleotide pores and solid state pores. The pore may be a DNA origami pore (Langecker et al., Science, 2012; 338: 932-936). Suitable DNA origami pores are disclosed in WO2013/083983.

In one embodiment, the nanopore is a transmembrane protein pore. A transmembrane protein pore is a polypeptide or a collection of polypeptides that permits hydrated ions, such as polynucleotide, to flow from one side of a membrane to the other side of the membrane. In the methods provided herein, the transmembrane protein pore is capable of forming a pore that permits hydrated ions driven by an applied potential to flow from one side of the membrane to the other. The transmembrane protein pore preferably permits polynucleotides to flow from one side of the membrane, such as a triblock copolymer membrane, to the other. The transmembrane protein pore allows a polynucleotide to be moved through the pore.

In one embodiment, the nanopore is a transmembrane protein pore which is a monomer or an oligomer. The pore is preferably made up of several repeating subunits, such as at least 6, at least 7, at least 8, at least 9, at least 10, at least 11, at least 12, at least 13, at least 14, at least 15, or at least 16 subunits. The pore is preferably a hexameric, heptameric, octameric or nonameric pore. The pore may be a homo-oligomer or a hetero-oligomer.

In one embodiment, the transmembrane protein pore comprises a barrel or channel through which the ions may flow. The subunits of the pore typically surround a central axis and contribute strands to a transmembrane β-barrel or channel or a transmembrane (α-helix bundle or channel.

Typically, the barrel or channel of the transmembrane protein pore comprises amino acids that facilitate interaction with an analyte, such as a target polynucleotide (as described herein). These amino acids are preferably located near a constriction of the barrel or channel. The transmembrane protein pore typically comprises one or more positively charged amino acids, such as arginine, lysine or histidine, or aromatic amino acids, such as tyrosine or tryptophan. These amino acids typically facilitate the interaction between the pore and nucleotides, polynucleotides or nucleic acids.

In one embodiment, the nanopore is a transmembrane protein pore derived from β-barrel pores or α-helix bundle pores. β-barrel pores comprise a barrel or channel that is formed from β-strands. Suitable β-barrel pores include, but are not limited to, β-toxins, such as α-hemolysin, anthrax toxin and leukocidins, and outer membrane proteins/porins of bacteria, such as *Mycobacterium smegmatis* porin (Msp), for example MspA, MspB, MspC or MspD, CsgG, outer membrane porin F (OmpF), outer membrane porin G (OmpG), outer membrane phospholipase A and *Neisseria* autotransporter lipoprotein (NalP) and other pores, such as lysenin. α-helix bundle pores comprise a barrel or channel that is formed from α-helices. Suitable α-helix bundle pores include, but are not limited to, inner membrane proteins and a outer membrane proteins, such as WZA and ClyA toxin.

In one embodiment the nanopore is a transmembrane pore derived from or based on Msp, α-hemolysin (α-HL), lysenin, CsgG, ClyA, Sp1 or haemolytic protein fragaceatoxin C (FraC).

In one embodiment, the nanopore is a transmembrane protein pore derived from CsgG, e.g. from CsgG from *E. coli* Str. K-12 substr. MC4100. Such a pore is oligomeric and typically comprises 7, 8, 9 or 10 monomers derived from CsgG. The pore may be a homo-oligomeric pore derived from CsgG comprising identical monomers. Alternatively, the pore may be a hetero-oligomeric pore derived from CsgG comprising at least one monomer that differs from the others. Examples of suitable pores derived from CsgG are disclosed in WO 2016/034591.

In one embodiment, the nanopore is a transmembrane pore derived from lysenin. Examples of suitable pores derived from lysenin are disclosed in WO 2013/153359.

In one embodiment, the nanopore is a transmembrane pore derived from or based on α-hemolysin (α-HL). The wild type α-hemolysin pore is formed of 7 identical monomers or sub-units (i.e., it is heptameric). An α-hemolysin pore may be α-hemolysin-NN or a variant thereof. The variant preferably comprises N residues at positions E111 and K147.

In one embodiment, the nanopore is a transmembrane protein pore derived from Msp, e.g. from MspA. Examples of suitable pores derived from MspA are disclosed in WO 2012/107778.

In one embodiment, the nanopore is a transmembrane pore derived from or based on ClyA.

Membrane

In embodiments of the invention which comprise the use of a transmembrane nanopore, the transmembrane nanopore is typically present in a membrane. Any suitable membrane may be used in the system.

The membrane is preferably an amphiphilic layer. An amphiphilic layer is a layer formed from amphiphilic molecules, such as phospholipids, which have both hydrophilic and lipophilic properties. The amphiphilic molecules may be synthetic or naturally occurring. Non-naturally occurring amphiphiles and amphiphiles which form a monolayer are known in the art and include, for example, block copolymers (Gonzalez-Perez et al., Langmuir, 2009, 25, 10447-10450). Block copolymers are polymeric materials in which two or more monomer sub-units that are polymerized together to create a single polymer chain. Block copolymers typically have properties that are contributed by each monomer sub-unit. However, a block copolymer may have unique properties that polymers formed from the individual sub-units do not possess. Block copolymers can be engineered such that one of the monomer sub-units is hydrophobic (i.e. lipophilic), whilst the other sub-unit(s) are hydrophilic whilst in aqueous media. In this case, the block copolymer may possess amphiphilic properties and may form a structure that mimics a biological membrane. The block copolymer may be a diblock (consisting of two monomer sub-units), but may also be constructed from more than two monomer sub-units to form more complex arrangements that behave as amphipiles. The copolymer may be a triblock, tetrablock or pentablock copolymer. The membrane is preferably a triblock copolymer membrane.

Archaebacterial bipolar tetraether lipids are naturally occurring lipids that are constructed such that the lipid forms a monolayer membrane. These lipids are generally found in extremophiles that survive in harsh biological environments, thermophiles, halophiles and acidophiles. Their stability is believed to derive from the fused nature of the final bilayer. It is straightforward to construct block copolymer materials that mimic these biological entities by creating a triblock polymer that has the general motif hydrophilic-hydrophobic-hydrophilic. This material may form monomeric membranes that behave similarly to lipid bilayers and encompass a range of phase behaviours from vesicles through to laminar membranes. Membranes formed from these triblock copolymers hold several advantages over biological lipid membranes. Because the triblock copolymer is synthesised, the exact construction can be carefully controlled to provide the correct chain lengths and properties required to form membranes and to interact with pores and other proteins.

Block copolymers may also be constructed from sub-units that are not classed as lipid sub-materials; for example a hydrophobic polymer may be made from siloxane or other non-hydrocarbon based monomers. The hydrophilic sub-section of block copolymer can also possess low protein binding properties, which allows the creation of a membrane that is highly resistant when exposed to raw biological samples. This head group unit may also be derived from non-classical lipid head-groups.

Triblock copolymer membranes also have increased mechanical and environmental stability compared with biological lipid membranes, for example a much higher operational temperature or pH range. The synthetic nature of the block copolymers provides a platform to customise polymer based membranes for a wide range of applications.

In some embodiments, the membrane is one of the membranes disclosed in International Application No. WO2014/064443 or WO2014/064444.

The amphiphilic molecules may be chemically-modified or functionalised to facilitate coupling of the polynucleotide. The amphiphilic layer may be a monolayer or a bilayer. The amphiphilic layer is typically planar. The amphiphilic layer may be curved. The amphiphilic layer may be supported.

Amphiphilic membranes are typically naturally mobile, essentially acting as two dimensional fluids with lipid diffusion rates of approximately $10^{-8}$ cm $s^{-1}$. This means that the pore and coupled polynucleotide can typically move within an amphiphilic membrane.

The membrane may be a lipid bilayer. Lipid bilayers are models of cell membranes and serve as excellent platforms for a range of experimental studies. For example, lipid bilayers can be used for in vitro investigation of membrane proteins by single-channel recording. Alternatively, lipid bilayers can be used as biosensors to detect the presence of a range of substances. The lipid bilayer may be any lipid bilayer. Suitable lipid bilayers include, but are not limited to, a planar lipid bilayer, a supported bilayer or a liposome. The lipid bilayer is preferably a planar lipid bilayer. Suitable lipid bilayers are disclosed in WO 2008/102121, WO 2009/077734 and WO 2006/100484.

Methods for forming lipid bilayers are known in the art. Lipid bilayers are commonly formed by the method of Montal and Mueller (Proc. Natl. Acad. Sci. USA., 1972; 69: 3561-3566), in which a lipid monolayer is carried on aqueous solution/air interface past either side of an aperture which is perpendicular to that interface. The lipid is normally added to the surface of an aqueous electrolyte solution by first dissolving it in an organic solvent and then allowing a drop of the solvent to evaporate on the surface of the aqueous solution on either side of the aperture. Once the organic solvent has evaporated, the solution/air interfaces on either side of the aperture are physically moved up and down past the aperture until a bilayer is formed. Planar lipid bilayers may be formed across an aperture in a membrane or across an opening into a recess.

The method of Montal & Mueller is popular because it is a cost-effective and relatively straightforward method of forming good quality lipid bilayers that are suitable for protein pore insertion. Other common methods of bilayer formation include tip-dipping, painting bilayers and patch-clamping of liposome bilayers.

Tip-dipping bilayer formation entails touching the aperture surface (for example, a pipette tip) onto the surface of a test solution that is carrying a monolayer of lipid. Again, the lipid monolayer is first generated at the solution/air interface by allowing a drop of lipid dissolved in organic solvent to evaporate at the solution surface. The bilayer is then formed by the Langmuir-Schaefer process and requires mechanical automation to move the aperture relative to the solution surface.

For painted bilayers, a drop of lipid dissolved in organic solvent is applied directly to the aperture, which is submerged in an aqueous test solution. The lipid solution is spread thinly over the aperture using a paintbrush or an equivalent. Thinning of the solvent results in formation of a lipid bilayer. However, complete removal of the solvent from the bilayer is difficult and consequently the bilayer formed by this method is less stable and more prone to noise during electrochemical measurement.

Patch-clamping is commonly used in the study of biological cell membranes. The cell membrane is clamped to the end of a pipette by suction and a patch of the membrane becomes attached over the aperture. The method has been adapted for producing lipid bilayers by clamping liposomes which then burst to leave a lipid bilayer sealing over the aperture of the pipette. The method requires stable, giant and unilamellar liposomes and the fabrication of small apertures in materials having a glass surface.

Liposomes can be formed by sonication, extrusion or the Mozafari method (Colas et al. (2007) Micron 38:841-847).

In some embodiments, a lipid bilayer is formed as described in International Application No. WO 2009/077734. Advantageously in this method, the lipid bilayer is formed from dried lipids. In a most preferred embodiment, the lipid bilayer is formed across an opening as described in WO2009/077734.

A lipid bilayer is formed from two opposing layers of lipids. The two layers of lipids are arranged such that their hydrophobic tail groups face towards each other to form a hydrophobic interior. The hydrophilic head groups of the lipids face outwards towards the aqueous environment on each side of the bilayer. The bilayer may be present in a number of lipid phases including, but not limited to, the liquid disordered phase (fluid lamellar), liquid ordered phase, solid ordered phase (lamellar gel phase, interdigitated gel phase) and planar bilayer crystals (lamellar sub-gel phase, lamellar crystalline phase).

Any lipid composition that forms a lipid bilayer may be used. The lipid composition is chosen such that a lipid bilayer having the required properties, such surface charge, ability to support membrane proteins, packing density or mechanical properties, is formed. The lipid composition can comprise one or more different lipids. For instance, the lipid composition can contain up to 100 lipids. The lipid composition preferably contains 1 to 10 lipids. The lipid composition may comprise naturally-occurring lipids and/or artificial lipids.

The lipids typically comprise a head group, an interfacial moiety and two hydrophobic tail groups which may be the same or different. Suitable head groups include, but are not limited to, neutral head groups, such as diacylglycerides (DG) and ceramides (CM); zwitterionic head groups, such as phosphatidylcholine (PC), phosphatidylethanolamine (PE) and sphingomyelin (SM); negatively charged head groups, such as phosphatidylglycerol (PG); phosphatidylserine (PS), phosphatidylinositol (PI), phosphatic acid (PA) and cardiolipin (CA); and positively charged headgroups, such as trimethylammonium-Propane (TAP). Suitable interfacial moieties include, but are not limited to, naturally-occurring interfacial moieties, such as glycerol-based or ceramide-based moieties. Suitable hydrophobic tail groups include, but are not limited to, saturated hydrocarbon chains, such as lauric acid (n-Dodecanolic acid), myristic acid (n-Tetradecononic acid), palmitic acid (n-Hexadecanoic acid), stearic acid (n-Octadecanoic) and arachidic (n-Eicosanoic); unsaturated hydrocarbon chains, such as oleic acid (cis-9-Octadecanoic); and branched hydrocarbon chains, such as phytanoyl. The length of the chain and the position and number of the double bonds in the unsaturated hydrocarbon chains can vary. The length of the chains and the position and number of the branches, such as methyl groups, in the branched hydrocarbon chains can vary. The hydrophobic tail groups can be linked to the interfacial moiety as an ether or an ester. The lipids may be mycolic acid.

The lipids can also be chemically-modified. The head group or the tail group of the lipids may be chemically-modified. Suitable lipids whose head groups have been chemically-modified include, but are not limited to, PEG-modified lipids, such as 1,2-Diacyl-sn-Glycero-3-Phosphoethanolamine-N-[Methoxy(Polyethylene glycol)-2000]; functionalised PEG Lipids, such as 1,2-Distearoyl-sn-Glycero-3 Phosphoethanolamine-N-[Biotinyl(Polyethylene Glycol)2000]; and lipids modified for conjugation, such as 1,2-Dioleoyl-sn-Glycero-3-Phosphoethanolamine-N-(succinyl) and 1,2-Dipalmitoyl-sn-Glycero-3-Phosphoethanolamine-N-(Biotinyl). Suitable lipids whose tail groups have been chemically-modified include, but are not limited to, polymerisable lipids, such as 1,2-bis(10,12-tricosadiynoyl)-sn-Glycero-3-Phosphocholine; fluorinated lipids, such as 1-Palmitoyl-2-(16-Fluoropalmitoyl)-sn-Glycero-3-Phosphocholine; deuterated lipids, such as 1,2-Dipalmitoyl-D62-sn-Glycero-3-Phosphocholine; and ether linked lipids, such as 1,2-Di-O-phytanyl-sn-Glycero-3-Phosphocholine. The lipids may be chemically-modified or functionalised to facilitate coupling of the polynucleotide.

The amphiphilic layer, for example the lipid composition, typically comprises one or more additives that will affect the properties of the layer. Suitable additives include, but are not limited to, fatty acids, such as palmitic acid, myristic acid and oleic acid; fatty alcohols, such as palmitic alcohol, myristic alcohol and oleic alcohol; sterols, such as cholesterol, ergosterol, lanosterol, sitosterol and stigmasterol; lysophospholipids, such as 1-Acyl-2-Hydroxy-sn-Glycero-3-Phosphocholine; and ceramides.

In another embodiment, the membrane comprises a solid state layer. Solid state layers can be formed from both organic and inorganic materials including, but not limited to, microelectronic materials, insulating materials such as $Si_3N_4$, $Al_2O_3$, and SiO, organic and inorganic polymers such as polyamide, plastics such as Teflon® or elastomers such as two-component addition-cure silicone rubber, and glasses. The solid state layer may be formed from graphene. Suitable graphene layers are disclosed in WO 2009/035647. If the membrane comprises a solid state layer, the pore is typically present in an amphiphilic membrane or layer contained within the solid state layer, for instance within a hole, well, gap, channel, trench or slit within the solid state layer. The skilled person can prepare suitable solid state/amphiphilic hybrid systems. Suitable systems are disclosed in WO 2009/020682 and WO 2012/005857. Any of the amphiphilic membranes or layers discussed above may be used.

The methods disclosed herein are typically carried out using (i) an artificial amphiphilic layer comprising a pore, (ii) an isolated, naturally-occurring lipid bilayer comprising a pore, or (iii) a cell having a pore inserted therein. The methods are typically carried out using an artificial amphiphilic layer, such as an artificial triblock copolymer layer. The layer may comprise other transmembrane and/or intramembrane proteins as well as other molecules in addition to the pore. Suitable apparatus and conditions are discussed below. The method of the invention is typically carried out in vitro.

Anchor

In one embodiment, the polynucleotide adapter comprises a membrane anchor or a transmembrane pore anchor attached to the adapter. In one embodiment the anchor characterisation of a target polynucleotide in accordance with the methods disclosed herein. For example, in methods which comprise contacting the target polynucleotide with a transmembrane pore, a membrane anchor or transmembrane pore anchor may promote localisation of the selected polynucleotides around the transmembrane pore.

The anchor may be a polypeptide anchor and/or a hydrophobic anchor that can be inserted into the membrane. In one embodiment, the hydrophobic anchor is a lipid, fatty acid, sterol, carbon nanotube, polypeptide, protein or amino acid, for example cholesterol, palmitate or tocopherol. The anchor may comprise thiol, biotin or a surfactant. In one aspect the anchor may be biotin (for binding to streptavidin), amylose (for binding to maltose binding protein or a fusion protein), Ni-NTA (for binding to poly-histidine or poly-histidine tagged proteins) or peptides (such as an antigen).

In one embodiment, the anchor comprises a linker, or 2, 3, 4 or more linkers. Preferred linkers include, but are not limited to, polymers, such as polynucleotides, polyethylene glycols (PEGs), polysaccharides and polypeptides. These linkers may be linear, branched or circular. For instance, the linker may be a circular polynucleotide. The adapter may hybridise to a complementary sequence on a circular polynucleotide linker. The one or more anchors or one or more linkers may comprise a component that can be cut or broken down, such as a restriction site or a photolabile group. The linker may be functionalised with maleimide groups to attach to cysteine residues in proteins. Suitable linkers are described in WO 2010/086602.

In one embodiment, the anchor is cholesterol or a fatty acyl chain. For example, any fatty acyl chain having a length of from 6 to 30 carbon atom, such as hexadecanoic acid, may be used. Examples of suitable anchors and methods of attaching anchors to adapters are disclosed in WO 2012/164270 and WO 2015/150786.

Characterising

In embodiments of the present disclosure which relate to characterising a target polynucleotide, the target analyte moves with respect to, such as into or through, a transmembrane nanopore as described in more detail herein.

The characterisation methods may be carried out using any apparatus that is suitable for investigating a membrane/pore system in which a pore is inserted into a membrane. The characterisation method may be carried out using any apparatus that is suitable for transmembrane pore sensing. For example, the apparatus may comprise a chamber comprising an aqueous solution and a barrier that separates the chamber into two sections. The barrier may have an aperture in which a membrane containing a transmembrane pore is formed. Transmembrane pores are described herein.

The characterisation methods may be carried out using the apparatus described in WO 2008/102120, WO 2010/122293 or WO 00/28312.

The characterisation methods may involve measuring the ion current flow through the pore, typically by measurement of a current. Alternatively, the ion flow through the pore may be measured optically, such as disclosed by Heron et al: J. Am. Chem. Soc. 9 Vol. 131, No. 5, 2009. Therefore the apparatus may also comprise an electrical circuit capable of applying a potential and measuring an electrical signal across the membrane and pore. The characterisation methods may be carried out using a patch clamp or a voltage clamp. The characterisation methods preferably involve the use of a voltage clamp. The characterisation methods may be carried out on a silicon-based array of wells where each array comprises 128, 256, 512, 1024, 2000, 3000, 4000, 6000, 10000, 12000, 15000 or more wells.

The characterisation methods may involve the measuring of a current flowing through the pore. The method is typically carried out with a voltage applied across the membrane and pore. The voltage used is typically from +2 V to −2 V, typically −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 100 mV to 240 mV and most preferably in the range of 120 mV to 220 mV. It is possible to increase discrimination between different nucleotides by a pore by using an increased applied potential.

The characterisation methods are typically carried out in the presence of any charge carriers, such as metal salts, for example alkali metal salts, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. In the exemplary apparatus discussed above, the salt is present in the aqueous solution in the chamber. Potassium chloride (KCl), sodium chloride (NaCl) or caesium chloride (CsCl) is typically used. KCl is preferred. The salt may be an alkaline earth metal salt such as calcium chloride (CaCl2)). The salt concentration may be at saturation. The salt concentration may be 3M or lower and is typically from 0.1 to 2.5 M, from 0.3 to 1.9 M, from 0.5 to 1.8 M, from 0.7 to 1.7 M, from 0.9 to 1.6 M or from 1 M to 1.4 M. The salt concentration is preferably from 150 mM to 1 M. The characterisation method is preferably carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 M or at least 3.0 M. High salt concentrations provide a high signal to noise ratio and allow for currents indicative of binding/no binding to be identified against the background of normal current fluctuations.

The characterisation methods are typically carried out in the presence of a buffer. In the exemplary apparatus discussed above, the buffer is present in the aqueous solution in the chamber. Any suitable buffer may be used. Typically, the buffer is HEPES. Another suitable buffer is Tris-HCl buffer. The methods are typically carried out at a pH of from 4.0 to 12.0, from 4.5 to 10.0, from 5.0 to 9.0, from 5.5 to 8.8, from 6.0 to 8.7 or from 7.0 to 8.8 or 7.5 to 8.5. The pH used is preferably about 7.5.

The characterisation methods may be carried out at from 0° C. to 100° C., from 15° C. to 95° C., from 16° C. to 90° C., from 17° C. to 85° C., from 18° C. to 80° C., 19° C. to 70° C., or from 20° C. to 60° C. The characterisation methods are typically carried out at room temperature. The characterisation methods are optionally carried out at a temperature that supports enzyme function, such as about 37° C.

It is to be understood that although particular embodiments, specific configurations as well as materials and/or molecules, have been discussed herein for methods according to the present invention, various changes or modifications in form and detail may be made without departing from the scope and spirit of this invention. The following examples are provided to better illustrate particular embodiments, and they should not be considered limiting the application. The application is limited only by the claims.

EXAMPLES

Example 1

This example shows that futile turnover is reduced when a motor protein is stalled on a spacer in accordance with the methods disclosed herein, compared to when it is stalled adjacent to a spacer.

A first DNA construct comprising a single-stranded polynucleotide strand of SEQ ID NO: 9 and comprising a spacer (4 iSp18 units, IDT) was hybridized to complementary single-stranded DNA strands (SEQ ID Nos: 10 and 11). SEQ ID NO: 10 is complementary to the portion of SEQ ID NO: 9 between the 5' end of SEQ ID NO: 9 and the 5' end of the spacer and is referred to as a "test" strand. A motor protein (closed T4 Dda helicase) was stalled on the spacer. The construct is depicted schematically in FIG. 1A.

A second DNA construct was produced with a closed T4 Dda helicase loaded on the spacer. The second DNA construct was identical to the first DNA construct, except that SEQ ID NO: 12 was used instead of SEQ ID NO: 10. SEQ ID NO: 12 is identical to SEQ ID NO: 10, except it lacks the terminal ten nucleotides at the 5' end of SEQ ID NO: 10. In consequence, SEQ ID NO: 12 hybridises to SEQ ID NO: 9 to leave a region of single-stranded DNA of 10 nucleotides in length to the 5' end of the spacer. SEQ ID NO: 12 is thus referred to as a "test −10" strand. The construct is depicted schematically in FIG. 1B.

A spectrophotometric assay was used to determine the rate of fuel use (ATP turnover) by the motor protein (closed T4 Dda helicase in this example) stalled on the first and second DNA constructs, respectively. In brief, the spectrophotometric assay monitors ATP usage by a motor protein using a coupled enzyme system. Pyruvate Kinase (PK, rabbit muscle, 600-1000 U/mL, Sigma) converts the ADP formed by the motor protein into ATP. This reaction requires the conversion of one molecule of phosphor(enol)pyruvate (PEP, phospho(enol)pyruvic acid monopotassium salt, Sigma) into pyruvate. The pyruvate is converted into lactate by Lactate Dehydrogenase (LDH, rabbit muscle, 900-1400 U/mL, Sigma), resulting in the oxidation of an NADH molecule. The oxidation of NADH is followed spectrophotometrically due to a decrease in absorbance at 340-380 nm (extinction coefficients are 1210 $M^{-1}$ $cm^{-1}$ at 380 nm and 6220 $M^{-1}$ $cm^{-1}$ at 340 nm). As one molecule of NADH is oxidised per molecule of ADP converted into ATP, the decrease in absorbance signal is proportional to the steady state rate of ATP hydrolysis by the motor protein.

FIG. 1C shows the calculated rate of ATP turnover by the closed T4 Dda helicase when stalled on the first and second DNA constructs, respectively. The catalytic rate of ATP turnover ($k_{cat}$) when the closed T4 Dda helicase was stalled on the spacer of the first construct was ca. 115 $s^{-1}$. By contrast, when the closed T4 Dda helicase was stalled on the second construct, adjacent to the spacer, the rate of ATP turnover was approximately double this rate ($k_{cat}$ ca. 235 $s^{-1}$). The rate of futile turnover by the closed T4 Dda helicase was thus approximately halved.

Example 2

This Example compares adapters with various different spacer designs and demonstrates that futile ATP turnover is reduced when a motor protein is stalled on the spacer in accordance with the methods provided herein.

Multiple different adapters were prepared with spacer designs as shown in the results table below. The tested adapters comprised polynucleotide strands as follows: (1) a Top Strand, (2) a Bottom Strand, and (3) a Blocking Strand. The Top Strand included the spacer design being tested, flanked by polynucleotide sequences on either side. The Blocking Strand was a single-stranded polynucleotide blocking moiety such as described herein.

Adapter Sequences

```
Top Strand:
333333333333333333333333333333CCTTTTTTTTGGCGTCTGCT

TGGGTGTTTAAC
C/[spacer sequence]/CCACAACTTCGTTCAGTTACGTATTGCT
(i.e., SEQ ID NO: 13; comprising SEQ ID NOs: 14
and 16 spanning the spacer sequence. SEQ ID NO: 14
comprises SEQ ID NO: 15)

Bottom Strand:
5phos/GCAATACGTAACTGAACGAAGTTGTGG (i.e., SEQ ID
NO: 17)

Loading Strand:
GGTTAAACACCCAAGCAGACGCCTTT (i.e., SEQ ID NO: 18)

Blocking Strand:
GGTTAAACACCCAAGCAGACGCCAAAAAAAAGG/3Cy5Sp/(i.e.,
SEQ ID NO: 19)
```

Adapter Preparation and Loading

Motor protein was loaded onto adapters that initially comprised a Top Strand, a Bottom Strand and a Loading Strand. The use of a Loading Strand is an optional feature that can improve the efficiency of motor protein loading where it is desired to reduce the proportion of adapters having multiple motor proteins loaded on a single adapter. The motor protein is caused to progress onto the spacer, in accordance with methods provided herein; in doing so the motor protein displaces the Loading Strand from the adapter. The Blocking Strand is subsequently annealed to the adapter to produce the completed adapter with motor protein stalled on the spacer and prevented from moving off by the Blocking Strand. The Blocking Strand is able to preferentially bind to the adapter compared to the Loading Strand, due to the greater length of the Blocking Strand; the preferential binding is further aided by the Blocking Strand being provided at a significantly greater concentration than the Loading Strand.

Adapter Preparation Protocol

Adapter polynucleotide strands were assembled by annealing the strands in potassium acetate buffer (400 mM HEPES pH8.0, 400 mM Potassium Acetate) at the following concentrations:

| | Volume (μL) | Final Concentration |
|---|---|---|
| Top Strand | 20 | 10 μM |
| Loading strand | 22 | 11 μM |
| Bottom Strand | 22 | 11 μM |
| 1x KOAc buffer | 100 | 0.5x |
| Nuclease Free Water | 36 | — |
| Total | 200 | |

Motor protein (Dda helicase) was combined with annealed adapter at a final concentration of 50-500 nM DNA and at least 7× molar excess protein under ambient conditions for 10-20 minutes. TMAD (100 μM) in potassium acetate buffer (as above) was added and incubated at 35° C. for one hour. Salt/ATP buffer (final concentration: 0.5M NaCl, 1 mM ATP, 10 mM MgCl2) together with Blocking Strand at 20× Top Strand concentration was added and the mixture incubated at room temperature for 25-30 minutes.

Adapters with bound helicase were purified using a SPRI bead purification system and adapter production was verified using a TBE gel.

ATP Turnover and Stability Testing

Each adapter was tested for ATP turnover and stability.

ATP turnover provides a measurement of futile ATP turnover while the adapter is not engaged in any sequencing reaction; the lower the ATP turnover, the lower the futile ATP usage and the greater the adapter fuel efficiency.

Adapter stability was tested under conditions typically found in nanopore sequencing reactions, and provides an indication of how long a given adapter may be expected to function in such a setting. It is to be noted that sequencing reactions carried out under different conditions, for example in lower salt concentrations or reduced temperatures, may provide increased adapter stability.

The tested adapters were named as B1 through B52 (see results table below). The results were compared to a commercially-available Oxford Nanopore sequencing adapter comprising a motor protein (herein referred to as adapter "AA").

ATPase Assay Protocol

Adapter samples for testing were diluted to a concentration of 10 nM in SPRI elution buffer (50 m Tris pH 8, 20 nM NaCl). 10 μL of each 10 nM adapter sample was added to a 384-well plate.

An NADH master mix was prepared containing 2.2 μL 40 U/mL lactate dehydrogenase/pyruvate kinase, 33.3 μL 1.33× sequencing buffer, 3.3 μL 3.33 mM NADH, 0.7 μL 5.33 mM pyruvic acid, and 10.4 μL nuclease-free water.

NADH master mix was incubated for 10 minutes at room temperature to turn over any free ADP in solution.

30 μL of the NADH master mix was added to 10 μL of adapter sample in each well of the 384-well plate and mixed.

The plate was added to a UV-absorbance plate reader and absorbance measured at 380 nm at 34° C. for 120 cycles.

The data generated were analysed to determine $k_{cat}$ and ATP turnover values.

Stability Assay Protocol

Assay master mix was prepared containing 7.8 μL nuclease-free water, 10 μL 2× sequencing buffer, and 0.2 μL B-OTG.

Samples for testing were prepared by adding 2 μL of 125 nM adapter to 18 μL of assay master mix +/−ATP in a PCR tube.

Each sample was incubated in a thermal cycler at 34° C. with a cover temperature of 45° C., for 24 hours.

Following incubation, samples were run on 5% TBE gel, 160 mV, 30 mins, or 4-20% TBE gel, 180 mV, 45 mins.

Gels were stained with SYBR Gold for 10 minutes and imaged on an Amersham Typhoon scanner using Cy3 settings.

Densitometric analysis was performed to determine the proportion of bound and unbound adapter.

Results

The results for ATP turnover are shown as a percentage of the turnover seen with the comparison adapter AA, which serves as a baseline. Accordingly, ATP turnover percentage values less than 100% all indicate a decrease in futile ATP turnover and improved fuel efficiency compared to the baseline. All of the tested adapters shown in the results table had reduced ATP turnover and thus improved fuel efficiency compared to adapter AA.

The stability of the adapters was also tested, with results shown as the increase in the percentage of adapter polynucleotide unbound to motor protein over a period of 24 hours. The results demonstrate that stable adapters having loaded motor protein were produced.

Results Table:

| Adapter Name | Spacer (schematic sequence) | Spacer sequence | 24 hr Stability (% Increase in Unbound DNA) | ATP turnover (% AA) |
|---|---|---|---|---|
| AA | TTTTTTTTTT_8 | TTTTTTTTTT8 | 3% | 100% |
| B1 | _8_8mUmUmU_8_8 | 88mUmUmU88 | n/a | 38%, 23% |
| B2 | _8_8/iBNA-T//iBNA-T//iBNA-T/_8_8 | 88/iBNA-T//iBNA-T//iBNA-T/88 | n/a | 42% |
| B3 | _8_8T_8_8 | 88T88 | n/a | 16%, 19%, 16% |
| B4 | _8_8TT_8_8 | 88TT88 | 61% | 47%, 32%, 54%, 72% |
| B5 | _8TT_8_8 | 8TT88 | 88% | 30% |
| B6 | _8_8TT_8 | 88TT8 | 81% | 15% |

-continued

Results Table:

| Adapter Name | Spacer (schematic sequence) | Spacer sequence | 24 hr Stability (% Increase in Unbound DNA) | ATP turnover (% AA) |
|---|---|---|---|---|
| B7 | _8T_8T_8 | 8T8T8 | 99% | 20% |
| B8 | _8TT_9TT_8 | 8TT9TT8 | 41% | 23% |
| B9 | _8TT3TT_8 | 8TT3TT8 | 77% | 81% |
| B10 | _8T_8T_8T_8 | 8T8T8T8 | 36% | 26% |
| B11 | _8TT_8TT_8TT_8 | 8TT8TT8TT8 | 19% | 27% |
| B12 | 33_8_8TT_8_8 | 3388TT88 | 45% | 27% |
| B13 | 3333_8_8TT_8_8 | 333388TT88 | 34% | 28% |
| B14 | 3333_8TT_8TT_83_8 | 33338TT8TT838 | 10% | 21% |
| B15 | 33_8TT_8TT_83TT_8 | 338TT8TT83TT8 | 21% | 22% |
| B16 | 3333_8TT_8TT_83TT_8 | 33338TT8TT83TT8 | 22% | 24% |
| B17 | _8TT_8TT_8 | 8TT8TT8 | n/a | 18% |
| B18 | TT_8TT_8 | TT8TT8 | n/a | 31% |
| B19 | 3TT_8TT_8 | 3TT8TT8 | n/a | 23% |
| B20 | 333TT_8TT_8TT_8 | 333TT8TT8TT8 | 23% | 26% |
| B21 | 333TT_8TT_8 | 333TT8TT8 | 24% | 26% |
| B22 | 3TT_8TT_8TT_8 | 3TT8TT8TT8 | 35% | 42% |
| B23 | TT3TT33333_8 | TT3TT333338 | 20% | 65% |
| B24 | 3TT3TT3333_8 | 3TT3TT33338 | 18% | 61% |
| B25 | 33TT3TT333_8 | 33TT3TT3338 | 25% | 76% |
| B26 | 333TT3TT33_8 | 333TT3TT338 | 24% | 66% |
| B27 | 3333TT3TT3_8 | 3333TT3TT38 | 19% | 71% |
| B28 | 33333TT3TT_8 | 33333TT3TT8 | 18% | 92% |
| B29 | TT33TT3333_8 | TT33TT33338 | 7% | 11%, 7% |
| B30 | 3TT33TT333_8 | 3TT33TT3338 | 14% | 11%, 9% |
| B31 | 33TT33TT33_8 | 33TT33TT338 | 7% | 20%, 19% |
| B32 | 3333TT33TT_8 | 3333TT33TT8 | 13% | 16%, 14% |
| B33 | TT333TT333_8 | TT333TT3338 | 48% | 46% |
| B34 | 3TT333TT33_8 | 3TT333TT338 | 52% | 53%, 38% |
| B35 | 33TT333TT3_8 | 33TT333TT38 | 41% | 50%, 47% |
| B36 | TT3333TT33_8 | TT3333TT338 | 52% | 53%, 45% |
| B37 | 3TT3333TT3_8 | 3TT3333TT38 | 46% | 54% |
| B38 | 33TT3333TT_8 | 33TT3333TT8 | 61% | 57% |
| B39 | TT33333TT3_8 | TT33333TT38 | 61% | 53% |
| B40 | 3TT33333TT_8 | 3TT33333TT8 | 59% | 53% |
| B41 | TT33333TT3_8 | TT333333TT8 | 51% | 52% |
| B42 | TT_8TT33333_8 | TT8TT333338 | 27% | 12% |
| B43 | 3TT_8TT3333_8 | 3TT8TT33338 | 26% | 10% |
| B44 | 33TT_8TT333_8 | 33TT8TT3338 | 17% | 27% |
| B45 | 333TT_8TT33_8 | 333TT8TT338 | 19% | 17% |
| B46 | 3333TT_8TT3_8 | 3333TT8TT38 | 16% | 12% |
| B47 | 33333TT_8TT_8 | 33333TT8TT8 | 6% | 65% |
| B48 | 333TT33TT_9 | 333TT33TT9 | 6% | 7% |
| B49 | 333TTmUmUmUTT_8 | 333TTmUmUmUTT8 | 8% | 33% |
| B50 | 333TTSpSpTT_8 | 333TTSpSpTT8 | 5% | 91% |
| B51 | 333TTSpTT_8 | 333TTSpTT8 | 9% | 95% |
| B52 | 333TTmUmUTT_8 | 333TTmUmUTT8 | 8% | 24% |

8 = spacer 18 (iSp18): $[(OCH_2CH_2)_6OPO_3]$
3 = C3: $(OC_3H_6OPO_3)$
9 = spacer 9 (iSp9): $[(OCH_2CH_2)_3OPO_3]$
T = thymidine
mU = 2'-O-Methyl uridine
IBNA-T = BNA (bridged nucleic acid) backbone with thymidine base
rU = RNA backbone with uridine base
Sp = d-spacer (DNA abasic site)

Example 3

This Example demonstrates that a motor protein can be loaded directly onto the spacer of a polynucleotide adapter when the blocking moiety ("Blocking Strand") is already in place.

A polynucleotide adapter was prepared having Top Strand, Bottom Strand and Blocking Strand sequences as described above in Example 2. The Top Strand comprised a spacer sequence comprising multiple nucleotide islands, such as described herein.

The polynucleotide strands comprising the adapter were assembled by annealing the strands in potassium acetate buffer (400 mM HEPES pH8.0, 400 mM Potassium Acetate) at the following concentrations:

| | Volume (μL) | Final Concentration |
|---|---|---|
| Top Strand | 20 | 10 μM |
| Blocker strand | 22 | 11 μM |
| Bottom Strand | 22 | 11 μM |
| 1x KOAc buffer | 100 | 0.5x |
| Nuclease Free Water | 36 | — |
| Total | 200 | |

Motor protein (Dda helicase) was combined with annealed adapter at a final concentration of 50-500 nM DNA and in varying degrees of molar excess protein under ambient conditions for 10-20 minutes. TMAD (100 μM) in potassium acetate buffer (as above) was added and incubated at 35° C. for one hour. Salt/ATP buffer (final concentration: 0.5M NaCl, 1 mM ATP, 10 mM MgCl2) was added and the mixture incubated at room temperature for 25-30 minutes.

Adapters with bound helicase underwent HPLC purification and adapter production was verified using a TBE gel.

Figure 2:
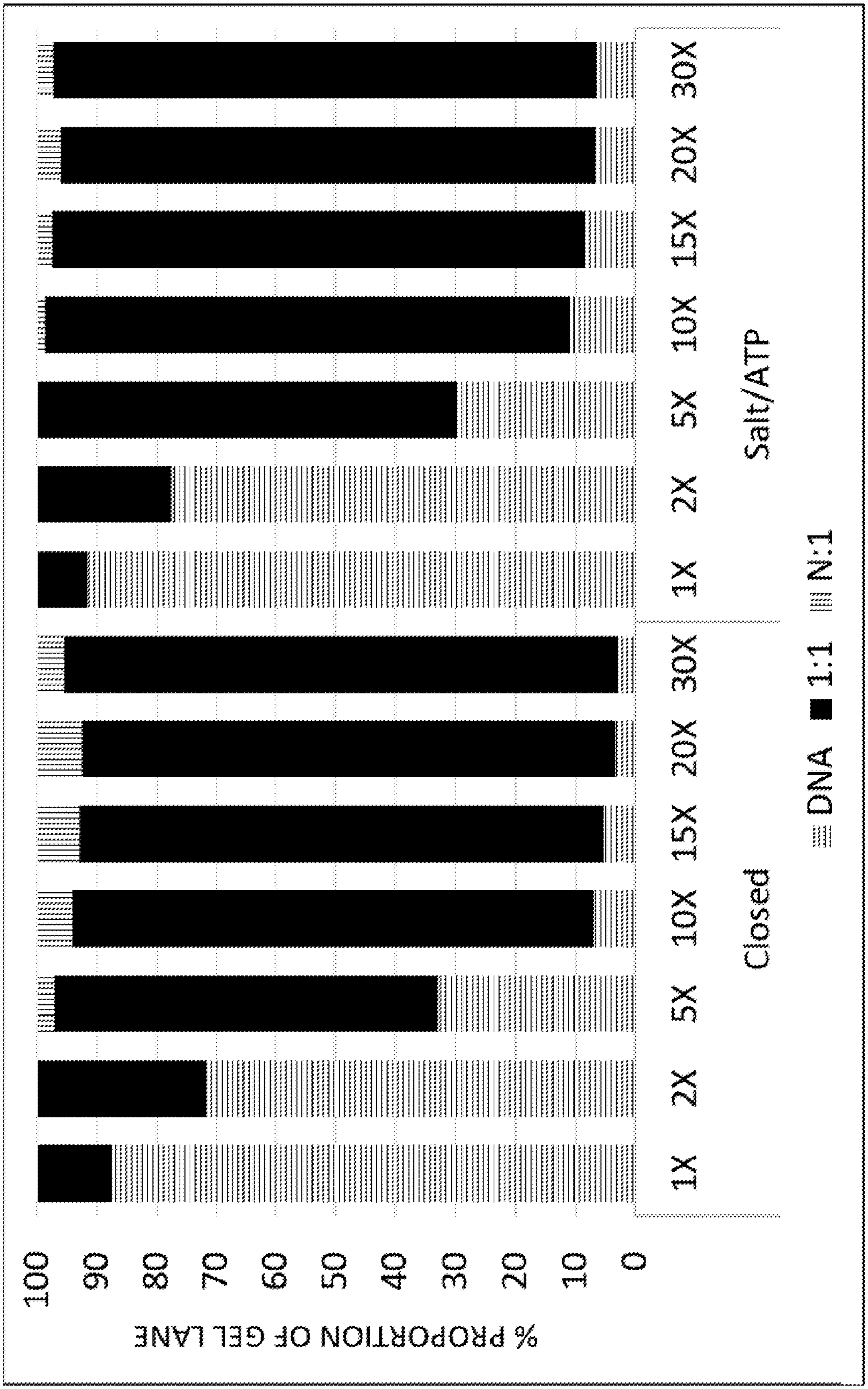
FIG. 2. Results of a loading titration showing effective stalling of a motor protein on an adapter comprising a spacer as defined herein. This data is discussed in Example 3.

Samples prepared with excess motor protein at 1×, 2×, 5×, 10×, 15×, 20× and 30× were run on a gel, with results depicted in FIG. 2. Samples were obtained from both before ("closed") and after ("Salt/ATP") the step of adding salt/ATP buffer.

The lanes show that the following were obtained: free DNA (adapter without motor protein loaded); motor protein and adapter DNA at a ratio of 1:1, indicating correctly loaded motor protein; and a small amount of motor protein and adapter DNA at ratios greater than 1:1, where multiple motor proteins have initially loaded onto a single adapter. The greater the excess of motor protein to DNA adapter, the greater the proportion of loaded adapter (1:1 protein:DNA) was obtained.

The results presented in FIG. 2 therefore demonstrate that a motor protein can be loaded directly onto a spacer section comprising DNA islands as described herein.

Example 4

This Example demonstrates the increased efficiency obtained when example adapters prepared according to the methods described herein are tested in a DNA sequencing system.

A double stranded 440 mer library was prepared with a commercially-available Oxford Nanopore sequencing kit (SQK-LSK109), using either the standard commercially-available sequencing adapter (AMX) or a test adapter (adapters named herein as B14, B21, C1).

The test adapters were as described above in Example 2 and prepared accordingly. Spacer sequences were as follows:

B14: 33338TT8TT838

B21: 333TT8TT8

C1: 333TT33TT8.

The 440 mer library was sequenced on a MinION flowcell (FLO-MIN106) using the Oxford Nanopore MinION Mklb device. Data collection was performed by MinKNOW software using baseline LSK109 sequencing protocol.

Bulk Fast5 data produced by MiniKNOW software was analysed, individual strand data was extracted and stored in subsequent text file. The strand data was used to estimate the speed of DNA translocation using number of events in a strand and duration of strand.

Figure 3:
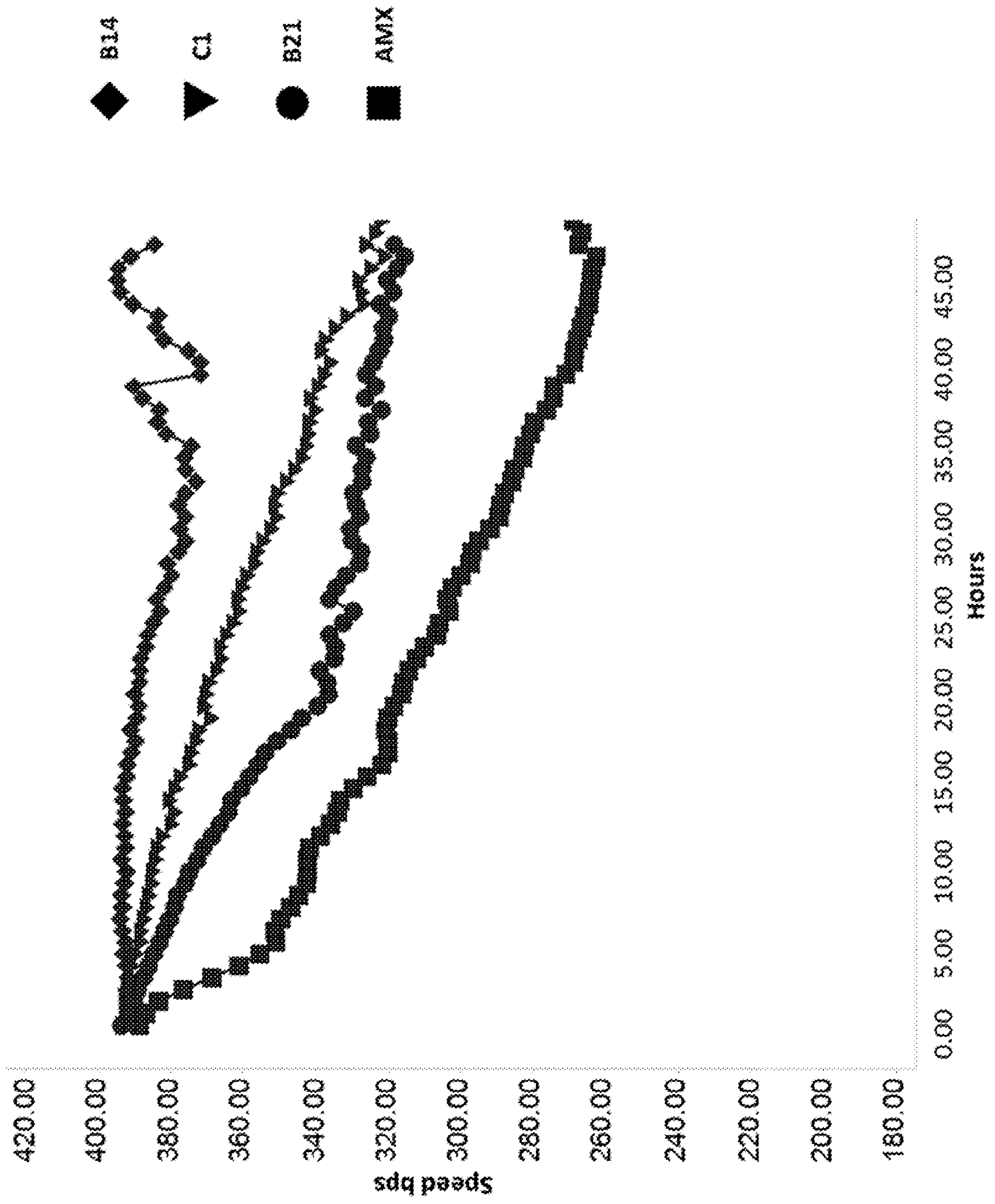
FIG. 3. Results showing increased efficiency obtained when example adapters according to the methods described herein are tested in a DNA sequencing system as compared to adapters lacking a spacer as described herein. This data is discussed in Example 4.

The results presented in FIG. 3 show that the improved fuel efficiency of the tested adapters (B14, B20 and C1) enabled sequencing to continue at a faster rate for longer than with the commercially-available adapter AMX. The results also confirm the stability of the tested adapters in a nanopore sequencing system.

Description of the Sequence Listing

SEQ ID NO: 1 shows the amino acid sequence of (hexa-histidine tagged) exonuclease I (EcoExo I) from *E. coli.*

SEQ ID NO: 2 shows the amino acid sequence of the exonuclease III enzyme from *E. coli.*

SEQ ID NO: 3 shows the amino acid sequence of the RecJ enzyme from *T. thermophilus* (TthRecJ-cd).

SEQ ID NO: 4 shows the amino acid sequence of bacteriophage lambda exonuclease. The sequence is one of three identical subunits that assemble into a trimer. (http://www.neb.com/nebecomm/products/productM0262.asp).

SEQ ID NO: 5 shows the amino acid sequence of Phi29 DNA polymerase from *Bacillus subtilis* phage Phi29.

SEQ ID NO: 6 shows the amino acid sequence of Trwc Cba (*Citromicrobium bathyomarinum*) helicase.

SEQ ID NO: 7 shows the amino acid sequence of Hel308 Mbu (*Methanococcoides burtonii*) helicase.

SEQ ID NO: 8 shows the amino acid sequence of the Dda helicase 1993 from Enterobacteria phage T4.

SEQ ID NO: 9: shows the nucleotide sequence of a polynucleotide strand discussed in example 1.

SEQ ID NO: 10: shows the nucleotide sequence of a polynucleotide strand discussed in example 1 ("Test" strand).

SEQ ID NO: 11: shows the nucleotide sequence of a polynucleotide strand discussed in example 1.

SEQ ID NO: 12: shows the nucleotide sequence of a polynucleotide strand discussed in example 1 ("Test −10" strand).

SEQ ID NO: 13 shows the nucleotide sequence of a polynucleotide adapter discussed in example 2 ("top strand").

SEQ ID NO: 14 shows the nucleotide sequence of a polynucleotide adapter discussed in example 2 ("top strand", portion preceding the spacer unit).

SEQ ID NO: 15 shows the nucleotide sequence of a polynucleotide adapter discussed in example 2 ("top strand", portion preceding the spacer unit; nucleotide region).

SEQ ID NO: 16 shows the nucleotide sequence of a polynucleotide adapter discussed in example 2 ("top strand", portion following the spacer unit).

SEQ ID NO: 17 shows the nucleotide sequence of a polynucleotide adapter discussed in example 2 ("bottom strand").

SEQ ID NO: 18 shows the nucleotide sequence of a polynucleotide adapter discussed in example 2 ("loading strand").

SEQ ID NO: 19 shows the nucleotide sequence of a polynucleotide adapter discussed in example 2 ("blocking strand").

SEQUENCE LISTING
- exonuclease I from *E. coli*

SEQ ID NO: 1

MMNDGKQQSTFLFHDYETFGTHPALDRPAQFAAIRTDSEFNVIGEPEVFYCKPADDYLPQ

PGAVLITGITPQEARAKGENEAAFAARIHSLFTVPKTCILGYNNVREDDEVTRNIFYRNF

YDPYAWSWQHDNSRWDLLDVMRACYALRPEGINWPENDDGLPSFRLEHLTKANGIEHSNA

HDAMADVYATIAMAKLVKTRQPRLFDYLFTHRNKHKLMALIDVPQMKPLVHVSGMFGAWR

-continued

GNTSWVAPLAWHPENRNAVIMVDLAGDISPLLELDSDTLRERLYTAKTDLGDNAAVPVKL

VHINKCPVLAQANTLRPEDADRLGINRQHCLDNLKILRENPQVREKVVAIFAEAEPFTPS

DNVDAQLYNGFFSDADRAAMKIVLETEPRNLPALDITFVDKRIEKLLENYRARNFPGTLD

YAEQQRWLEHRRQVFTPEFLQGYADELQMLVQQYADDKEKVALLKALWQYAEEIVSGSGH

HHHHH

- exonuclease III enzyme from *E. coli*

SEQ ID NO: 2

MKFVSFNINGLRARPHQLEAIVEKHQPDVIGLQETKVHDDMFPLEEVAKLGYNVFYHGQK

GHYGVALLTKETPIAVRRGFPGDDEEAQRRIIMAEIPSLLGNVTVINGYFPQGESRDHPI

KFPAKAQFYQNLQNYLETELKRDNPVLIMGDMNISPTDLDIGIGEENRKRWLRTGKCSFL

PEEREWMDRLMSWGLVDTFRHANPQTADRFSWFDYRSKGFDDNRGLRIDLLLASQPLAEC

CVETGIDYEIRSMEKPSDHAPVWATERR

- RecJ enzyme from *T. thermophilus*

SEQ ID NO: 3

MFRRKEDLDPPLALLPLKGLREAAALLEEALRQGKRIRVHGDYDADGLIGTAILVRGLAA

LGADVHPFIPHRLEEGYGVLMERVPEHLEASDLFLTVDCGITNHAELRELLENGVEVIVT

DHHTPGKTPPPGLVVHPALTPDLKEKPTGAGVAFLLLWALHERLGLPPPLEYADLAAVGT

IADVAPLWGWNRALVKEGLARIPASSWVGLRLLAEAVGYTGKAVEVAFRIAPRINAASRL

GEAEKALRLLLTDDAAEAQALVGELHRLNARRQTLEEAMLRKLLPQADPEAKAIVLLDPE

GHPGVMGIVASRILEATLRPVFLVAQGKGTVRSLAPISAVEALRSAEDLLLRYGGHKEAA

GFAMDEALFPAFKARVEAYAARFPDPVREVALLDLLPEPGLLPQVFRELALLEPYGEGNP

EPLFL

- bacteriophage lambda exonuclease

SEQ ID NO: 4

MTPDIILQRTGIDVRAVEQGDDAWHKLRLGVITASEVHNVIAKPRSGKKWPDMKMSYFHT

LLAEVCTGVAPEVNAKALAWGKQYENDARTLFEFTSGVNVTESPITYRDESMRTACSPDG

LCSDGNGLELKCPFTSRDFMKFRLGGFEAIKSAYMAQVQYSMWVTRKNAWYFANYDPRMK

REGLHYVVIERDEKYMASFDEIVPEFIEKMDEALAEIGFVFGEQWR

- Phi29 DNA polymerase

SEQ ID NO: 5

MKHMPRKMYSCAFETTTKVEDCRVWAYGYMNIEDHSEYKIGNSLDEFMAWVLKVQADLYF

HNLKFDGAFIINWLERNGFKWSADGLPNTYNTIISRMGQWYMIDICLGYKGKRKIHTVIY

DSLKKLPFPVKKIAKDFKLTVLKGDIDYHKERPVGYKITPEEYAYIKNDIQIIAEALLIQ

FKQGLDRMTAGSDSLKGFKDIITTKKFKKVFPTLSLGLDKEVRYAYRGGFTWLNDRFKEK

EIGEGMVFDVNSLYPAQMYSRLLPYGEPIVFEGKYVWDEDYPLHIQHIRCEFELKEGYIP

TIQIKRSRFYKGNEYLKSSGGEIADLWLSNVDLELMKEHYDLYNVEYISGLKFKATTGLF

KDFIDKWTYIKTTSEGAIKQLAKLMLNSLYGKFASNPDVTGKVPYLKENGALGFRLGEEE

TKDPVYTPMGVFITAWARYTTITAAQACYDRIIYCDTDSIHLTGTEIPDVIKDIVDPKKL

GYWAHESTFKRAKYLRQKTYIQDIYMKEVDGKLVEGSPDDYTDIKFSVKCAGMTDKIKKE

VTFENFKVGFSRKMKPKPVQVPGGVVLVDDTFTIKSGGSAWSHPQFEKGGGSGGGSGGSA

WSHPQFEK

- Trwc Cba helicase

SEQ ID NO: 6

MLSVANVRSPSAAASYFASDNYYASADADRSGQWIGDGAKRLGLEGKVEARAFDALLRGE

LPDGSSVGNPGQAHRPGTDLTFSVPKSWSLLALVGKDERIIAAYREAVVEALHWAEKNAA

-continued

ETRVVEKGMVVTQATGNLAIGLFQHDTNRNQEPNLHFHAVIANVTQGKDGKWRTLKNDRL

WQLNTTLNSIAMARFRVAVEKLGYEPGPVLKHGNFEARGISREQVMAFSTRRKEVLEARR

GPGLDAGRIAALDTRASKEGIEDRATLSKQWSEAAQSIGLDLKPLVDRARTKALGQGMEA

TRIGSLVERGRAWLSRFAAHVRGDPADPLVPPSVLKQDRQTIAAAQAVASAVRHLSQREA

AFERTALYKAALDFGLPTTIADVEKRTRALVRSGDLIAGKGEHKGWLASRDAVVTEQRIL

SEVAAGKGDSSPAITPQKAAASVQAAALTGQGERLNEGQLAAARLILISKDRTIAVQGIA

GAGKSSVLKPVAEVLRDEGHPVIGLAIQNTLVQMLERDTGIGSQTLARFLGGWNKLLDDP

GNVALRAEAQASLKDHVLVLDEASMVSNEDKEKLVRLANLAGVHRLVLIGDRKQLGAVDA

GKPFALLQRAGIARAEMATNLRARDPVVREAQAAAQAGDVRKALRHLKSHTVEARGDGAQ

VAAETWLALDKETRARTSIYASGRAIRSAVNAAVQQGLLASREIGPAKMKLEVLDRVNTT

REELRHLPAYRAGRVLEVSRKQQALGLFIGEYRVIGQDRKGKLVEVEDKRGKRFREDPAR

IRAGKGDDNLTLLEPRKLEIHEGDRIRWTRNDHRRGLFNADQARVVEIANGKVTFETSKG

DLVELKKDDPMLKRIDLAYALNVHMAQGLISDRGIAVMDSRERNLSNQKTFLVTVTRLRD

HLTLVVDSADKLGAAVARNKGEKASAIEVTGSVKPTATKGSGVDQPKSVEANKAEKELTR

SKSKTLDFGI

- Hel308 Mbu helicase

SEQ ID NO: 7

MMIRELDIPRDIIGFYEDSGIKELYPPQAEAIEMGLLEKKNLLAAIPTASGKTLLAELAM

IKAIREGGKALYIVPLRALASEKFERFKELAPFGIKVGISTGDLDSRADWLGVNDIIVAT

SEKTDSLLRNGTSWMDEITTVVVDEIHLLDSKNRGPTLEVTITKLMRLNPDVQVVALSAT

VGNAREMADWLGAALVLSEWRPTDLHEGVLFGDAINFPGSQKKIDRLEKDDAVNLVLDTI

KAEGGQCLVFESSRRNCAGFAKTASSKVAKILDNDIMIKLAGIAEEVESTGETDTAIVLAN

CIRKGVAFHHAGLNSNHRKLVENGFRQNLIKVISSTPTLAAGLNLPARRVIIRSYRRFDS

NFGMQPIPVLEYKQMAGRAGRPHLDPYGESVLLAKTYDEFAQLMENYVEADAEDIWSKLG

TENALRTHVLSTIVNGFASTRQELFDFFGATFFAYQQDKWMLEEVINDCLEFLIDKAMVS

ETEDIEDASKLFLRGTRLGSLVSMLYIDPLSGSKIVDGFKDIGKSTGGNMGSLEDDKGDD

ITVTDMTLLHLVCSTPDMRQLYLRNTDYTIVNEYIVAHSDEFHEIPDKLKETDYEWFMGE

VKTAMLLEEWVTEVSAEDITRHFNVGEGDIHALADTSEWLMHAAAKLAELLGVEYSSHAY

SLEKRIRYGSGLDLMELVGIRGVGRVRARKLYNAGFVSVAKLKGADISVLSKLVGPKVAY

NILSGIGVRVNDKHENSAPISSNTLDTLLDKNQKTENDFQ

- Dda helicase

SEQ ID NO: 8

MTFDDLTEGQKNAFNIVMKAIKEKKHHVTINGPAGTGKTTLTKFIIEALISTGETGIILA

APTHAAKKILSKLSGKEASTIHSILKINPVTYEENVLFEQKEVPDLAKCRVLICDEVSMY

DRKLFKILLSTIPPWCTIIGIGDNKQIRPVDPGENTAYISPFFTHKDFYQCELTEVKRSN

APIIDVATDVRNGKWIYDKVVDGHGVRGFTGDTALRDFMVNYFSIVKSLDDLFENRVMAF

TNKSVDKLNSIIRKKIFETDKDFIVGEIIVMQEPLFKTYKIDGKPVSEIIFNNGQLVRII

EAEYTSTFVKARGVPGEYLIRHWDLTVETYGDDEYYREKIKIISSDEELYKFNLFLGKTA

ETYKNWNKGGKAPWSDFWDAKSQFSKVKALPASTFHKAQGMSVDRAFIYTPCIHYADVEL

AQQLLYVGVTRGRYDVFYV

-continued

SEQ ID NO: 9
/5Biosg/CCTTTTTTTT GGCGTCTGCTTGGGTGTTTAACC/iSp18//iSp18// iSp18//iSp18//iBNA-C//iBNA-C//iBNA-A//iBNA-C//iBNA-A/

ACTTCGTTCAGTTACGTATTGC/3Bio/

SEQ ID NO: 10
GGTTAAACACCCAAGCAGACGCCAAAAAAAAGG

SEQ ID NO: 11
/5phos/GCAATACGTAACTGAACGAAGT/iBNA-T//iBNA-G//iBNA-T//iBNA-

G//iBNA-G/

SEQ ID NO: 12
CCAAGCAGACGCC AAAAAAAAGG

SEQ ID NO: 13
333333333333333333333333333333CCTTTTTTTTGGCGTCTGCTTGGGTGTTT

AACC/[spacer sequence]/CCACAACTTCGTTCAGTTACGTATTGCT

SEQ ID NO: 14
333333333333333333333333333333CCTTTTTTTTGGCGTCTGCTTGGGTGTT-
TAACC

SEQ ID NO: 15
CCTTTTTTTTGGCGTCTGCTTGGGTGTTTAACC

SEQ ID NO: 16
CCACAACTTCGTTCAGTTACGTATTGCT

SEQ ID NO: 17
5phos/GCAATACGTAACTGAACGAAGTTGTGG

SEQ ID NO: 18
GGTTAAACACCCAAGCAGACGCCTTT

SEQ ID NO: 19
GGTTAAACACCCAAGCAGACGCCAAAAAAAAGG/3Cy5Sp/

---

The invention claimed is:

1. A method of loading a motor protein onto a polynucleotide adapter, the method comprising:

i) providing a polynucleotide adapter comprising a loading site connected to a spacer;

ii) contacting the loading site with a motor protein;

iii) causing the motor protein to progress from the loading site onto the spacer; and iv) binding a blocking moiety to the polynucleotide adapter, wherein the blocking moiety prevents the motor protein from moving off the spacer and back onto the loading site.

2. The method according to claim 1, wherein in step (ii) the motor protein engages with the loading site; and in step (iv) the blocking moiety prevents the motor protein re-engaging with the loading site.

3. The method according to claim 1, wherein the motor protein is a first motor protein and causing the first motor protein to progress from the loading site onto the spacer comprises loading a second motor protein onto the loading site and causing the second motor protein to progress from the loading site towards the spacer, wherein the second motor protein forces the first motor protein onto the spacer.

4. The method according to claim 1, wherein binding the blocking moiety to the polynucleotide adapter forces the motor protein onto the spacer.

5. The method according to claim 1, wherein the polynucleotide adapter comprises a loading site connected to the spacer and the blocking moiety is bound to the loading site adjacent to the spacer; optionally wherein the loading site is contiguous with the spacer and the blocking moiety is bound to the loading site immediately adjacent to the spacer.

6. The method according to claim 1, wherein step (iii) comprises causing the motor protein to progress onto the spacer such that the spacer occupies the active site of the motor protein.

7. The method according to claim 1, wherein the loading site comprises a single-stranded polynucleotide; optionally wherein the loading site comprises a single-stranded polynucleotide having a length of between about 2 and about 1000 nucleotide units.

8. The method according to claim 1, wherein the blocking moiety sterically prevents the movement of the motor protein off the spacer.

9. The method according to claim 5, wherein the blocking moiety comprises a single-stranded polynucleotide hybridised to the loading site.

10. The method according to claim 1, wherein the blocking moiety comprises a single-stranded polynucleotide having a length of between about 2 and about 1000 nucleotide units.

11. A method according to claim 1, wherein the spacer comprises one or more nitroindoles, one or more inosines, one or more acridines, one or more 2-aminopurines, one or more 2-6-diaminopurines, one or more 5-bromo-deoxyuridines, one or more inverted thymidines (inverted dTs), one or more inverted dideoxy-thymidines (ddTs), one or more dideoxy-cytidines (ddCs), one or more 5-methylcytidines, one or more 5-hydroxymethylcytidines, one or more 2'-O-Methyl RNA bases, one or more Iso-deoxycytidines (Iso-dCs), one or more Iso-deoxyguanosines (Iso-dGs), one or more C3 (OC3H6OPO3) groups, one or more photo-cleavable (PC) [OC3H6-C(O) NHCH2-C6H3NO2-CH(CH3) OPO3] groups, one or more hexandiol groups, one or more spacer 9 (iSp9) [(OCH2CH2) 30PO3] groups, or one or more spacer 18 (iSp18) [(OCH2CH2)6OPO3] groups.

12. A method according to claim 1, wherein:

the spacer comprises one or more nucleotides, or one or more nucleotide islands; and positioning the motor protein on the spacer comprises contacting the motor protein with the spacer and modifying the motor protein to prevent the motor protein disengaging from the spacer.

13. The method according to claim 1 wherein the spacer comprises one or more moieties formed by one or more spacer units and one or more nucleotides, and wherein the one or more moieties is selected from the group consisting of: —S—N—S—N—S—N—S—; —S—N—N—S—N—N—S—N—N—S—; —S—S—S—S—S—S—N—N—S—S—; —S—S—S—S—S—N—N—S—N—N—S—S—S—; —S—S—S—N—N—S—N—N—S—S—N—N—S—; —S—S—S—S—S—N—N—S—N—N—S—S—N—N—S—; —S—S—S—N—N—S—N—N—S—N—N—S—; —N—N—S—S—N—N—S—S—S—S—S—; —S—N—N—S—S—N—N—S—S—S—S—; —S—S—N—N—S—S—N—N—S—S—S—; —S—S—S—S—N—N—S—S—N—N—S—; —N—N—S—N—N—S—S—S—S—S—S—; —S—N—N—S—N—N—S—S—S—S—S—; —S—S—N—N—S—N—N—S—S—S—S—; —S—S—S—N—N—S—N—N—S—S—S—:—S—S—S—S—N—N—S—N—N—S—S—; and —S—S—S—N—N—S—S—N—N—S—; wherein each S is a spacer unit and each N is a nucleotide.

14. The method according to claim 1, wherein the motor protein is a helicase, a polymerase, an exonuclease, a topoisomerase, or a variant thereof: optionally wherein the motor protein is a helicase selected from a Hel308 helicase, a RecD helicase, a TraI helicase, a TrwC helicase, an XPD helicase, and a Dda helicase, or a variant thereof.

15. The method according to claim 1, wherein the motor protein on the spacer of the polynucleotide adapter is modified to prevent the motor protein disengaging from the spacer.

16. A method of controlling the movement of a target polynucleotide with respect to a transmembrane nanopore, comprising:

providing (A) a target polynucleotide; (B) a polynucleotide adapter comprising a spacer;

and (C) a motor protein;

carrying out a method according to claim 3 thereby stalling the motor protein on the spacer of the polynucleotide adapter;

contacting the target polynucleotide and the stalled motor protein on the spacer of the polynucleotide adapter with the nanopore; and applying a potential across the transmembrane nanopore thereby causing the motor protein to move past the spacer onto the target polynucleotide thereby controlling the movement of the target polynucleotide with respect to the nanopore.

17. The method according to claim 16 wherein:

(i) the motor protein is stalled on the polynucleotide adapter before the polynucleotide adapter is attached to the target polynucleotide; or (ii) the polynucleotide adapter is attached to the target polynucleotide before the motor protein is stalled on the polynucleotide adapter.

18. A method of controlling the movement of a target polynucleotide with respect to a transmembrane nanopore, comprising:

i) providing a target polynucleotide;

ii) providing a polynucleotide adapter comprising a spacer and having a motor protein stalled thereon, wherein said polynucleotide adapter is obtained according to the method of claim 3;

iii) contacting the target polynucleotide and the polynucleotide adapter with the nanopore; and iv) applying a potential across the transmembrane nanopore thereby causing the motor protein to move past the spacer onto the target polynucleotide thereby controlling the movement of the target polynucleotide with respect to the nanopore.

19. A method of characterising a target polynucleotide, comprising:

i) carrying out the method of claim 1; and ii) taking one or more measurements as the target polynucleotide moves with respect to the nanopore, wherein the one or more measurements are indicative of one or more characteristics of the target polynucleotide, and thereby characterising the target polynucleotide as it moves with respect to the nanopore.

20. The method according to claim 7, wherein (i) the blocking moiety comprises a single-stranded polynucleotide; and (ii) binding the blocking moiety to the loading site comprises hybridising the blocking moiety to the loading site.

21. The method according to claim 1, wherein the spacer comprises one or more abasic nucleotides.

22. The method according to claim 3, wherein the spacer comprises one or more nucleotides of different backbone structure to the loading site.

23. The method according to claim 3, wherein the spacer comprises one or more nucleotides.

* * * * *

SEQUENCE LISTING

<160> NUMBER OF SEQ ID NOS: 19

<210> SEQ ID NO 1
<211> LENGTH: 485
<212> TYPE: PRT
<213> ORGANISM: Escherichia coli

<400> SEQUENCE: 1

```
Met Met Asn Asp Gly Lys Gln Gln Ser Thr Phe Leu Phe His Asp Tyr
1               5                   10                  15

Glu Thr Phe Gly Thr His Pro Ala Leu Asp Arg Pro Ala Gln Phe Ala
            20                  25                  30

Ala Ile Arg Thr Asp Ser Glu Phe Asn Val Ile Gly Glu Pro Glu Val
        35                  40                  45

Phe Tyr Cys Lys Pro Ala Asp Asp Tyr Leu Pro Gln Pro Gly Ala Val
    50                  55                  60

Leu Ile Thr Gly Ile Thr Pro Gln Glu Ala Arg Ala Lys Gly Glu Asn
65                  70                  75                  80

Glu Ala Ala Phe Ala Ala Arg Ile His Ser Leu Phe Thr Val Pro Lys
                85                  90                  95

Thr Cys Ile Leu Gly Tyr Asn Asn Val Arg Phe Asp Asp Glu Val Thr
            100                 105                 110

Arg Asn Ile Phe Tyr Arg Asn Phe Tyr Asp Pro Tyr Ala Trp Ser Trp
        115                 120                 125
```

```
Gln His Asp Asn Ser Arg Trp Asp Leu Leu Asp Val Met Arg Ala Cys
    130                 135                 140

Tyr Ala Leu Arg Pro Glu Gly Ile Asn Trp Pro Glu Asn Asp Asp Gly
145                 150                 155                 160

Leu Pro Ser Phe Arg Leu Glu His Leu Thr Lys Ala Asn Gly Ile Glu
                165                 170                 175

His Ser Asn Ala His Asp Ala Met Ala Asp Val Tyr Ala Thr Ile Ala
            180                 185                 190

Met Ala Lys Leu Val Lys Thr Arg Gln Pro Arg Leu Phe Asp Tyr Leu
        195                 200                 205

Phe Thr His Arg Asn Lys His Lys Leu Met Ala Leu Ile Asp Val Pro
    210                 215                 220

Gln Met Lys Pro Leu Val His Val Ser Gly Met Phe Gly Ala Trp Arg
225                 230                 235                 240

Gly Asn Thr Ser Trp Val Ala Pro Leu Ala Trp His Pro Glu Asn Arg
                245                 250                 255

Asn Ala Val Ile Met Val Asp Leu Ala Gly Asp Ile Ser Pro Leu Leu
            260                 265                 270

Glu Leu Asp Ser Asp Thr Leu Arg Glu Arg Leu Tyr Thr Ala Lys Thr
        275                 280                 285

Asp Leu Gly Asp Asn Ala Ala Val Pro Val Lys Leu Val His Ile Asn
    290                 295                 300

Lys Cys Pro Val Leu Ala Gln Ala Asn Thr Leu Arg Pro Glu Asp Ala
305                 310                 315                 320

Asp Arg Leu Gly Ile Asn Arg Gln His Cys Leu Asp Asn Leu Lys Ile
                325                 330                 335

Leu Arg Glu Asn Pro Gln Val Arg Glu Lys Val Val Ala Ile Phe Ala
            340                 345                 350

Glu Ala Glu Pro Phe Thr Pro Ser Asp Asn Val Asp Ala Gln Leu Tyr
        355                 360                 365

Asn Gly Phe Phe Ser Asp Ala Asp Arg Ala Ala Met Lys Ile Val Leu
    370                 375                 380

Glu Thr Glu Pro Arg Asn Leu Pro Ala Leu Asp Ile Thr Phe Val Asp
385                 390                 395                 400

Lys Arg Ile Glu Lys Leu Leu Phe Asn Tyr Arg Ala Arg Asn Phe Pro
                405                 410                 415

Gly Thr Leu Asp Tyr Ala Glu Gln Gln Arg Trp Leu Glu His Arg Arg
            420                 425                 430

Gln Val Phe Thr Pro Glu Phe Leu Gln Gly Tyr Ala Asp Glu Leu Gln
        435                 440                 445

Met Leu Val Gln Gln Tyr Ala Asp Asp Lys Glu Lys Val Ala Leu Leu
    450                 455                 460

Lys Ala Leu Trp Gln Tyr Ala Glu Glu Ile Val Ser Gly Ser Gly His
465                 470                 475                 480

His His His His His
                485
```

<210> SEQ ID NO 2
<211> LENGTH: 268
<212> TYPE: PRT
<213> ORGANISM: Escherichia coli

<400> SEQUENCE: 2

```
Met Lys Phe Val Ser Phe Asn Ile Asn Gly Leu Arg Ala Arg Pro His
1               5                   10                  15
```

```
Gln Leu Glu Ala Ile Val Glu Lys His Gln Pro Asp Val Ile Gly Leu
            20                  25                  30

Gln Glu Thr Lys Val His Asp Asp Met Phe Pro Leu Glu Glu Val Ala
        35                  40                  45

Lys Leu Gly Tyr Asn Val Phe Tyr His Gly Gln Lys Gly His Tyr Gly
    50                  55                  60

Val Ala Leu Leu Thr Lys Glu Thr Pro Ile Ala Val Arg Arg Gly Phe
65                  70                  75                  80

Pro Gly Asp Asp Glu Glu Ala Gln Arg Arg Ile Ile Met Ala Glu Ile
                85                  90                  95

Pro Ser Leu Leu Gly Asn Val Thr Val Ile Asn Gly Tyr Phe Pro Gln
            100                 105                 110

Gly Glu Ser Arg Asp His Pro Ile Lys Phe Pro Ala Lys Ala Gln Phe
        115                 120                 125

Tyr Gln Asn Leu Gln Asn Tyr Leu Glu Thr Glu Leu Lys Arg Asp Asn
    130                 135                 140

Pro Val Leu Ile Met Gly Asp Met Asn Ile Ser Pro Thr Asp Leu Asp
145                 150                 155                 160

Ile Gly Ile Gly Glu Glu Asn Arg Lys Arg Trp Leu Arg Thr Gly Lys
                165                 170                 175

Cys Ser Phe Leu Pro Glu Glu Arg Glu Trp Met Asp Arg Leu Met Ser
            180                 185                 190

Trp Gly Leu Val Asp Thr Phe Arg His Ala Asn Pro Gln Thr Ala Asp
        195                 200                 205

Arg Phe Ser Trp Phe Asp Tyr Arg Ser Lys Gly Phe Asp Asp Asn Arg
    210                 215                 220

Gly Leu Arg Ile Asp Leu Leu Leu Ala Ser Gln Pro Leu Ala Glu Cys
225                 230                 235                 240

Cys Val Glu Thr Gly Ile Asp Tyr Glu Ile Arg Ser Met Glu Lys Pro
                245                 250                 255

Ser Asp His Ala Pro Val Trp Ala Thr Phe Arg Arg
            260                 265
```

<210> SEQ ID NO 3
<211> LENGTH: 425
<212> TYPE: PRT
<213> ORGANISM: Thermus thermophilus

<400> SEQUENCE: 3

```
Met Phe Arg Arg Lys Glu Asp Leu Asp Pro Pro Leu Ala Leu Leu Pro
1               5                   10                  15

Leu Lys Gly Leu Arg Glu Ala Ala Ala Leu Leu Glu Glu Ala Leu Arg
            20                  25                  30

Gln Gly Lys Arg Ile Arg Val His Gly Asp Tyr Asp Ala Asp Gly Leu
        35                  40                  45

Thr Gly Thr Ala Ile Leu Val Arg Gly Leu Ala Ala Leu Gly Ala Asp
    50                  55                  60

Val His Pro Phe Ile Pro His Arg Leu Glu Glu Gly Tyr Gly Val Leu
65                  70                  75                  80

Met Glu Arg Val Pro Glu His Leu Glu Ala Ser Asp Leu Phe Leu Thr
                85                  90                  95

Val Asp Cys Gly Ile Thr Asn His Ala Glu Leu Arg Glu Leu Leu Glu
            100                 105                 110
```

```
Asn Gly Val Glu Val Ile Val Thr Asp His His Thr Pro Gly Lys Thr
        115                 120                 125

Pro Pro Pro Gly Leu Val Val His Pro Ala Leu Thr Pro Asp Leu Lys
    130                 135                 140

Glu Lys Pro Thr Gly Ala Gly Val Ala Phe Leu Leu Leu Trp Ala Leu
145                 150                 155                 160

His Glu Arg Leu Gly Leu Pro Pro Pro Leu Glu Tyr Ala Asp Leu Ala
                165                 170                 175

Ala Val Gly Thr Ile Ala Asp Val Ala Pro Leu Trp Gly Trp Asn Arg
            180                 185                 190

Ala Leu Val Lys Glu Gly Leu Ala Arg Ile Pro Ala Ser Ser Trp Val
        195                 200                 205

Gly Leu Arg Leu Leu Ala Glu Ala Val Gly Tyr Thr Gly Lys Ala Val
    210                 215                 220

Glu Val Ala Phe Arg Ile Ala Pro Arg Ile Asn Ala Ala Ser Arg Leu
225                 230                 235                 240

Gly Glu Ala Glu Lys Ala Leu Arg Leu Leu Leu Thr Asp Asp Ala Ala
                245                 250                 255

Glu Ala Gln Ala Leu Val Gly Glu Leu His Arg Leu Asn Ala Arg Arg
            260                 265                 270

Gln Thr Leu Glu Glu Ala Met Leu Arg Lys Leu Leu Pro Gln Ala Asp
        275                 280                 285

Pro Glu Ala Lys Ala Ile Val Leu Leu Asp Pro Glu Gly His Pro Gly
    290                 295                 300

Val Met Gly Ile Val Ala Ser Arg Ile Leu Glu Ala Thr Leu Arg Pro
305                 310                 315                 320

Val Phe Leu Val Ala Gln Gly Lys Gly Thr Val Arg Ser Leu Ala Pro
                325                 330                 335

Ile Ser Ala Val Glu Ala Leu Arg Ser Ala Glu Asp Leu Leu Leu Arg
            340                 345                 350

Tyr Gly Gly His Lys Glu Ala Ala Gly Phe Ala Met Asp Glu Ala Leu
        355                 360                 365

Phe Pro Ala Phe Lys Ala Arg Val Glu Ala Tyr Ala Ala Arg Phe Pro
    370                 375                 380

Asp Pro Val Arg Glu Val Ala Leu Leu Asp Leu Leu Pro Glu Pro Gly
385                 390                 395                 400

Leu Leu Pro Gln Val Phe Arg Glu Leu Ala Leu Leu Glu Pro Tyr Gly
                405                 410                 415

Glu Gly Asn Pro Glu Pro Leu Phe Leu
            420                 425


<210> SEQ ID NO 4
<211> LENGTH: 226
<212> TYPE: PRT
<213> ORGANISM: Bacteriophage lambda

<400> SEQUENCE: 4

Met Thr Pro Asp Ile Ile Leu Gln Arg Thr Gly Ile Asp Val Arg Ala
1               5                   10                  15

Val Glu Gln Gly Asp Asp Ala Trp His Lys Leu Arg Leu Gly Val Ile
            20                  25                  30

Thr Ala Ser Glu Val His Asn Val Ile Ala Lys Pro Arg Ser Gly Lys
        35                  40                  45
```

Lys Trp Pro Asp Met Lys Met Ser Tyr Phe His Thr Leu Leu Ala Glu
    50                  55                  60

Val Cys Thr Gly Val Ala Pro Glu Val Asn Ala Lys Ala Leu Ala Trp
65                  70                  75                  80

Gly Lys Gln Tyr Glu Asn Asp Ala Arg Thr Leu Phe Glu Phe Thr Ser
                85                  90                  95

Gly Val Asn Val Thr Glu Ser Pro Ile Ile Tyr Arg Asp Glu Ser Met
            100                 105                 110

Arg Thr Ala Cys Ser Pro Asp Gly Leu Cys Ser Asp Gly Asn Gly Leu
        115                 120                 125

Glu Leu Lys Cys Pro Phe Thr Ser Arg Asp Phe Met Lys Phe Arg Leu
    130                 135                 140

Gly Gly Phe Glu Ala Ile Lys Ser Ala Tyr Met Ala Gln Val Gln Tyr
145                 150                 155                 160

Ser Met Trp Val Thr Arg Lys Asn Ala Trp Tyr Phe Ala Asn Tyr Asp
                165                 170                 175

Pro Arg Met Lys Arg Glu Gly Leu His Tyr Val Val Ile Glu Arg Asp
            180                 185                 190

Glu Lys Tyr Met Ala Ser Phe Asp Glu Ile Val Pro Glu Phe Ile Glu
        195                 200                 205

Lys Met Asp Glu Ala Leu Ala Glu Ile Gly Phe Val Phe Gly Glu Gln
    210                 215                 220

Trp Arg
225

<210> SEQ ID NO 5
<211> LENGTH: 608
<212> TYPE: PRT
<213> ORGANISM: Unknown
<220> FEATURE:
<223> OTHER INFORMATION: Bacillus subtilis phage Phi 29

<400> SEQUENCE: 5

Met Lys His Met Pro Arg Lys Met Tyr Ser Cys Ala Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

```
Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Tyr
    210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
    290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365

Tyr Ile Lys Thr Thr Ser Glu Gly Ala Ile Lys Gln Leu Ala Lys Leu
    370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
            420                 425                 430

Ile Thr Ala Trp Ala Arg Tyr Thr Thr Ile Thr Ala Ala Gln Ala Cys
        435                 440                 445

Tyr Asp Arg Ile Ile Tyr Cys Asp Thr Asp Ser Ile His Leu Thr Gly
    450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
                485                 490                 495

Gln Lys Thr Tyr Ile Gln Asp Ile Tyr Met Lys Glu Val Asp Gly Lys
            500                 505                 510

Leu Val Glu Gly Ser Pro Asp Asp Tyr Thr Asp Ile Lys Phe Ser Val
        515                 520                 525

Lys Cys Ala Gly Met Thr Asp Lys Ile Lys Lys Glu Val Thr Phe Glu
    530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys Ser
                565                 570                 575

Gly Gly Ser Ala Trp Ser His Pro Gln Phe Glu Lys Gly Gly Gly Ser
            580                 585                 590
```

```
Gly Gly Gly Ser Gly Gly Ser Ala Trp Ser His Pro Gln Phe Glu Lys
        595                 600                 605


<210> SEQ ID NO 6
<211> LENGTH: 970
<212> TYPE: PRT
<213> ORGANISM: Unknown
<220> FEATURE:
<223> OTHER INFORMATION: Citromicrobium bathyomarinum

<400> SEQUENCE: 6

Met Leu Ser Val Ala Asn Val Arg Ser Pro Ser Ala Ala Ala Ser Tyr
1               5                   10                  15

Phe Ala Ser Asp Asn Tyr Tyr Ala Ser Ala Asp Ala Asp Arg Ser Gly
            20                  25                  30

Gln Trp Ile Gly Asp Gly Ala Lys Arg Leu Gly Leu Glu Gly Lys Val
        35                  40                  45

Glu Ala Arg Ala Phe Asp Ala Leu Leu Arg Gly Glu Leu Pro Asp Gly
    50                  55                  60

Ser Ser Val Gly Asn Pro Gly Gln Ala His Arg Pro Gly Thr Asp Leu
65                  70                  75                  80

Thr Phe Ser Val Pro Lys Ser Trp Ser Leu Leu Ala Leu Val Gly Lys
                85                  90                  95

Asp Glu Arg Ile Ile Ala Ala Tyr Arg Glu Ala Val Val Glu Ala Leu
            100                 105                 110

His Trp Ala Glu Lys Asn Ala Ala Glu Thr Arg Val Val Glu Lys Gly
        115                 120                 125

Met Val Val Thr Gln Ala Thr Gly Asn Leu Ala Ile Gly Leu Phe Gln
    130                 135                 140

His Asp Thr Asn Arg Asn Gln Glu Pro Asn Leu His Phe His Ala Val
145                 150                 155                 160

Ile Ala Asn Val Thr Gln Gly Lys Asp Gly Lys Trp Arg Thr Leu Lys
                165                 170                 175

Asn Asp Arg Leu Trp Gln Leu Asn Thr Thr Leu Asn Ser Ile Ala Met
            180                 185                 190

Ala Arg Phe Arg Val Ala Val Glu Lys Leu Gly Tyr Glu Pro Gly Pro
        195                 200                 205

Val Leu Lys His Gly Asn Phe Glu Ala Arg Gly Ile Ser Arg Glu Gln
    210                 215                 220

Val Met Ala Phe Ser Thr Arg Arg Lys Glu Val Leu Glu Ala Arg Arg
225                 230                 235                 240

Gly Pro Gly Leu Asp Ala Gly Arg Ile Ala Ala Leu Asp Thr Arg Ala
                245                 250                 255

Ser Lys Glu Gly Ile Glu Asp Arg Ala Thr Leu Ser Lys Gln Trp Ser
            260                 265                 270

Glu Ala Ala Gln Ser Ile Gly Leu Asp Leu Lys Pro Leu Val Asp Arg
        275                 280                 285

Ala Arg Thr Lys Ala Leu Gly Gln Gly Met Glu Ala Thr Arg Ile Gly
    290                 295                 300

Ser Leu Val Glu Arg Gly Arg Ala Trp Leu Ser Arg Phe Ala Ala His
305                 310                 315                 320

Val Arg Gly Asp Pro Ala Asp Pro Leu Val Pro Pro Ser Val Leu Lys
                325                 330                 335

Gln Asp Arg Gln Thr Ile Ala Ala Ala Gln Ala Val Ala Ser Ala Val
            340                 345                 350
```

```
Arg His Leu Ser Gln Arg Glu Ala Ala Phe Glu Arg Thr Ala Leu Tyr
        355                 360                 365

Lys Ala Ala Leu Asp Phe Gly Leu Pro Thr Thr Ile Ala Asp Val Glu
    370                 375                 380

Lys Arg Thr Arg Ala Leu Val Arg Ser Gly Asp Leu Ile Ala Gly Lys
385                 390                 395                 400

Gly Glu His Lys Gly Trp Leu Ala Ser Arg Asp Ala Val Val Thr Glu
                405                 410                 415

Gln Arg Ile Leu Ser Glu Val Ala Ala Gly Lys Gly Asp Ser Ser Pro
            420                 425                 430

Ala Ile Thr Pro Gln Lys Ala Ala Ala Ser Val Gln Ala Ala Ala Leu
        435                 440                 445

Thr Gly Gln Gly Phe Arg Leu Asn Glu Gly Gln Leu Ala Ala Ala Arg
    450                 455                 460

Leu Ile Leu Ile Ser Lys Asp Arg Thr Ile Ala Val Gln Gly Ile Ala
465                 470                 475                 480

Gly Ala Gly Lys Ser Ser Val Leu Lys Pro Val Ala Glu Val Leu Arg
                485                 490                 495

Asp Glu Gly His Pro Val Ile Gly Leu Ala Ile Gln Asn Thr Leu Val
            500                 505                 510

Gln Met Leu Glu Arg Asp Thr Gly Ile Gly Ser Gln Thr Leu Ala Arg
        515                 520                 525

Phe Leu Gly Gly Trp Asn Lys Leu Leu Asp Asp Pro Gly Asn Val Ala
    530                 535                 540

Leu Arg Ala Glu Ala Gln Ala Ser Leu Lys Asp His Val Leu Val Leu
545                 550                 555                 560

Asp Glu Ala Ser Met Val Ser Asn Glu Asp Lys Glu Lys Leu Val Arg
                565                 570                 575

Leu Ala Asn Leu Ala Gly Val His Arg Leu Val Leu Ile Gly Asp Arg
            580                 585                 590

Lys Gln Leu Gly Ala Val Asp Ala Gly Lys Pro Phe Ala Leu Leu Gln
        595                 600                 605

Arg Ala Gly Ile Ala Arg Ala Glu Met Ala Thr Asn Leu Arg Ala Arg
    610                 615                 620

Asp Pro Val Val Arg Glu Ala Gln Ala Ala Ala Gln Ala Gly Asp Val
625                 630                 635                 640

Arg Lys Ala Leu Arg His Leu Lys Ser His Thr Val Glu Ala Arg Gly
                645                 650                 655

Asp Gly Ala Gln Val Ala Ala Glu Thr Trp Leu Ala Leu Asp Lys Glu
            660                 665                 670

Thr Arg Ala Arg Thr Ser Ile Tyr Ala Ser Gly Arg Ala Ile Arg Ser
        675                 680                 685

Ala Val Asn Ala Ala Val Gln Gln Gly Leu Leu Ala Ser Arg Glu Ile
    690                 695                 700

Gly Pro Ala Lys Met Lys Leu Glu Val Leu Asp Arg Val Asn Thr Thr
705                 710                 715                 720

Arg Glu Glu Leu Arg His Leu Pro Ala Tyr Arg Ala Gly Arg Val Leu
                725                 730                 735

Glu Val Ser Arg Lys Gln Gln Ala Leu Gly Leu Phe Ile Gly Glu Tyr
            740                 745                 750

Arg Val Ile Gly Gln Asp Arg Lys Gly Lys Leu Val Glu Val Glu Asp
        755                 760                 765
```

Lys Arg Gly Lys Arg Phe Arg Phe Asp Pro Ala Arg Ile Arg Ala Gly
770 775 780

Lys Gly Asp Asp Asn Leu Thr Leu Leu Glu Pro Arg Lys Leu Glu Ile
785 790 795 800

His Glu Gly Asp Arg Ile Arg Trp Thr Arg Asn Asp His Arg Arg Gly
805 810 815

Leu Phe Asn Ala Asp Gln Ala Arg Val Val Glu Ile Ala Asn Gly Lys
820 825 830

Val Thr Phe Glu Thr Ser Lys Gly Asp Leu Val Glu Leu Lys Lys Asp
835 840 845

Asp Pro Met Leu Lys Arg Ile Asp Leu Ala Tyr Ala Leu Asn Val His
850 855 860

Met Ala Gln Gly Leu Thr Ser Asp Arg Gly Ile Ala Val Met Asp Ser
865 870 875 880

Arg Glu Arg Asn Leu Ser Asn Gln Lys Thr Phe Leu Val Thr Val Thr
885 890 895

Arg Leu Arg Asp His Leu Thr Leu Val Val Asp Ser Ala Asp Lys Leu
900 905 910

Gly Ala Ala Val Ala Arg Asn Lys Gly Glu Lys Ala Ser Ala Ile Glu
915 920 925

Val Thr Gly Ser Val Lys Pro Thr Ala Thr Lys Gly Ser Gly Val Asp
930 935 940

Gln Pro Lys Ser Val Glu Ala Asn Lys Ala Glu Lys Glu Leu Thr Arg
945 950 955 960

Ser Lys Ser Lys Thr Leu Asp Phe Gly Ile
965 970

<210> SEQ ID NO 7
<211> LENGTH: 760
<212> TYPE: PRT
<213> ORGANISM: Methanococcoides burtonii

<400> SEQUENCE: 7

Met Met Ile Arg Glu Leu Asp Ile Pro Arg Asp Ile Ile Gly Phe Tyr
1 5 10 15

Glu Asp Ser Gly Ile Lys Glu Leu Tyr Pro Pro Gln Ala Glu Ala Ile
20 25 30

Glu Met Gly Leu Leu Glu Lys Lys Asn Leu Leu Ala Ala Ile Pro Thr
35 40 45

Ala Ser Gly Lys Thr Leu Leu Ala Glu Leu Ala Met Ile Lys Ala Ile
50 55 60

Arg Glu Gly Gly Lys Ala Leu Tyr Ile Val Pro Leu Arg Ala Leu Ala
65 70 75 80

Ser Glu Lys Phe Glu Arg Phe Lys Glu Leu Ala Pro Phe Gly Ile Lys
85 90 95

Val Gly Ile Ser Thr Gly Asp Leu Asp Ser Arg Ala Asp Trp Leu Gly
100 105 110

Val Asn Asp Ile Ile Val Ala Thr Ser Glu Lys Thr Asp Ser Leu Leu
115 120 125

Arg Asn Gly Thr Ser Trp Met Asp Glu Ile Thr Thr Val Val Val Asp
130 135 140

Glu Ile His Leu Leu Asp Ser Lys Asn Arg Gly Pro Thr Leu Glu Val
145 150 155 160

```
Thr Ile Thr Lys Leu Met Arg Leu Asn Pro Asp Val Gln Val Val Ala
                165                 170                 175

Leu Ser Ala Thr Val Gly Asn Ala Arg Glu Met Ala Asp Trp Leu Gly
            180                 185                 190

Ala Ala Leu Val Leu Ser Glu Trp Arg Pro Thr Asp Leu His Glu Gly
        195                 200                 205

Val Leu Phe Gly Asp Ala Ile Asn Phe Pro Gly Ser Gln Lys Lys Ile
    210                 215                 220

Asp Arg Leu Glu Lys Asp Asp Ala Val Asn Leu Val Leu Asp Thr Ile
225                 230                 235                 240

Lys Ala Glu Gly Gln Cys Leu Val Phe Glu Ser Ser Arg Arg Asn Cys
                245                 250                 255

Ala Gly Phe Ala Lys Thr Ala Ser Ser Lys Val Ala Lys Ile Leu Asp
            260                 265                 270

Asn Asp Ile Met Ile Lys Leu Ala Gly Ile Ala Glu Glu Val Glu Ser
        275                 280                 285

Thr Gly Glu Thr Asp Thr Ala Ile Val Leu Ala Asn Cys Ile Arg Lys
    290                 295                 300

Gly Val Ala Phe His His Ala Gly Leu Asn Ser Asn His Arg Lys Leu
305                 310                 315                 320

Val Glu Asn Gly Phe Arg Gln Asn Leu Ile Lys Val Ile Ser Ser Thr
                325                 330                 335

Pro Thr Leu Ala Ala Gly Leu Asn Leu Pro Ala Arg Arg Val Ile Ile
            340                 345                 350

Arg Ser Tyr Arg Arg Phe Asp Ser Asn Phe Gly Met Gln Pro Ile Pro
        355                 360                 365

Val Leu Glu Tyr Lys Gln Met Ala Gly Arg Ala Gly Arg Pro His Leu
    370                 375                 380

Asp Pro Tyr Gly Glu Ser Val Leu Leu Ala Lys Thr Tyr Asp Glu Phe
385                 390                 395                 400

Ala Gln Leu Met Glu Asn Tyr Val Glu Ala Asp Ala Glu Asp Ile Trp
                405                 410                 415

Ser Lys Leu Gly Thr Glu Asn Ala Leu Arg Thr His Val Leu Ser Thr
            420                 425                 430

Ile Val Asn Gly Phe Ala Ser Thr Arg Gln Glu Leu Phe Asp Phe Phe
        435                 440                 445

Gly Ala Thr Phe Phe Ala Tyr Gln Gln Asp Lys Trp Met Leu Glu Glu
    450                 455                 460

Val Ile Asn Asp Cys Leu Glu Phe Leu Ile Asp Lys Ala Met Val Ser
465                 470                 475                 480

Glu Thr Glu Asp Ile Glu Asp Ala Ser Lys Leu Phe Leu Arg Gly Thr
                485                 490                 495

Arg Leu Gly Ser Leu Val Ser Met Leu Tyr Ile Asp Pro Leu Ser Gly
            500                 505                 510

Ser Lys Ile Val Asp Gly Phe Lys Asp Ile Gly Lys Ser Thr Gly Gly
        515                 520                 525

Asn Met Gly Ser Leu Glu Asp Asp Lys Gly Asp Asp Ile Thr Val Thr
    530                 535                 540

Asp Met Thr Leu Leu His Leu Val Cys Ser Thr Pro Asp Met Arg Gln
545                 550                 555                 560

Leu Tyr Leu Arg Asn Thr Asp Tyr Thr Ile Val Asn Glu Tyr Ile Val
                565                 570                 575
```

Ala His Ser Asp Glu Phe His Glu Ile Pro Asp Lys Leu Lys Glu Thr
580 585 590

Asp Tyr Glu Trp Phe Met Gly Glu Val Lys Thr Ala Met Leu Leu Glu
595 600 605

Glu Trp Val Thr Glu Val Ser Ala Glu Asp Ile Thr Arg His Phe Asn
610 615 620

Val Gly Glu Gly Asp Ile His Ala Leu Ala Asp Thr Ser Glu Trp Leu
625 630 635 640

Met His Ala Ala Ala Lys Leu Ala Glu Leu Leu Gly Val Glu Tyr Ser
645 650 655

Ser His Ala Tyr Ser Leu Glu Lys Arg Ile Arg Tyr Gly Ser Gly Leu
660 665 670

Asp Leu Met Glu Leu Val Gly Ile Arg Gly Val Gly Arg Val Arg Ala
675 680 685

Arg Lys Leu Tyr Asn Ala Gly Phe Val Ser Val Ala Lys Leu Lys Gly
690 695 700

Ala Asp Ile Ser Val Leu Ser Lys Leu Val Gly Pro Lys Val Ala Tyr
705 710 715 720

Asn Ile Leu Ser Gly Ile Gly Val Arg Val Asn Asp Lys His Phe Asn
725 730 735

Ser Ala Pro Ile Ser Ser Asn Thr Leu Asp Thr Leu Leu Asp Lys Asn
740 745 750

Gln Lys Thr Phe Asn Asp Phe Gln
755 760

<210> SEQ ID NO 8
<211> LENGTH: 439
<212> TYPE: PRT
<213> ORGANISM: Unknown
<220> FEATURE:
<223> OTHER INFORMATION: Enterobacteria phage T4

<400> SEQUENCE: 8

Met Thr Phe Asp Asp Leu Thr Glu Gly Gln Lys Asn Ala Phe Asn Ile
1 5 10 15

Val Met Lys Ala Ile Lys Glu Lys Lys His His Val Thr Ile Asn Gly
20 25 30

Pro Ala Gly Thr Gly Lys Thr Thr Leu Thr Lys Phe Ile Ile Glu Ala
35 40 45

Leu Ile Ser Thr Gly Glu Thr Gly Ile Ile Leu Ala Ala Pro Thr His
50 55 60

Ala Ala Lys Lys Ile Leu Ser Lys Leu Ser Gly Lys Glu Ala Ser Thr
65 70 75 80

Ile His Ser Ile Leu Lys Ile Asn Pro Val Thr Tyr Glu Glu Asn Val
85 90 95

Leu Phe Glu Gln Lys Glu Val Pro Asp Leu Ala Lys Cys Arg Val Leu
100 105 110

Ile Cys Asp Glu Val Ser Met Tyr Asp Arg Lys Leu Phe Lys Ile Leu
115 120 125

Leu Ser Thr Ile Pro Pro Trp Cys Thr Ile Ile Gly Ile Gly Asp Asn
130 135 140

Lys Gln Ile Arg Pro Val Asp Pro Gly Glu Asn Thr Ala Tyr Ile Ser
145 150 155 160

Pro Phe Phe Thr His Lys Asp Phe Tyr Gln Cys Glu Leu Thr Glu Val
165 170 175

```
Lys Arg Ser Asn Ala Pro Ile Ile Asp Val Ala Thr Asp Val Arg Asn
            180                 185                 190

Gly Lys Trp Ile Tyr Asp Lys Val Val Asp Gly His Gly Val Arg Gly
        195                 200                 205

Phe Thr Gly Asp Thr Ala Leu Arg Asp Phe Met Val Asn Tyr Phe Ser
    210                 215                 220

Ile Val Lys Ser Leu Asp Asp Leu Phe Glu Asn Arg Val Met Ala Phe
225                 230                 235                 240

Thr Asn Lys Ser Val Asp Lys Leu Asn Ser Ile Ile Arg Lys Lys Ile
                245                 250                 255

Phe Glu Thr Asp Lys Asp Phe Ile Val Gly Glu Ile Ile Val Met Gln
            260                 265                 270

Glu Pro Leu Phe Lys Thr Tyr Lys Ile Asp Gly Lys Pro Val Ser Glu
        275                 280                 285

Ile Ile Phe Asn Asn Gly Gln Leu Val Arg Ile Ile Glu Ala Glu Tyr
    290                 295                 300

Thr Ser Thr Phe Val Lys Ala Arg Gly Val Pro Gly Glu Tyr Leu Ile
305                 310                 315                 320

Arg His Trp Asp Leu Thr Val Glu Thr Tyr Gly Asp Asp Glu Tyr Tyr
                325                 330                 335

Arg Glu Lys Ile Lys Ile Ile Ser Ser Asp Glu Glu Leu Tyr Lys Phe
            340                 345                 350

Asn Leu Phe Leu Gly Lys Thr Ala Glu Thr Tyr Lys Asn Trp Asn Lys
        355                 360                 365

Gly Gly Lys Ala Pro Trp Ser Asp Phe Trp Asp Ala Lys Ser Gln Phe
    370                 375                 380

Ser Lys Val Lys Ala Leu Pro Ala Ser Thr Phe His Lys Ala Gln Gly
385                 390                 395                 400

Met Ser Val Asp Arg Ala Phe Ile Tyr Thr Pro Cys Ile His Tyr Ala
                405                 410                 415

Asp Val Glu Leu Ala Gln Gln Leu Leu Tyr Val Gly Val Thr Arg Gly
            420                 425                 430

Arg Tyr Asp Val Phe Tyr Val
        435
```

<210> SEQ ID NO 9
<211> LENGTH: 60
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (33)..(34)
<223> OTHER INFORMATION: May be linked via four iSp18 linkers
<220> FEATURE:
<221> NAME/KEY: modified_base
<222> LOCATION: (34)..(34)
<223> OTHER INFORMATION: May be modified by iBNA
<220> FEATURE:
<221> NAME/KEY: modified_base
<222> LOCATION: (35)..(35)
<223> OTHER INFORMATION: May be modified by iBNA
<220> FEATURE:
<221> NAME/KEY: modified_base
<222> LOCATION: (36)..(36)
<223> OTHER INFORMATION: May be modified by iBNA
<220> FEATURE:
<221> NAME/KEY: modified_base
<222> LOCATION: (37)..(37)
<223> OTHER INFORMATION: May be modified by iBNA
<220> FEATURE:

<221> NAME/KEY: modified_base
<222> LOCATION: (38)..(38)
<223> OTHER INFORMATION: May be modified by iBNA

<400> SEQUENCE: 9
cctttttttt ggcgtctgct tgggtgttta accccacaac ttcgttcagt tacgtattgc 60

<210> SEQ ID NO 10
<211> LENGTH: 33
<212> TYPE: DNA
<213> ORGANISM: Artificial Sequence
<220> FEATURE:
<223> OTHER INFORMATION: Synthetic

<400> SEQUENCE: 10
ggttaaacac ccaagcagac gccaaaaaaa agg 33

<210> SEQ ID NO 11
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (23)..(23)
<223> OTHER INFORMATION: May be modified by iBNA
<220> FEATURE:
<221> NAME/KEY: modified_base
<222> LOCATION: (24)..(24)
<223> OTHER INFORMATION: May be modified by iBNA
<220> FEATURE:
<221> NAME/KEY: modified_base
<222> LOCATION: (25)..(25)
<223> OTHER INFORMATION: May be modified by iBNA
<220> FEATURE:
<221> NAME/KEY: modified_base
<222> LOCATION: (26)..(26)
<223> OTHER INFORMATION: May be modified by iBNA
<220> FEATURE:
<221> NAME/KEY: modified_base
<222> LOCATION: (27)..(27)
<223> OTHER INFORMATION: May be modified by iBNA

<400> SEQUENCE: 11
gcaatacgta actgaacgaa gttgtgg 27

<210> SEQ ID NO 12
<211> LENGTH: 23
<212> TYPE: DNA
<213> ORGANISM: Artificial Sequence
<220> FEATURE:
<223> OTHER INFORMATION: Synthetic

<400> SEQUENCE: 12
ccaagcagac gccaaaaaaa agg 23

<210> SEQ ID NO 13
<211> LENGTH: 61
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (33)..(34)
<223> OTHER INFORMATION: May be separated by a spacer sequence

<400> SEQUENCE: 13
cctttttttt ggcgtctgct tgggtgttta accccacaac ttcgttcagt tacgtattgc 60
t 61

<210> SEQ ID NO 14
<211> LENGTH: 33
<212> TYPE: DNA
<213> ORGANISM: Artificial Sequence
<220> FEATURE:
<223> OTHER INFORMATION: Synthetic

<400> SEQUENCE: 14
cctttttttt ggcgtctgct tgggtgttta acc 33

<210> SEQ ID NO 15
<211> LENGTH: 33
<212> TYPE: DNA
<213> ORGANISM: Artificial Sequence
<220> FEATURE:
<223> OTHER INFORMATION: Synthetic

<400> SEQUENCE: 15
cctttttttt ggcgtctgct tgggtgttta acc 33

<210> SEQ ID NO 16
<211> LENGTH: 28
<212> TYPE: DNA
<213> ORGANISM: Artificial Sequence
<220> FEATURE:
<223> OTHER INFORMATION: Synthetic

<400> SEQUENCE: 16
ccacaacttc gttcagttac gtattgct 28

<210> SEQ ID NO 17
<211> LENGTH: 27
<212> TYPE: DNA
<213> ORGANISM: Artificial Sequence
<220> FEATURE:
<223> OTHER INFORMATION: Synthetic

<400> SEQUENCE: 17
gcaatacgta actgaacgaa gttgtgg 27

<210> SEQ ID NO 18
<211> LENGTH: 26
<212> TYPE: DNA
<213> ORGANISM: Artificial Sequence
<220> FEATURE:
<223> OTHER INFORMATION: Synthetic

<400> SEQUENCE: 18
ggttaaacac ccaagcagac gccttt 26

<210> SEQ ID NO 19
<211> LENGTH: 33
<212> TYPE: DNA
<213> ORGANISM: Artificial Sequence
<220> FEATURE:
<223> OTHER INFORMATION: Synthetic

<400> SEQUENCE: 19
ggttaaacac ccaagcagac gccaaaaaaa agg 33